United States Patent
Parkos et al.

(10) Patent No.: US 9,605,083 B2
(45) Date of Patent: Mar. 28, 2017

(54) JAML SPECIFIC BINDING AGENTS, ANTIBODIES, AND USES RELATED THERETO

(75) Inventors: Charles A. Parkos, Norcross, GA (US); Dominique A. Weber, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/238,556

(22) PCT Filed: Aug. 10, 2012

(86) PCT No.: PCT/US2012/050286
§ 371 (c)(1),
(2), (4) Date: Apr. 16, 2014

(87) PCT Pub. No.: WO2013/025479
PCT Pub. Date: Feb. 21, 2013

(65) Prior Publication Data
US 2014/0242068 A1    Aug. 28, 2014

Related U.S. Application Data

(60) Provisional application No. 61/523,886, filed on Aug. 16, 2011, provisional application No. 61/563,064, filed on Nov. 23, 2011.

(51) Int. Cl.
| | |
|---|---|
| *C07K 16/00* | (2006.01) |
| *C07K 16/42* | (2006.01) |
| *C07K 16/28* | (2006.01) |
| *A61K 39/00* | (2006.01) |

(52) U.S. Cl.
CPC .......... *C07K 16/42* (2013.01); *C07K 16/2803* (2013.01); *A61K 2039/505* (2013.01); *C07K 2317/33* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,041,804 B2 * | 5/2006 | Desnoyers | ......... | C07K 14/4713 530/350 |
| 8,017,344 B2 | 9/2011 | Yamaguchi | | |
| 9,175,073 B2 * | 11/2015 | Yamaguchi | ............. | C07K 16/18 |
| 2004/0005647 A1 | 1/2004 | Denardo | | |
| 2008/0248502 A1 * | 10/2008 | Yamaguchi | ............. | C07K 16/18 435/7.24 |
| 2011/0294986 A1 * | 12/2011 | Yamaguchi | ............. | C07K 16/18 530/387.9 |

FOREIGN PATENT DOCUMENTS

EP    1777235    4/2007

OTHER PUBLICATIONS

Verdino et al. The molecular interaction of CAR and JAML recruits the central cell signal transducer Pl3K. Science. Sep. 3, 2010; 329(5996): 1210-1214.*
Paul, Fundamental Immunology, 3rd Edition, 1993, pp. 292-295.*
Rudikoff et al Single amino acid substitution altering antigen-binding specificity. Proc Natl Acad Sci U S A. Mar. 1982;79(6):1979-83.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Zen et al. Neutrophil Migration across Tight Junctions Is Mediated by Adhesive Interactions between Epithelial Coxsackie and Adenovirus Receptor and a Junctional Adhesion Molecule-like Protein on Neutrophils. Mol Biol Cell. Jun. 2005; 16(6): 2694-2703.*
Zen et al. Neutrophil migration across epithelial tight junctions is regulated by binding interactions between JAML and CAR. FASEB Journal, (Mar. 7, 2005) vol. 19, No. 5, Suppl. S, Part 2, pp. A1526.*
Moog-Lutz et al. JAML, a novel protein with characteristics of a junctional adhesion molecule, is induced during differentiation of myeloid leukemia cells. Blood 102 (9): 3371-8.*
Brown et al. "Tolerance of single, but not multiple, amino acid replacements in antibody VH CDR 2: a means of minimizing B cell wastage from somatic hypermutation?" J. Immuno., May 1996; 3285-3291.
GENBANK ACC53239.1 Anti-polycation monoclonal antibody, Ig light chain variable region, partial [Mus musculus].
Guo et al. "Role of Junctional Adhesion Molecule-Like Protein in Mediating Monocyte Transendothelial Migration Arterioscler" Thromb Vasc Biol., 2009; 29: 75-83.
Kendrick et al. "A gene's mRNA level does not usually predict its protein level" Kendrick Labs, Inc., Sep. 25, 2014; Retrieved from the Internet: URL:http://www.kendricklabs.com/WP1_mRNAvsProtein-New2014.pdf.
Luissint et al. "JAM-L—mediated leukocyte adhesion to endothelial cells is regulated in cis by alpha 4 beta 1 integrin activation" J Cell Biol, 2008; 183: 1159-1173.
Monestier et al. "Induction of Anti-Polycation Antibodies in H-2; Mice by Immunization With Nuclear Antigens" Molecular Immunology, 1997; 34(1): 39-51.
Moog-Lutz et al. "JAML, a novel protein with characteristics of a junctional adhesion molecule, is induced during differentiation of myeloid leukemia cells" Blood, 2003; 102(9): 3371-3378.
Rudikoff et al. "Single amino acid substitution altering antigen-binding specificity" Proc Natl Acad Sci U S A., Mar. 1982; 79(6): 1979-1983.
Sasse et al. "Coxsackie-and-adenovirus receptor mRNA expression in human heart failure" J Gene Med, 2003; 5: 876-882.
Vajdos et al. "Comprehensive functional maps of the antigen-binding site of an anti-ErbB2 antibody obtained with shotgun scanning mutagenesis" J. Mol. Biol., Jul. 5, 2002; 320(2): 415-428.

(Continued)

*Primary Examiner* — Maher Haddad
(74) *Attorney, Agent, or Firm* — Emory Patent Group

(57) ABSTRACT

Disclosed are specific binding agents such as antibodies and chimera that bind to JAM-like protein. Also disclosed are heavy chain fragments, light chain fragments, and CDRs of the antibodies, as well as methods related thereto.

4 Claims, 24 Drawing Sheets

(56) References Cited

OTHER PUBLICATIONS

Verdino et al. "The molecular interaction of CAR and JAML recruits the central cell signal transducer Pl3K" Science, 2010; 329(5996): 1210-1214.
Weber et al. "Neutrophil-derived JAML inhibits repair of intestinal epithelial injury during acute inflammation" Mucosal Immunology, 2014; 7: 1221-1232.
Witherden et al. "The junctional adhesion molecule JAML is a costimulatory receptor for epithelial gammadelta T cell activation" Science, 2010; 329(5996): 1205-1210.
Zen et al. "Leukocyte—epithelial interactions" Current Opinion in Cell Biology, 2003; 15: 557-564.
Zen et al. "Neutrophil Migration across Tight Junctions Is Mediated by Adhesive Interactions between Epithelial Coxsackie and Adenovirus Receptor and a Junctional Adhesion Molecule-like Protein on Neutrophils" Mol Biol Cell., 2005; 16(6): 2694-2703.
Communication pursuant to Article 94(3) EPC issued Oct. 30, 2015 for EP Application No. 12824085.0.
Extended European Search Report issued Nov. 11, 2014 for EP Application No. 12824085.0.

\* cited by examiner

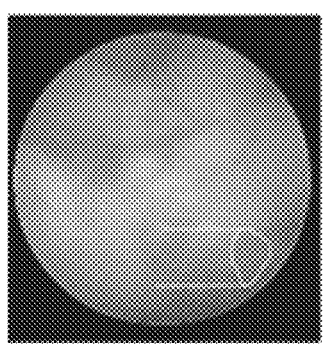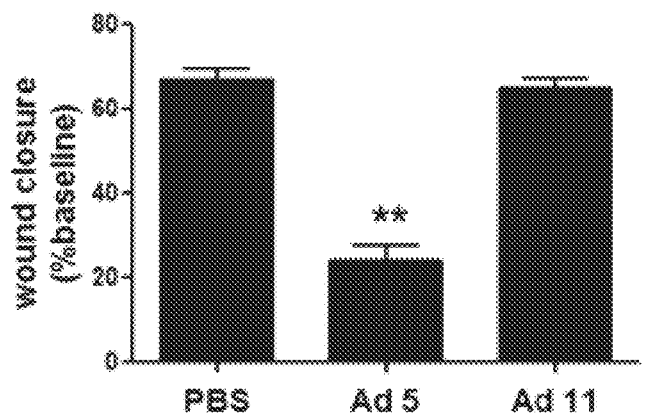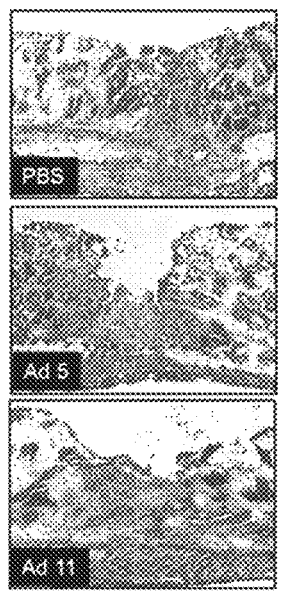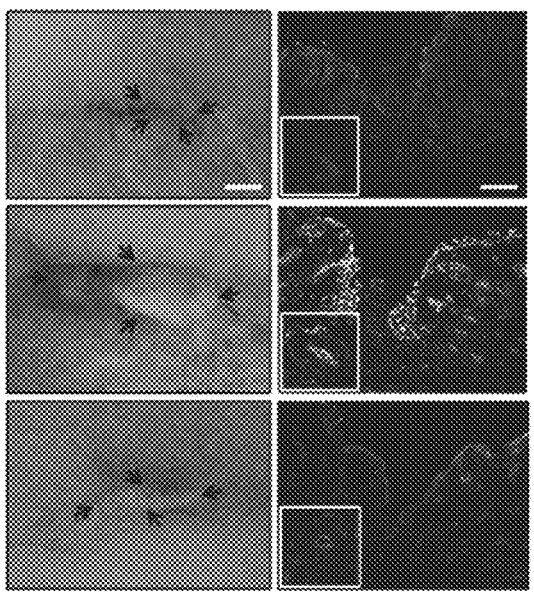
FIG. 13A                FIG. 13B
FIG. 13C     FIG. 13D     FIG. 13E

JAML SPECIFIC BINDING AGENTS, ANTIBODIES, AND USES RELATED THERETO

CROSS-REFERENCE TO RELATED APPLICATIONS

This application is the National Stage of International Application No. PCT/US2012/050286 filed Aug. 10, 2012, which claims priority to U.S. Provisional Application No. 61/523,886 filed Aug. 16, 2011 and U.S. Provisional Application No. 61/563,064 filed Nov. 23, 2011. The entirety of each of these applications is hereby incorporated by reference for all purposes.

STATEMENT REGARDING FEDERALLY FUNDED RESEARCH

This invention was made with government support under contract DK72564 RO1 awarded by the NIH. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 11181US_2016-09-21_ST25.txt. The text file is 56 MB, was created on Sep. 21, 2016, and is being submitted electronically via EFS-Web.

FIELD

This disclosure relates to agents that specifically bind JAM-like protein (JAML). The binding agents, such as antibodies, bind the extracellular domain of JAML making them particularly useful in a variety of settings such as diagnostic screening, bioassays, and therapeutic intervention for diseases or conditions that are associated with JAML and/or CAR such as inflammation, cancer, scarring, wound healing, respiratory diseases, and other disorders related to epithelial inflammation.

BACKGROUND

Polymorphonuclear neutrophils (PMNs) are an important component of innate immunity. In the intestine PMNs are rapidly recruited towards the regions that have been compromised by invading bacterial pathogens, thus providing the first line of defense. However, their influx into mucosa also characterizes many inflammatory diseases including Crohn's and Ulcerative Colitis where increased numbers of infiltrating PMNs cause damage to the intestinal wall. During inflammation PMNs exit the blood vessels and are driven towards and across epithelium by chemoattracting forces. Diffusion of bacterial derived peptides, such as fMLF, across epithelial layer as well as basolateraly secreted epithelium-derived chemokines, such as IL-8, establish a chemoattractant gradient that guides PMNs towards the sites of inflammation. PMNs encountering proinflammatory stimuli undergo morphological changes as well as changes in the expression of surface adhesive receptors. For example, $\beta 2$-integrin CD11b/CD18, which is important for the initial PMN adhesion to both endothelium and epithelium, is upregulated upon PMN activation. In contrast, expression of L-selectin, another adhesive receptor that mediates initial PMN rolling in blood vessels, is completely lost upon PMN activation and migration.

Epithelial and endothelial proteins expressed at intercellular junctions and members of the immunoglobulin superfamily (IgSf) members have been implicated directly or indirectly in regulating PMN trafficking and a variety of epithelial/endothelial cell functions. Function of these proteins is, in part, mediated through homo- and heterotypic interactions with related family members and integrins. JAM-A, for example is abundantly expressed at the epithelial apical junctional complexes (AJC) as well as on PMNs. PMNs from JAM-A deficient mice (JAMA -/-) exhibit impaired migration. Another related molecule, JAML, is not present in epithelial or endothelial cells.

JAML has been shown to bind specifically to the cosackie adenovirus receptor (CAR), which is another member of the Ig superfamily. CAR is expressed at tight junctions of epithelial cells and to some degree on subtypes of endothelial cells, and localizes to the tight junctions (TJ). Both JAML and CAR are type I glycoproteins composed of two extracellular immunoglobulin domains, a single transmembrane helix, and a cytoplasmic domain. CAR has been shown to form homodimers in cis via the membrane distal D1 domain. CAR has been implicated in regulating epithelial permeability and cell adhesion to extracellular matrix by controlling the localization of cell integrins. JAML plays a role in regulating monocyte transendothelial migration and neutrophil transepithelial migration by binding to the endothelial CAR and other tight junction-associated adhesive molecules. See Zen et al., Mol. Biol. Cell, 2005, 16(6):2694-2703, Ya-Lan et al., Arteriosclerosis, Thrombosis, and Vascular Biology, 2009, 29: 75-83, and Witherden et al., Science, 2010, 329 (5996): 1205-1210. CAR and JAML are cell signaling receptors of the immune system with implications for asthma, cancer, and chronic non-healing wounds. See Verdino et al., Science, 2010, 1210-1211.

Monoclonal anti-mouse JAML antibody (clone 4E10) may be purchased from eBiosciences. See also Luissint et al., J Cell Biol, 2008, 183:1159-1173; U.S. Pat. No. 8,017, 344; and U.S. Published Application No. 2008/0248502.

SUMMARY

Certain embodiments of the disclosure relate to targeted binding agents that specifically bind to JAM-like protein and therein inhibit epithelial damage. Although it is not intended that embodiments of the disclosure be limited by any particular mechanism, it is believed that a possible mechanism by which this can be achieved may include, but are not limited to, either inhibition of binding of JAML to the CAR, inhibition of JAML induced CAR signaling, or increased clearance of JAML from the body of a subject, therein reducing the effective concentration of soluble JAML. In certain embodiment, the specific binding agent is a fully human antibody or chimera that specifically binds to human JAML, such as the JAML D1, and prevents JAML binding to CAR. Certain embodiments of the disclosure contemplate antibodies comprising human IgG type, e.g., IgG1, IgG2, IgG3, and IgG4.

In certain embodiments, the disclosure relates to binding agents such as antibodies with an epitope to the extracellular domain of human JAML, such as D1. The antibody may be a monoclonal antibody that does not substantially bind GBP, JAMA, JAMC, CLMP, EVA, SIRPA, and CAR. The antibody may substantially inhibit binding of CAR to JAML. The antibody may slow PMN transmigration across epithelial cells. The antibody may be a human antibody or human chimera.

In certain embodiments, the binding agents are isolated antibodies such as DW100 expressed by the hybridoma having ATCC Deposit No. PTA-13051.

In certain embodiments, the binding agent is an antigen binding fragment wherein the antigen-binding fragment retains the binding specificity of the monoclonal antibody expressed by the cell line for DW100 having ATCC No PTA-13051.

In certain embodiments, the disclosure relates to a host cell line for DW100 having ATCC No. PTA-13051.

CDR1, CDR2, and CDR3 of DW100 heavy chain are respectively (SEQ ID NO:1) DYEMH; (SEQ ID NO:2) WIGIIH$^1$PGSGGTVYNH$^2$KFKGKA wherein H$^2$ may be Q; (SEQ ID NO:3) TRRRY$^1$Y$^2$GS$^1$S$^2$Y$^3$NWYFDV wherein S$^1$ is optionally substituted with E and Y$^1$ is optionally substituted with T;

CDR1, CDR2, and CDR3 of DW55 heavy chain are respectively (SEQ ID NO:4) DYGMA; (SEQ ID NO:5) FISNLAYSIYYSDTVT; (SEQ ID NO:6) ARGDYSGGMMDY;

CDR1, CDR2, and CDR3 of DW216 heavy chain are respectively (SEQ ID NO:7) DYAWN; (SEQ ID NO:8) SSSGNSNYNPSLKS; and (SEQ ID NO:9) AGATGYSMDY;

CDR1, CDR2, and CDR3 of DW100 which light chain are respectively (SEQ ID NO:10) CRASENIYYSLAW; (SEQ ID NO:11) NANSLEDGVPSR; L3 (SEQ ID NO:12) YFCEQTYDVPLTFGAGT;

CDR1, CDR2, and CDR3 of DW55 light chain which are respectively (SEQ ID NO:13) SYRASKSVSTSGYS; (SEQ ID NO:14) LVSNLESGVPARF; (SEQ ID NO:15) QHIRELTRSEGGPS;

CDR1, CDR2, and CDR3 of DW216 light chain which are respectively (SEQ ID NO:16) TASSSVSSSYL; (SEQ ID NO:17) STSNLASGVPARF; (SEQ ID NO:18) HQYHRSPFTFGS.

In certain embodiments, the binding agents comprising a polypeptide of a more than 5, 6, 7, 8, 9, 10, 11, 12, 13, 14, 15, 16, 17, 18, 19, or 20 continuous amino acids within DW100, DW55, and DW216, e.g., having at least 8 or 9 is contemplated. Contemplated continuous sequences are typically within the variable regions of the light and heavy chains of the antibodies, e.g., CDR regions. In certain embodiments, a binding agent substantially prevents JAML from binding CAR. In certain embodiments, the antibody does not substantially bind to JAMA or JAMC. In certain embodiments, the antibody binds the D1 domain of JAML. Typically, the antibody is a monoclonal antibody.

In certain embodiments, the disclosure relates to a JAML binding agent comprising a sequence selected from SEQ ID NOs: 1, 2, 3, 4, 5, 6, 7, 8, 9, 10, 11, 12, 13, 14, 15, 16, 17, and 18 or fragment thereof and a human immunoglobulin provided the fragment is at least 4, 5, 6, 7, 8, 9, or 10 more continuous amino acids.

In certain embodiments, the disclosure relates to a binding agent such as an antibody comprising a heavy chain and a light chain, wherein said heavy chain comprises a heavy chain variable region selected from the group consisting of: H1 of DW100 (SEQ ID NO:19)
DVQLVESGAELVRPGASKLSCKALAYTFTDYEMH-WVKQTPVHGLEWIGIIHPGS GGTVYNQKFKGKATL-TADKSSSTAYMELSSLTSEDSTVYYC-TRRRYYGSSYNWYFDVWGAGN;

H2 of DW55 (SEQ ID NO:20) CDVQLVESGGGLVQPGGSRKLSCAASGFTFSDYG-MAWVRQAPGKGPEWVAFISN LAYSIYYSDTVTGR-FTISRENAKNTLYLEMSSLRSEDTAMYY-CARGDYSGGMMD YWGQGT; and H3 of DW 216 (SEQ ID NO:21) DVQLVESGPGLVKPSQSLSLTCTVTGYSITSDYAWN-WIRQFPGNKLEWMGYISSS GNSNYNPSLKSRISI-TRDTSKNQFFLQLNSVTTEDTATYYCAGATGYSM-DYWGQG TTLTVK;

and said light chain comprises a light chain variable region selected from the group consisting of: L1 of DW100 (SEQ ID NO:22) VLTQSPASLAASVGETVTITCRASENIYYSLAWYQQK QGKSPQLL*IYNANSLEDG VPSRFSGSGSGTQYS-LKINSMQPEDTATYFCEQTYDVPLTFGAGTKLEL;

wherein L* may be optionally substituted with M.

L2 of DW55 (SEQ ID NO:23) VLTSQPASLAVSLGQRATISYRASKSVSTSGYSYMH-WNQQKPGQPPRLLIYLVSN LESGVPARFSGSGSGTD-FTLNIHPVEEEDAATYYCQHIRELTRSEGGPSWK; and L3 of DW216 (SEQ ID NO:24) VLTQSPAIMSASLGERVTMTCTASSSVSSSYLHWY-QQKPGSSPKLWIYSTSNLASG VPARFSGSGSGTSYS-LTISSMEAEDAATYYCHQYHRSPFTFGSGTKLELK.

The disclosure also provides a specific binding agent comprising at least one, two, or three peptides selected from the group consisting of: (SEQ ID NO:1); (SEQ ID NO:2); (SEQ ID NO:3); (SEQ ID NO:4); (SEQ ID NO:5); (SEQ ID NO:6); (SEQ ID NO:7); (SEQ ID NO:8); (SEQ ID NO:9); (SEQ ID NO:10); (SEQ ID NO:11); (SEQ ID NO:12); (SEQ ID NO:13); (SEQ ID NO:14); (SEQ ID NO:15); (SEQ ID NO:16); (SEQ ID NO:17); and (SEQ ID NO:18). The binding agent may contain one, two, or three mutations or conservative substitutions in any of SEQ ID NO:1-18.

The disclosure also provides a specific binding agent comprising; (SEQ ID NO:19); (SEQ ID NO:20); (SEQ ID NO:21); (SEQ ID NO:22); (SEQ ID NO:23); (SEQ ID NO:24) or those with 60%, 65%, 70%, 75%, 80%, 83%, 85%, 87%, 90%, 91%, 92%, 93%, 94%, 95%, 96%, 97%, 98% identity with SEQ ID NO:19-24. In certain embodiments, SEQ ID NOs:19-24 comprises 1 or 2 mutations or 3 or 4 mutation. In certain embodiments, SEQ ID NOs:19-24 comprises 1 or 2 amino acid insertions or 3 or 4 amino acid insertions. The identity may be determined over a 30, 40, 50, 60, or 70 amino acid sequence window within or from the N or C terminal ends of SEQ ID NO:19-24.

The disclosure also provides a specific binding agent comprising; (SEQ ID NO:79); (SEQ ID NO:80); (SEQ ID NO:81); (SEQ ID NO:82) (SEQ ID NO:85) or those with 60%, 65%, 70%, 75%, 80%, 83%, 85%, 87%, 90%, 91%, 92%, 93%, 94%, 95%, 96%, 97%, 98% identity with SEQ ID NO:79-82, 85. In certain embodiments, SEQ ID NOs: 79-82, 85 comprise 1 or 2 mutations or 3 or 4 mutation. In certain embodiments, SEQ ID NOs:79-82, 85 comprise 1 or 2 amino acid insertions or 3 or 4 amino acid insertions. The identity may be determined over a 30, 40, 50, 60, 70, 80, 90, 100, or 150, or 200 amino acid sequence window within or from the N or C terminal ends of SEQ ID NO:19-24.

In an additional embodiment, the disclosure is directed to an isolated antibody comprising a heavy chain and light chain, the heavy chain comprising a heavy chain variable domain and the light chain comprising a light chain variable domain, wherein the heavy chain variable domain comprises 1, 2, or 3 heavy chain CDRs selected from the group of H CDRs consisting of SEQ ID NOs:1, 2, 3, 4, 5, 6, 7, 8, and 9, or fragment thereof and wherein the antibody specifically binds to at least one of JAML and/or JAML D1.

In another embodiment, the disclosure is directed to an isolated antibody which comprises a light chain and a heavy chain, wherein the light chain comprises a light chain variable domain and the heavy chain comprises a heavy chain variable domain, wherein the light chain variable domain comprises 1, 2, or 3, light chain CDRs selected from the group of L CDRs consisting of SEQ ID NOs:10, 11, 12, 13, 14, 15, 16, 17, and 18, or fragment thereof and wherein the antibody specifically binds to at least one of JAML and/or JAML D1.

In a further embodiment, the disclosure is an isolated antibody which comprises a heavy chain and a light chain, wherein the heavy chain comprises a heavy chain variable domain and the light chain comprises a light chain variable domain, wherein the heavy chain comprises 3 heavy chain (HC) CDRs and said light chain variable domain comprises 3 light chain (LC) CDRs, wherein the sequences of said HC and LC CDRs of the antibody are selected from the group consisting of:
   (a) SEQ ID NOs:1, 2, 3 of the HC plus SEQ ID NOs:10, 11, 12 of the LC,
   (b) SEQ ID NOs:4, 5, 6 of the HC plus SEQ ID NOs:13, 14, 15 of the LC,
   (c) SEQ ID NOs:7, 8, 9 of the HC plus SEQ ID NOs:16, 17, 18 of the LC,
wherein the antibody specifically binds to at least one of JAML or JAML D1. Such an antibody may optionally contain 1 or 2 mutations in each of the CDRs.

It will be appreciated that the specific binding agent can be, for example, an antibody, such as a polyclonal, monoclonal, chimeric, humanized, or a fully human antibody. The antibody may also be a single chain antibody with one or two heavy and/or light chains disclosed herein conjugated to a human immunoglobulin. Other examples of specific binding agents include peptibodies, avimers, other forms of peptide molecules (such as Fc-fusion molecules and Ab-fusion molecules) that contain peptide sequences which recognize and bind to a JAML or JAML D1.

In certain embodiments, the disclosure relates to isolated binding agents that bind to JAML or JAML D1 comprising the sequence IHPGSGGTVYN (SEQ ID NO:25) further optionally comprising the sequence YYGSSYN (SEQ ID NO:26) further optionally comprising the sequence DYE (SEQ ID NO:27).

In certain embodiments, the disclosure relates to isolated binding agents that bind to JAML or JAML D1 comprising the sequence HPGSGGTVYN (SEQ ID NO:28) further optionally comprising the sequence YGS (SEQ ID NO:29) further optionally comprising the sequence DYE (SEQ ID NO:27).

In certain embodiments, the disclosure relates to isolated binding agents that bind to JAML or JAML D1 comprising the sequence IHPGSGGTVY (SEQ ID NO:30) further optionally comprising the sequence YGSSYN (SEQ ID NO:31) further optionally comprising the sequence DYE (SEQ ID NO:27).

In certain embodiments, the disclosure relates to isolated binding agents that bind to JAML or JAML D1 comprising the sequence HPGSGGTVY (SEQ ID NO:32) further optionally comprising the sequence YGSSY (SEQ ID NO:33) further optionally comprising the sequence DYE (SEQ ID NO:27).

In certain embodiments, the disclosure relates to isolated binding agents that bind to JAML or JAML D1 comprising the sequence HPGSGGTV (SEQ ID NO:34) further optionally comprising the sequence GSSYN (SEQ ID NO:35) further optionally comprising the sequence DYE (SEQ ID NO:27).

In certain embodiments, the disclosure relates to isolated binding agents that bind to JAML or JAML D1 comprising the sequence HPGSGGT (SEQ ID NO:36) further optionally comprising the sequence GSSYN (SEQ ID NO:35) further optionally comprising the sequence DYE (SEQ ID NO:27).

In certain embodiments, the disclosure relates to isolated binding agents that bind to JAML or JAML D1 comprising the sequence PGSGGT (SEQ ID NO:37) further optionally comprising the sequence GSSYN (SEQ ID NO:35) further optionally comprising the sequence DYE (SEQ ID NO:27).

In certain embodiments, the disclosure relates to isolated binding agents that bind to JAML or JAML D1 comprising the sequence RASENIYYSLA (SEQ ID NO:38) further optionally comprising the sequence NANSLEDGVPS (SEQ ID NO:39).

In certain embodiments, the disclosure relates to isolated binding agents that bind to JAML or JAML D1 comprising the sequence ASENIYYSLA (SEQ ID NO: 40) further optionally comprising the sequence ANSLEDGVPS (SEQ ID NO:41).

In certain embodiments, the disclosure relates to isolated binding agents that bind to JAML or JAML D1 comprising the sequence ASENIYYSL (SEQ ID NO:43) further optionally comprising the sequence ANSLEDGVP (SEQ ID NO:44).

In certain embodiments, the disclosure relates to isolated binding agents that bind to JAML or JAML D1 comprising the sequence SENIYYSL (SEQ ID NO:45) further optionally comprising the sequence NSLEDGVP (SEQ ID NO:46).

In certain embodiments, the disclosure relates to isolated binding agents that bind to JAML or JAML D1 comprising the sequence SENIYYS (SEQ ID NO:47) further optionally comprising the sequence NSLEDGV (SEQ ID NO:48).

In certain embodiments, the disclosure relates to isolated binding agents that bind to JAML or JAML D1 comprising the sequence ENIYYS (SEQ ID NO:49) further optionally comprising the sequence SLEDGV (SEQ ID NO:50).

In certain embodiments, the disclosure relates to isolated binding agents that bind to JAML or JAML D1 comprising the sequence IGIIHPG (SEQ ID NO:51) further optionally comprising the sequence YYGSSYN (SEQ ID NO:26).

In certain embodiments, the disclosure relates to isolated binding agents that bind to JAML or JAML D1 comprising the sequence IGIIHP (SEQ ID NO:52) further optionally comprising the sequence YYGSSYN (SEQ ID NO:26).

In certain embodiments, the disclosure relates to isolated binding agents that bind to JAML or JAML D1 comprising the sequence GIIHPG (SEQ ID NO:53) further optionally comprising the sequence YYGSSYN (SEQ ID NO:26).

In certain embodiments, the disclosure relates to isolated binding agents that bind to JAML or JAML D1 comprising the sequence GIIHP (SEQ ID NO:54) further optionally comprising the sequence YYGSSYN (SEQ ID NO:26).

In certain embodiments, the disclosure relates to isolated binding agents that bind to JAML or JAML D1 comprising the sequence PGSGGTVYNH (SEQ ID NO:55) further optionally comprising the sequence YYGSSYN (SEQ ID NO:26).

In certain embodiments, the disclosure relates to isolated binding agents that bind to JAML or JAML D1 comprising the sequence GSGGTVYNH (SEQ ID NO:56) further optionally comprising the sequence YYGSSYN (SEQ ID NO:26).

In certain embodiments, the disclosure relates to isolated binding agents that bind to JAML or JAML D1 comprising the sequence SGGTVYNH (SEQ ID NO:57) further optionally comprising the sequence YYGSSYN (SEQ ID NO:26).

In certain embodiments, the disclosure relates to isolated binding agents that bind to JAML or JAML D1 comprising the sequence GGTVYNH (SEQ ID NO:58) further optionally comprising the sequence YGS (SEQ ID NO:29).

In certain embodiments, the disclosure relates to isolated binding agents that bind to JAML or JAML D1 comprising the sequence IGIIHPG (SEQ ID NO:51) further optionally comprising the sequence YGS (SEQ ID NO:29).

In certain embodiments, the disclosure relates to isolated binding agents that bind to JAML or JAML D1 comprising the sequence IGIIHP (SEQ ID NO:52) further optionally comprising the sequence YGS (SEQ ID NO:29).

In certain embodiments, the disclosure relates to isolated binding agents that bind to JAML or JAML D1 comprising the sequence GIIHPG (SEQ ID NO:53) further optionally comprising the sequence YGS (SEQ ID NO:29).

In certain embodiments, the disclosure relates to isolated binding agents that bind to JAML or JAML D1 comprising the sequence GIIHP (SEQ ID NO:54) further optionally comprising the sequence YGS (SEQ ID NO:29).

In certain embodiments, the disclosure relates to isolated binding agents that bind to JAML or JAML D1 comprising the sequence PGSGGTVYNH (SEQ ID NO:55) further optionally comprising the sequence YGS (SEQ ID NO:29).

In certain embodiments, the disclosure relates to isolated binding agents that bind to JAML or JAML D1 comprising the sequence GSGGTVYNH (SEQ ID NO:56) further optionally comprising the sequence YGS (SEQ ID NO:29).

In certain embodiments, the disclosure relates to isolated binding agents that bind to JAML or JAML D1 comprising the sequence SGGTVYNH (SEQ ID NO:57) further optionally comprising the sequence YGS (SEQ ID NO:29).

In certain embodiments, the disclosure relates to isolated binding agents that bind to JAML or JAML D1 comprising the sequence GGTVYNH (SEQ ID NO:58) further optionally comprising the sequence YGS (SEQ ID NO:29).

In certain embodiments, the disclosure relates to isolated binding agents that bind to JAML or JAML D1 comprising the sequence RASENIYY (SEQ ID NO:59) further optionally comprising the sequence NANSLEDGVP (SEQ ID NO:60).

In certain embodiments, the disclosure relates to isolated binding agents that bind to JAML or JAML D1 comprising the sequence RASENIY (SEQ ID NO:61) further optionally comprising the sequence NANSLEDGVP (SEQ ID NO:60).

In certain embodiments, the disclosure relates to isolated binding agents that bind to JAML or JAML D1 comprising the sequence RASENIY (SEQ ID NO:61) further optionally comprising the sequence NANSLEDGVP (SEQ ID NO:60).

In certain embodiments, the disclosure relates to isolated binding agents that bind to JAML or JAML D1 comprising the sequence RASENI (SEQ ID NO:63) further optionally comprising the sequence NANSLEDGVP (SEQ ID NO:60).

In certain embodiments, the disclosure relates to isolated binding agents that bind to JAML or JAML D1 comprising the sequence RASEN (SEQ ID NO:64) further optionally comprising the sequence NANSLEDGVP (SEQ ID NO:60).

In certain embodiments, the disclosure relates to isolated binding agents that bind to JAML or JAML D1 comprising the sequence RASENIY (SEQ ID NO:61) further optionally comprising the sequence ANSLEDGVP (SEQ ID NO:65).

In certain embodiments, the disclosure relates to isolated binding agents that bind to JAML or JAML D1 comprising the sequence RASENIY (SEQ ID NO:61) further optionally comprising the sequence NSLEDGVP (SEQ ID NO:66).

A specific embodiment of the disclosure relates to peptibodies that bind JAML or JAML D1 such as a H1, H2, H3, and/or L1, L2, L3 alone or in combination that can be fused with human Fc Ig. Other embodiments of the disclosure include the peptide portion of these fusions as well as similar JAML or JAML D1 binding peptides that can be made by addition, deletion, and/or insertion of amino acids to and from the peptide. Similar additions, deletions, or insertions can be made to the Fc portion of the peptibody. Further alterations to peptibodies in general are well-known in the art and taught in, for example, WO00/24782 and WO03/057134 which are incorporated herein by reference to the sections which describe and teach making binding agents that contain a randomly generated peptide which binds a desired target.

In certain embodiments, the disclosure relates to pharmaceutical composition comprising binding agents described herein such as antibodies and a pharmaceutically acceptable excipient, dilutant, or carrier. Such a medicinal product may be used in methods of treating or preventing an inflammatory disease, skin inflammatory diseases, eye inflammatory diseases, autoimmune disease, cancer, viral infection, or scaring by administering an effective amount to a subject in need thereof. The inflammatory disease may be atherosclerosis, and ischemic heart disease, acne vulgaris, asthma, bronchitis, chronic prostatitis, hypersensitivities, inflammatory bowel diseases, pelvic inflammatory disease, reperfusion injury, or transplant rejection of a kidney, liver, or pancreas. The autoimmune disease may be rheumatoid arthritis, amyotrophic lateral sclerosis, Crohn's disease, type 1 diabetes, psoriasis, sarcoidosis, interstitial cystitis, glomerulonephritis, vasculitis, and ulcerative colitis. The subject may be in need thereof because the subject is diagnosed with, at risk of, or exhibiting symptoms of an inflammatory disease, autoimmune disease, respiratory disease, heart disease, myocardial infarction, viral infection, or cancer.

In certain embodiments, the disclosure contemplates modulating barrier functions and permeability such as in drug delivery and vaccines. In certain embodiments, the disclosure contemplates administering effective amounts of binding agents and antibodies disclosed herein to a subject in need thereof in combination with therapeutic agents and vaccines. In certain embodiments, binding agents and antibodies disclosed herein may be used to increase permeability by enhancing barrier when soluble JAML is present by binding to JAML and allowing CAR to seal the epithelium. CAR is in the heart and JAML released by PMN in a heart attack may compromise cardiomyocyte function by binding to CAR. In certain embodiments, the disclosure relates to administering a binding agent or antibody disclosed herein to a subject at risk of, diagnosed with, or exhibiting symptoms or a heart attack or cardiovascular disease to promote cardiac healing.

In certain embodiments, the disclosure contemplates uses of binding agents and antibodies disclosed herein for detecting soluble JAML in samples, e.g., body fluids, as an indication of leukocyte activation and/or transmigration. Detection of JAML cleavage or degradation is also contemplated.

The disclosure further relates to a hybridoma that produces a monoclonal antibody according to the disclosure, as well as a cell lines containing (through any means such as by transfection, transformation, electroporation) with the nucleic acid sequences necessary to express the present specific binding agents such as the antibodies described herein.

It will also be appreciated that the disclosure relates to conjugates as described herein. The conjugate can be, for example, a specific binding agent (such as an antibody) of the disclosure conjugated to other proteinatious, carbohydrate, lipid, or mixed moiety molecule(s).

The disclosure further relates to nucleic acid molecules encoding the specific binding agents (such as an antibody) of the disclosure or any sequences disclosed herein, as well as a vector comprising such nucleic acid molecule, as well as a host cell containing the vector.

Additionally, the disclosure provides a method of making a specific binding agent comprising, (a) transforming a host cell with at least one nucleic acid molecule encoding the specific binding agent; (b) expressing the nucleic acid molecule in said host cell; and (c) isolating said specific binding agent. The disclosure further provides a method of making an antibody comprising: (a) transforming a host cell with at least one nucleic acid molecule encoding the antibody as disclosed herein; (b) expressing the nucleic acid molecule in said host cell; and (c) isolating said specific binding agent.

The disclosure also provides a specific binding agent comprising heavy or light chain complementarity determining region 1 (CDR 1) of any of the antibodies disclosed herein and antigen binding fragments thereof. The disclosure further relates to a specific binding agent comprising heavy or light chain complementarity determining region 2 (CDR 2) of any of the antibodies disclosed herein and antigen binding fragments thereof. The disclosure also relates to a specific binding agent comprising heavy or light chain complementarity determining region 3 (CDR 3) of any of the antibodies disclosed herein and antigen binding fragments thereof.

Other embodiments of the disclosure include isolated nucleic acid molecules encoding any of the antibodies described herein, vectors having isolated nucleic acid molecules encoding anti-JAML and/or anti-JAML D1 antibodies or a host cell transformed with any of such nucleic acid molecules. In addition, one embodiment of the disclosure relates to a method of producing an anti-JAML and/or anti-JAML D1 antibody by culturing host cells under conditions wherein a nucleic acid molecule is expressed to produce the antibody followed by recovering the antibody. It should be realized that embodiments of the disclosure also include any nucleic acid molecule which encodes an antibody or fragment of an antibody or unsubstantial mutation or conservative substitution of the disclosure including nucleic acid sequences optimized for increasing yields of antibodies or fragments thereof when transfected into host cells for antibody production.

A further embodiment herein includes a method of producing high affinity antibodies to anti-JAML and/or anti-JAML D1 by immunizing a mammal with human JAML or JAML D1, or a fragment thereof, and one or more orthologous sequences or fragments thereof.

Moreover, the disclosure relates to a method of detecting the level JAML or JAML D1 in a biological sample by (a) contacting a specific binding agent of the disclosure with the sample; and (b) determining the extent of binding of the specific binding agent to the sample The disclosure also relates to a method of inhibiting undesired inflammation in a mammal comprising administering a therapeutically effective amount of a polypeptide or composition as described herein. The disclosure also relates to a method of modulating inflammation in a mammal comprising administering a therapeutically effective amount of a polypeptide or composition as described herein.

Other methods of using the compositions of the present disclosure include a method of modulating or inhibiting JAML or CAR activity comprising administering to a patient the isolated polypeptide, binding agent or antibody described herein. Such methods of modulating or inhibiting JAML or CAR activity comprise administering to a patient the polypeptide, binding agent, or antibody described herein.

Also contemplated is a combination therapy as a method of treating conditions or diseases disclosed herein in a mammal comprising administering a therapeutically effective amount of an isolated polypeptide, binding agent or antibody described herein and a second therapeutic agent.

BRIEF DESCRIPTION OF THE FIGURES

FIG. 5B. Results obtained with HL60 were confirmed with PLB985 showing inhibition of shedding with Phenanthroline and TAPI-2 1 μM, also an inhibitor of $Zn^{++}$ metalloproteases.

FIG. 5C. Inhibition of JAML shedding on the cell surface of PLB985 was confirmed by FACS analysis of cells stained with DW216. In the presence of inhibitors, activated cells maintained the same level of surface expression as the non-activated cells.

FIG. 13A shows colonic mucosal wounds generated using a mouse colonscope.

FIG. 13B shows data indicating ligation of CAR at the JAML binding site delays colonic mucosal wound healing in-vivo. In-vitro data indicates that CAR is involved in the regulation of epithelial wound healing, and that JAML binding to CAR inhibits CAR mediated regulation of wound healing. To examine this in-vivo, the effect of inhibition of CAR function was analyzed on mucosal wound recovery. The adenoviral fiber knob protein Ad5 but not Ad11 has been reported to bind murine CAR and compete with JAML binding. See Witherden et al., Science, 2010, 329(5996): 1205-1210. Whether administration of recombinant Ad5 inhibits colonic wound healing was examined in mice in a fashion analogous to the endogenous CAR ligand, JAML. Colonic mucosal wounds were generated using a mouse colonoscope, and wound recovery was examined 2 and 4 days post wounding by endoscopic imaging in the presence of Ad5, Ad11 (administered I.P, twice a day 10 µg in 200 µl PBS) or PBS alone. Ad5 but not Ad11 or PBS treatment resulted in significantly delayed mucosal wound healing 4 days after wounding (~20% vs. 76 and 83% respectively).

FIG. 13D shows representative images. The delayed wound closure was also evident from histological analysis.

FIG. 13D shows representative images of whole mount preparation.

FIG. 13E shows co-localization of CAR and His tag in yellow box. Using immunofluorescence labeling of wounded mouse colonic tissue (1 day after wounding) we confirmed that I.P. administered his-tagged Ad5 but not his tagged Ad11 colocalizes with epithelial CAR at wounded areas.

DETAILED DESCRIPTION

Figure 1A:
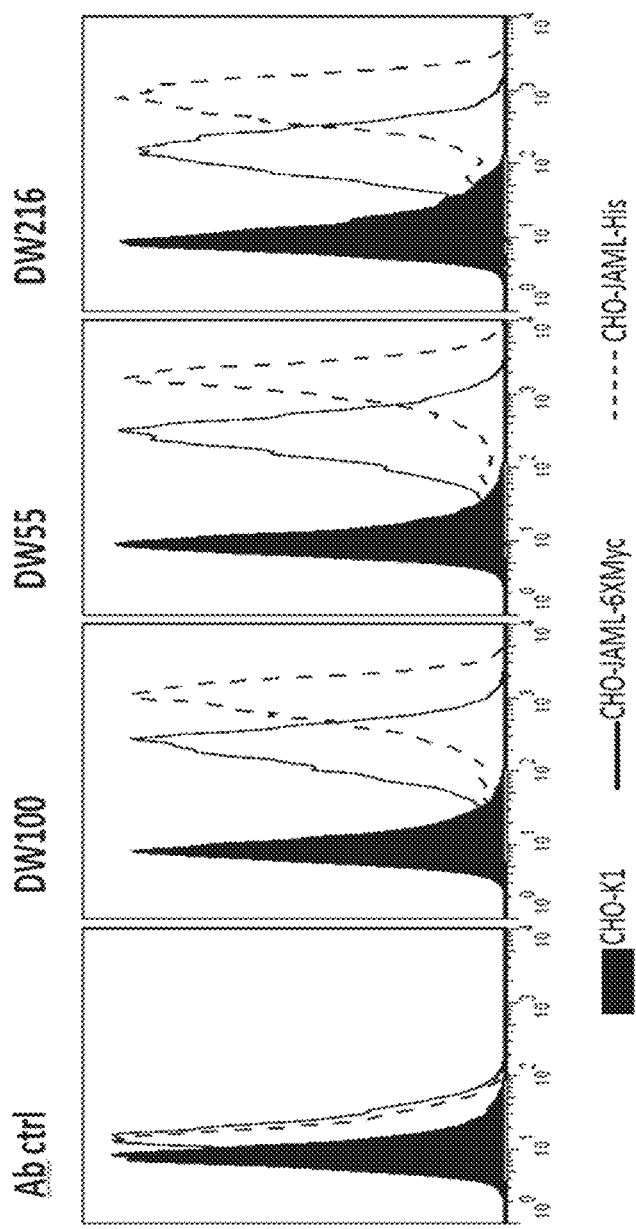
FIG. 1A shows data suggesting DW100 binds the D1 domain of JAML and DW100 and DW55 inhibit human JAML binding with CAR._BALB/c mice were immunized with recombinant soluble fragment of JAML.D1D2 tagged with 10 His residues at the C-terminus (sJAML-His), generated in H293T cells and purified by Nickel chromatography. After the 4$^{th}$ boost, mice were given a final immunization and, 3 days later, spleen cells harvested and fused to the myeloma cell line P3U1. Hybridomas were selected in HAT medium and supernatants of clones were subjected to screening first to immobilized, soluble JAML and followed by staining of CHO-JAML stable transfectants. Three hybridomas were selected and antibodies were purified from ascites. FACS staining profiles of mAbs using two different, stably transfected CHO-JAML cell lines, CHO-JAML-His and CHO JAML-6×Myc, both membrane bound and tagged at the C-terminus with either 10-His or 6×Myc. Control antibody is 9E10 anti Myc. As can be seen, Anti JAML antibodies strongly stain both transfectant cell lines.

Efforts at making specific antibodies against JAML extracellular domain have proved challenging. The protein is conserved from mouse to human and previously available antibodies have been found to cross react with a guanylate binding protein (GBP) and other Ig superfamily members lacking sufficient specificity to be used in studies specifically targeting JAML because they are cross reactive with multiple proteins by western blot. In an effort to obtain a specific human JAML antibody, several sequential fusions with splenic B cells were performed from mice immunized with highly purified His-tagged, eukaryotically expressed, extracellular domain of human JAML followed by intensive screening that included flow cytometric analysis of binding to CHO cells stably transfected with full-length JAML. From these extensive studies several mAbs have been produced that specifically bind to JAML but not to other JAM proteins. Importantly, one of these antibodies inhibits JAML-CAR binding in vitro. In addition, hybridoma supernatants containing these JAM-L mAbs block inhibitory effects of PMN on wound healing in epithelial monolayers.

In accordance with the Budapest Treaty, a hybridoma which produces DW100 monoclonal antibodies has been deposited in the American Type Culture Collection (ATCC) 10801 University Boulevard, Manassas, Va. 20110-2209 on Jul. 11, 2012 and Jul. 26, 2012 with a Patent Deposit Designation of PTA-13051.

JAML-CAR interactions promote PMN adhesion to epithelium. However it has been discovered that JAML is released (shed) from the PMN surface during transepithelial migration while it is retained on PMN surface during migration across endothelium. Soluble JAML that is shed from PMNs significantly impair both epithelial barrier and wound restitution. It has also been discovered that monoclonal antibodies that completely block JAML/CAR binding reverse delayed epithelial wound closure under conditions which increased JAML, such as during acute inflammation. It has been discovered that infiltrating PMNs contribute to disruption of the epithelial cell function by protease-dependent shedding of JAML from PMN surface during TEM. Shed JAML is able to bind CAR expressed at the epithelial tight junctions, and significantly impaired epithelial barrier function, and wound restitution.

JAML belongs to Ig superfamily and shares significant homology with other members, however in contrast to other members its expression is believed to be restricted to certain cells, e.g., granulocytes and subsets of T lymphocytes, but not to epithelial or endothelial cells. JAML has been described as unconventional immunoglobulin-domain receptor due to the more rigid assembly of its Ig domains and an extended, flexible stalk which allows its interaction with CAR on the cell surface of an adjacent cell. Human JAML-CAR binding occurs at the interface of membrane distal D1 domains of both JAML and CAR, and can be blocked with DW100 mAb, which specifically binds JAML D1 domain as shown in FIG. 1. DW 100 is the first mAb that has been demonstrated to specifically block JAML-CAR binding. It is used to study the functional consequences of JAML shedding.

When examining the expression of JAML on PMN surface, a complete loss of JAML was observed on PMNs that underwent TEM (FIG. 3). Zen et al., Mol. Biol. Cell, 2005, 16(6) 2694-2703), described an upregulation of JAML in activated PMNs. However, cells were labeled with a polyclonal antiserum and against recombinant JAM-L which likely cross reacted with other protein(s). Polyclonal antibodies raised against JAML cross-reacted with other JAM proteins or other Ig super family members.

For example, in the fusion that produced the antibodies described herein, four hybridomas showed strong positive reactivity to JAML. These were subcloned, and the secreted antibodies further investigated. Three antibodies DW100 (IgG1,κ), DW55 (IgG2b,κ) and DW216 (IgG1,κ) stained both transfectant lines equally well as seen in FIG. 1A. Interestingly, the fourth hybridoma produced antibodies that strongly labeled CHO-JAMA transfectants as well as CHO-JAML transfectants. Such cross-reactivity highlighted a problem with antigen specificity in using polyclonal antisera raised against JAML in other studies.

Three different monoclonal antibodies with specificities towards JAML are provided herein. Whether tested in ELISA assay using purified recombinant sJAML and sCAR molecules or tested in a cellular system where JAML and CAR are both expressed at the surface of CHO cells, DW100 completely inhibited JAML/CAR interactions and significantly inhibited aggregation of mixed cultures of CHO transfectants, whereas DW216 did not. DW55 was partly inhibitory and suggested that its epitope on JAML was close to the binding site for CAR. The size of the ligands was identified by biotinylation of the cells and immunoprecipitation. The blots revealed bands at ~60 KD, suggesting a high degree of glycosylation. Interestingly, the same antibodies precipitated a protein from CHO-JAML transfectants that runs as a smaller protein on SDS-PAGE gels and that could be isoforms of JAML or truncated JAML.

Figure 11:
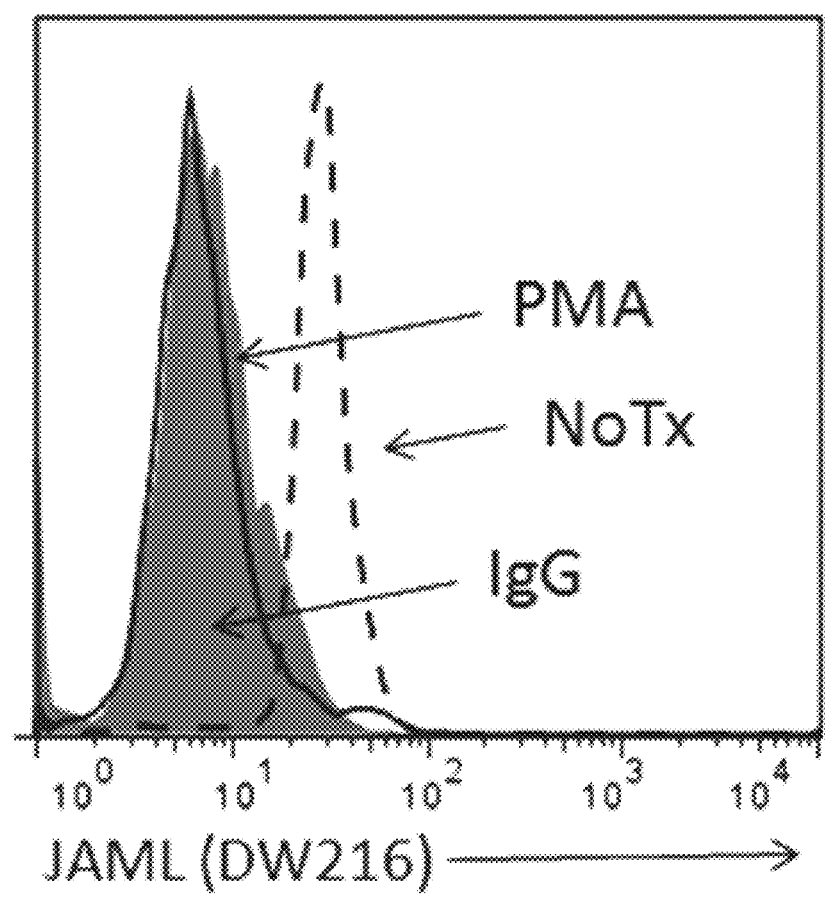
FIG. 11 shows data suggesting monocytes shed JAML upon activation with PMA. Monocytes were isolated and purified from whole blood of healthy human donors, incubated on ice with either IgG control (solid histograms) or purified anti-JAML antibodies (5 µg/ml), followed by Alexa Fluor 488 conjugated goat anti mouse antibody before (NoTx) and after PMA activation (PMA, 15 minutes at 37° C.). JAML surface expression was analyzed by flow cytometry.

Following the observation of a complete loss of JAML on PMNs that underwent TEM and with the use of JAML specific mAbs, it was determined that the loss of JAML was induced by PMN activation and that it correlated to the degree of activation and the strength of the given stimulus. Phorbol myristate acetate (PMA), a more potent activator compared to fMLF, induced a significantly greater loss of JAML from PMN surface (FIG. 4). Interestingly, JAML expression inversely paralleled an increase in the expression of CD11b/CD18 in response to these different stimuli, thus allowed us to monitor the level of CD11b/CD18 expression to determine the activation state of PMNs. Given these findings, our data suggesting that PMNs undergo activation during TEM, and this activation is equivalent of a treatment with 200 nM PMA. Importantly, data suggest that JAML shedding occurs in part upon initial PMN adhesion to the basal epithelial surface, and continues throughout PMN TEM, thus soluble JAML could be localized to both basal and apical sides of the epithelial layer. JAML shedding is not restricted to PMNs alone. JAML is also expressed on blood monocytes. JAML expression on monocytes was found to be higher than that on PMNs and was also lost upon activation with PMA (FIG. 11). As monocytes trail the PMNs infiltrating mucosal surfaces, in addition to PMNs they would also be a source for soluble JAML, further enhancing its effects on epithelial function. Furthermore, data suggest that the loss of JAML is not due to the physical interaction with CAR, as PMN that migrated across endothelial cells (HDM-VECs, FIG. 3), which express CAR retained JAML on the cell surface. The shedding of JAML is believed to be due to a zinc-dependent metalloprotease that is inhibited by phenanthroline, a zinc chelator molecule and TAPI-2, a hydroxymate acid-base derivative which inhibits zinc-dependent metalloprotease activities by binding specifically to the catalytic site of the enzyme.

Soluble JAML delayed both epithelial barrier recovery and wound restitution (FIGS. 9, 10). While there are a few possible ways to explain these effects, one likely mechanism would involve JAML binding to epithelial CAR, and interfering with its function. In polarized epithelial cell lines, CAR is expressed at the apical pole of the lateral membrane, where it colocalizes with the cytoplasmic plaque TJ protein zonula occludens-1 (ZO-1). CAR is mainly recognized as the receptor that mediates viral attachment, however it has been also implicated in regulating epithelial permeability and affecting cancer progression in malignancies. CAR has been shown to dimerize in cis, as well as suggested to bind in trans, thus mediating hemophilic binding interaction. In both recombinant protein binding assays, as well as aggregation of CHO cells that stably express CAR (FIG. 1), CAR-CAR binding as well as any aggregation of CHO-CAR transfectants failed. As CAR dimerization occurs at the membrane distal D1 domain, which is also the binding domain for JAML, it is possible that JAML binding would prevent CAR dimerization and thus decrease its signaling ability and function. Binding and aggregation was not observed between CAR molecules in the absence of JAML.

Furthermore, given JAML structure and the fact that it contains a motif (KID58 flanked by Y72), which is similar to that of JAM-A dimerization site, JAML might also be able to dimerize. While recombinant protein binding assays failed to demonstrate JAML-JAML homophilic interactions, cell aggregation assay (FIG. 1) suggested that it is indeed possible. CHO cells stably expressing JAML formed significant number of aggregates, specific to JAML-JAML interactions, and it could not be blocked with DW100 mAb (FIG. 1). JAML that is shed from transmigrating PMNs might bind to $\gamma\delta$ T-cells that have been attracted to the wound and promote their activation, or alternatively prevent their activation and the ensuing anti-inflammatory effects by interfering with their binding to CAR. Thus soluble JAML that is shed from transmigrating PMNs can potentially act both on the basal and the apical sides of the epithelium. As CAR mediates attachment of invading viruses, the shedding of JAML by migrating PMNs might be an additional mechanism to protect against viral infections.

PMNs infiltrating the mucosal surface shed surface JAML, which impairs epithelial function likely by binding to CAR. DW100 is a specific monoclonal antibody that could reduce the level of epithelial damage by blocking the interaction between CAR and JAML.

Specific Binding Agents and Antibodies

Suitable specific binding agents may be prepared using methods known in the art. An exemplary JAML and JAML D1 polypeptide specific binding agent of the present disclosure is capable of binding a certain portion of the JAML and JAML D1 polypeptides, and preferably modulating the activity or function of JAML and JAML D1 polypeptides. Specific binding agents such as antibodies and antibody fragments that specifically bind JAML polypeptides are within the scope of the present disclosure. The antibodies may be polyclonal including mono-specific polyclonal, monoclonal (mAbs), recombinant, chimeric, humanized such as CDR-grafted, human, single chain, catalytic, multi-specific and/or bi-specific, as well as antigen-binding fragments, variants, and/or derivatives thereof.

Once a polynucleotide sequences are identified which encode each chain of the full length monoclonal antibody or the Fab or Fv fragment(s) of the disclosure, host cells, either eukaryotic or prokaryotic, may be used to express the monoclonal antibody polynucleotides using recombinant techniques well known and routinely practiced in the art. Alternatively, transgenic animals are produced wherein a polynucleotide encoding the desired specific binding agent is introduced into the genome of a recipient animal, such as, for example, a mouse, rabbit, goat, or cow, in a manner that permits expression of the polynucleotide molecules encoding a monoclonal antibody or other specific binding agent. In one aspect, the polynucleotides encoding the monoclonal antibody or other specific binding agent can be ligated to mammary-specific regulatory sequences, and the chimeric polynucleotides can be introduced into the germline of the target animal. The resulting transgenic animal then produces the desired antibody in its milk [Pollock et al., J Immunol Meth 231:147-157 (1999); Little et al., Immunol Today 8:364-370 (2000)]. In addition, plants may be used to express and produce JAML or JAML D1 specific binding agents such as monoclonal antibodies by transfecting suitable plants with the polynucleotides encoding the monoclonal antibodies or other specific binding agents.

In another embodiment of the present disclosure, a monoclonal or polyclonal antibody or fragment thereof that is derived from other than a human species may be "humanized" or "chimerized". Methods for humanizing non-human antibodies are well known in the art. (see U.S. Pat. Nos. 5,859,205, 5,585,089, and 5,693,762). Humanization is performed, for example, using methods described in the art [Jones et al., Nature, 321: 522-525 (1986); Riechmann et al., Nature, 332: 323-327 (1988); Verhoeyen et al., Science, 239:1534-1536 (1988)] by substituting at least a portion of, for example a rodent, complementarity-determining region (CDRs) for the corresponding regions of a human antibody. The disclosure also provides variants and derivatives of these human antibodies as discussed herein and well known in the art.

Also encompassed by the disclosure are fully human antibodies that bind JAML or JAML D1 polypeptides, as well as, antigen-binding fragments, variants and/or derivatives thereof. Alternatively, transgenic animals (e.g., mice) that are capable of producing a repertoire of human antibodies in the absence of endogenous immunoglobulin production can be used to generate such antibodies. This can be accomplished by immunization of the animal with an JAML or JAML D1 antigen or fragments thereof where the JAML or JAML D1 fragments have an amino acid sequence that is unique to JAML or JAML D1. Such immunogens can be optionally conjugated to a carrier. See, for example, Jakobovits et al., Proc Natl Acad Sci (USA), 90: 2551-2555 (1993); Jakobovits et al., Nature 362: 255-258 (1993); Bruggermann et al., Year in Immuno, 7: 33 (1993). In one method, such transgenic animals are produced by incapacitating the endogenous loci encoding the heavy and light immunoglobulin chains therein, and inserting loci encoding human heavy and light chain proteins into the genome thereof. Partially modified animals, that are those having less than the full complement of these modifications, are then crossbred to obtain an animal having all of the desired immune system modifications. When administered an immunogen, these transgenic animals are capable of producing antibodies with human variable regions, including human (rather than e.g., murine) amino acid sequences, that are immuno-specific for the desired antigens. See PCT application Nos., PCT/US96/05928 and PCT/US93/06926. Additional methods are described in U.S. Pat. No. 5,545,807, PCT application Nos. PCT/US91/245, PCT/GB89/01207, and in EP 546073B1 and EP 546073A1. Human antibodies may also be produced by the expression of recombinant DNA in host cells or by expression in hybridoma cells as described herein.

Transgenesis is achieved in a number of different ways. See, for example, Bruggeman et al., Immunol Today 17:391-7 (1996). In one approach, a minilocus is constructed such that gene segments in a germline configuration are brought artificially close to each other. Due to size limitations (i.e., having generally less than 30 kb), the resulting minilocus will contain a limited number of differing gene segments, but is still capable of producing a large repertoire of antibodies. Miniloci containing only human DNA sequences, including promoters and enhancers are fully functional in the transgenic mouse.

When larger number of gene segments are desired in the transgenic animal, yeast artificial chromosomes (YACs) are utilized. YACs can range from several hundred kilobases to 1 Mb and are introduced into the mouse (or other appropriate animal) genome via microinjection directly into an egg or via transfer of the YAC into embryonic stem (ES)-cell lines. In general, YACs are transferred into ES cells by lipofection of the purified DNA, or yeast spheroplast fusion wherein the purified DNA is carried in micelles and fusion is carried out in manner similar to hybridoma fusion protocols. Selection of desired ES cells following DNA transfer is accomplished by including on the YAC any of the selectable markers known in the art.

As another alternative, bacteriophage P1 vectors are used which are amplified in a bacterial E. coli host. While these vectors generally carry less inserted DNA than a YAC, the clones are readily grown in high enough yield to permit direct microinjection into a mouse egg. Use of a cocktail of different P1 vectors has been shown to lead to high levels of homologous recombination.

Once an appropriate transgenic mouse (or other appropriate animal) has been identified, using any of the techniques known in the art to detect serum levels of a circulating antibody (e.g., ELISA), the transgenic animal is crossed with a mouse in which the endogenous Ig locus has been disrupted. The result provides progeny wherein essentially all B cells express human antibodies.

As still another alternative, the entire animal Ig locus is replaced with the human Ig locus, wherein the resulting animal expresses only human antibodies. In another approach, portions of the animal's locus are replaced with specific and corresponding regions in the human locus. In certain cases, the animals resulting from this procedure may express chimeric antibodies, as opposed to fully human antibodies, depending on the nature of the replacement in the mouse Ig locus.

Human antibodies can also be produced by exposing human splenocytes (B or T cells) to an antigen in vitro, then reconstituting the exposed cells in an immunocompromised mouse, e.g. SCID or nod/SCID. See Brams et al., J Immunol, 160: 2051-2058 [1998]; Carballido et al., Nat Med, 6: 103-106 [2000]. In one approach, engraftment of human fetal tissue into SCID mice (SCID-hu) results in long-term hematopoiesis and human T-cell development [McCune et al., Science 241:1532-1639 (1988); Ifversen et al., Sem Immunol 8:243-248 (1996)]. Any humoral immune response in these chimeric mice is completely dependent on co-development of T-cells in the animals [Martensson et al., Immunol 83:1271-179 (1994)]. In an alternative approach, human peripheral blood lymphocytes are transplanted intraperitoneally (or otherwise) into SCID mice [Mosier et al., Nature 335:256-259 (1988)]. When the transplanted cells are treated with either a priming agent, such as Staphylococcal Enterotoxin A (SEA) [Martensson et al., Immunol 84: 224-230 (1995)], or anti-human CD40 monoclonal antibodies [Murphy et al., Blood 86:1946-1953 (1995)], higher levels of B cell production are detected.

Alternatively, an entirely synthetic human heavy chain repertoire is created from unrearranged V gene segments by assembling each human VH segment with D segments of random nucleotides together with a human J segment [Hoogenboom et al., J Mol Biol 227:381-388 (1992)]. Likewise, a light chain repertoire is constructed by combining each human V segment with a J segment [Griffiths et al., EMBO J. 13:3245-3260 (1994)]. Nucleotides encoding the complete antibody (i.e., both heavy and light chains) are linked as a single chain Fv fragment and this polynucleotide is ligated to a nucleotide encoding a filamentous phage minor coat protein. When this fusion protein is expressed on the surface of the phage, a polynucleotide encoding a specific antibody is identified by selection using an immobilized antigen.

In still another approach, antibody fragments are assembled as two Fab fragments by fusion of one chain to a phage protein and secretion of the other into bacterial periplasm [Hoogenboom et al., Nucl Acids Res 19:4133-4137 [1991]; Barbas et al., Proc Natl Acad Sci (USA) 88:7978-7982 (1991)].

Large-scale production of chimeric, humanized, CDR-grafted, and fully human antibodies, or antigen-binding fragments thereof, are typically produced by recombinant methods. Polynucleotide molecule(s) encoding the heavy and light chains of each antibody or antigen-binding fragments thereof, can be introduced into host cells and expressed using materials and procedures described herein. In a preferred embodiment, the antibodies are produced in mammalian host cells, such as CHO cells.

The specific binding agents of the present disclosure, such as the antibodies, antibody fragments, and antibody derivatives of the disclosure can further comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutant of a naturally occurring constant region.

In one embodiment, the specific binding agents of the present disclosure, such as the antibodies, antibody fragments, and antibody derivatives of the disclosure comprise an IgG.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16. The specific binding agents of the present disclosure, such as the antibodies, antibody fragments, and antibody derivatives of the disclosure may comprise the IgG1 heavy chain constant domain or a fragment of the IgG1 heavy chain domain. The antibodies, antibody fragments, and antibody derivatives of the disclosure may further comprise the constant light chain kappa or lambda domains or a fragment of these. Light chain constant regions and polynucleotides encoding them are provided herein below. In another embodiment, the antibodies, antibody fragments, and antibody derivatives of the disclosure further comprise a heavy chain constant domain, or a fragment thereof, such as the IgG2 heavy chain constant region also shown herein below.

The nucleic acid (DNA) encoding constant heavy and constant light chain domains, and the amino acids sequences of heavy and light chain domains are provided herein below.

Lambda variable domains can be fused to lambda constant domains and kappa variable domains can be fused to kappa constant domains.

```
IgG2 Heavy Constant domain DNA
                                      (SEQ ID NO: 69)
GCTAGCACCAAGGGCCCATCGGTCTTCCCCCTGGCGCCCTGCTCCAGGAG

CACCTCCGAGAGCACAGCGGCCCTGGGCTGCCTGGTCAAGGACTACTTCC

CCGAACCGGTGACGGTGTCGTGGAACTCAGGCGCTCTGACCAGCGGCGTG

CACACCTTCCCAGCTGTCCTACAGTCCTCAGGACTCTACTCCCTCAGCAG

CGTGGTGACCGTGCCCTCCAGCAACTTCGGCACCCAGACCTACACCTGCA

A CGTAGATCACAAGCCCAGCAACACCAAGGTGGACAAGACAGTTGAGCG

CAAATGTTGTGTCGAGTGCCCACCGTGCCCAGCACCACCTGTGGCAGGAC

CGTCAGTCTTCCTCTTCCCCCCAAAACCCAAGGACACCCTCATGATCTCC

CGGACCCCTGAGGTCACGTG CGTGGTGGTGGACGTGAGCCACGAAGACC

CCGAGGTCCAGTTCAACTGGTACGTGGACGGCGTGGAGGTGCATAATGCC

AAG ACAAAGCCACGGGAGGAGCAGTTCAACAGCACGTTCCGTGTGGTCA

GCGTCCTCACCGTTGTGCACCAGGACTGGCTGAACGGCAAGGAGTACAAG

TGCAAGGTCTCCAACAAAGGCCTCCCAGCCCCCATCGAGAAAACCATCTC

CAAAACCAAAGGGCAGCCC CGAGAACCACAGGTGTACACCCTGCCCCCA

TCCCGGGAGGAGATGACCAAGAACCAGGTCAGCCTGACCTGCCTGGTCAA

AG GCTTCTACCCCAGCGACATCGCCGTGGAGTGGGAGAGCAATGGGCAG

CCGGAGAACAACTACAAGACCACACCT CCCATGCTGGACTCCGACGGCT

CCTTCTTCCTCTACAGCAAGCTCACCGTGGACAAGAGCAGGTGGCAGCAG

GGGAACGTCTTCTCATGCTC CGTGATGCATGAGGCTCTGCACA ACCAC

TACACGCAGAAGAGCCTCTCCCTGTCTCCGGGTAAATGA

IgG2 Heavy Constant domain Protein
                                      (SEQ ID NO: 70)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

Kappa Light Constant domain DNA
                                      (SEQ ID NO: 71)
CGTACGGTGGCTGCACCATCTGTCTTCATCTTCCCGCCATCTGATGAGCA

GTTGAAATCTGGAACTGCCTCTGTTGTGTGCCTGCTGA ATAACTTCTAT

CCCAGAGAGGCCAAAGTACAGTGGAAGGTGGATAACGCCCTCCAATCGGG

TAACTCCCAGGAGAGTGTCACAG AGCAGGACAGCAAGGACAGCACCTAC

AGCCTCAGCAGCACCCTGACGCTGAGCAAAGCAGACTACGAGAAACACAA

AGTCT ACGCCTGCGAAGTCACCCATCAGGGCCTGAGCTCGCCCGTCACA

AAGAGCTTCAACAGGGGAGAGTGTTAG

Kappa Light Constant domain Protein
                                      (SEQ ID NO: 72)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

Lambda Light Constant domain DNA
                                      (SEQ ID NO: 73)
GGCCAACCGAAAGCGGCGCCCTCGGTCACTCTGTTCCCGCCCTCCTCTGA

GGAGCTTCAAGCCAACAAGGCCACACTGGTGTGT CTCATAAGTGACTTC

TACCCGGGAGCCGTGACAGTGGCCTGGAAGGCAGATAGCAGCCCCGTCAA

GGCGGGAGTGGAGACCA CCACACCCTCCAAACAAAGCAACAACAAGTAC

GCGGCCAGCAGCTATCTGAGCCTGACGCCTGAGCAGTGGAAGTCCCACAG

AAGCTACAGCTGCCAGGTCACGCATGAAGGGAGCACCGTGGAGAAGACAG

TGGCCCCTACAGAATGTTCATAG

Lambda Light Constant domain Protein
                                      (SEQ ID NO: 74)
GQPKAAPSVTLFPPSSEELQANKATLVCLISDFYPGAVTVAWKADSSPVK

AGVETTTPSKQSNNKYAASSYLSLTPEQWKSHRSYSCQVTHEGSTVEKTV

APTECS
```

The specific binding agents of the present disclosure, such as the antibodies, antibody fragments, and antibody derivatives of the disclosure include those comprising, for example, the variable domain combinations H1L1, H2L2, H3L3 having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation in the hinge region as described in Bloom et al., 1997, Protein Science 6:407 (incorporated by reference herein) to alleviate a tendency to form intra-H chain disulfide bonds that can lead to heterogeneity in the IgG4 antibodies.

Additional Useful Sequence Information

The following sequences of the IgG1, IgG2, IgG3, and IgG4 isotypes are used in combination with the variable heavy chain sequences of the antibodies of the present disclosure to make a specific desired isotype of said antibody:

```
Human IgG1
                                      (SEQ ID NO: 75)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human IgG2
                                      (SEQ ID NO: 76)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP
```

-continued
EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDLAVEWESNGQPENNYKTTPPMLDSDGSFFLYSKLTVDKSRWQQGN

VFSCSVMHEALHNHYTQKSLSLSPGK

Human IgG3
(SEQ ID NO: 83)
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK

Human IgG4
(SEQ ID NO: 77)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

Fusion Partners of Specific Binding Agents

In a further embodiment of the disclosure, the polypeptides comprising the amino acid sequence variable domains of JAML or JAML D1 antibodies, such as a heavy chain variable region with an amino acid sequence as described herein or a light chain variable region with an amino acid sequence as described herein, may be fused at either the N-terminus or the C-terminus to one or more domains of an Fc region of human IgG. When constructed together with a therapeutic protein such as the Fab of a JAML or JAML D1-specific antibody, an Fc domain can provide longer half-life or incorporate such functions as Fc receptor binding, Protein A binding, complement fixation and perhaps even placental transfer. [Capon et al., Nature, 337: 525-531 (1989)].

In one example, the antibody hinge, CH2 and CH3 regions may be fused at either the N-terminus or C-terminus of the specific binding agent polypeptides such as an anti-JAML or JAML D1 Fab or Fv fragment using methods known to the skilled artisan. The resulting fusion protein may be purified by use of a Protein A or Protein G affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, decrease aggregation problems, etc. Other examples known in the art include those wherein the Fc region, which may be human or another species, or may be synthetic, is fused to the N-terminus of CD30L to treat Hodgkin's disease, anaplastic lymphoma and T-cell leukemia (U.S. Pat. No. 5,480,981), the Fc region is fused to the TNF receptor to treat septic shock [Fisher et al., N Engl J Med, 334: 1697-1702 (1996)], and the Fc region is fused to the Cd4 receptor to treat AIDS [Capon et al., Nature, 337: 525-31 (1989)].

Catalytic antibodies are another type of fusion molecule and include antibodies to which one or more cytotoxic, or more generally one or more biologically active, moieties are attached to the specific binding agent. See, for example Rader et al., Chem Eur J 12:2091-2095 (2000). Cytotoxic agents of this type improve antibody-mediated cytotoxicity, and include such moieties as cytokines that directly or indirectly stimulate cell death, radioisotopes, chemotherapeutic drugs (including prodrugs), bacterial toxins (ex. pseudomonas exotoxin, diphtheria toxin, etc.), plant toxins (ex. ricin, gelonin, etc.), chemical conjugates (e.g., maytansinoid toxins, calechaemicin, etc.), radioconjugates, enzyme conjugates (RNase conjugates, antibody-directed enzyme/prodrug therapy [ADEPT)]), and the like. In one aspect, the cytotoxic agent can be "attached" to one component of a bi-specific or multi-specific antibody by binding of this agent to one of the alternative antigen recognition sites on the antibody. As an alternative, protein cytotoxins can be expressed as fusion proteins with the specific binding agent following ligation of a polynucleotide encoding the toxin to a polynucleotide encoding the binding agent. In still another alternative, the specific binding agent can be covalently modified to include the desired cytotoxin.

Examples of such fusion proteins are immunogenic polypeptides, proteins with long circulating half-lives, such as immunoglobulin constant regions, marker proteins, proteins or polypeptides that facilitate purification of the desired specific binding agent polypeptide, and polypeptide sequences that promote formation of multimeric proteins (such as leucine zipper motifs that are useful in dimer formation/stability).

This type of insertional variant generally has all or a substantial portion of the native molecule, linked at the N- or C-terminus, to all or a portion of a second polypeptide. For example, fusion proteins typically employ leader sequences from other species to permit the recombinant expression of a protein in a heterologous host. Another useful fusion protein includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions.

There are various commercially available fusion protein expression systems that may be used in the present disclosure. Particularly useful systems include but are not limited to the glutathione-S-transferase (GST) system (Pharmacia), the maltose binding protein system (NEB, Beverley, Mass.), the FLAG system (IBI, New Haven, Conn.), and the 6×His system (Qiagen, Chatsworth, Calif.). These systems are capable of producing recombinant polypeptides bearing only a small number of additional amino acids, which are unlikely to affect the antigenic ability of the recombinant polypeptide. For example, both the FLAG system and the 6×His system add only short sequences, both of which are known to be poorly antigenic and which do not adversely affect folding of the polypeptide to its native conformation. Another N-terminal fusion that is contemplated to be useful is the fusion of a Met-Lys dipeptide at the N-terminal region of the protein or peptides. Such a fusion may produce beneficial increases in protein expression or activity.

A particularly useful fusion construct may be one in which a specific binding agent peptide is fused to a hapten to enhance immunogenicity of a specific binding agent fusion construct which is useful, for example, in the production of anti-idiotype antibodies of the disclosure. Such fusion constructs to increase immunogenicity are well known to those of skill in the art, for example, a fusion of specific binding agent with a helper antigen such as hsp70 or peptide sequences such as from diphtheria toxin chain or a cytokine such as IL-2 will be useful in eliciting an immune response. In other embodiments, fusion construct can be made which will enhance the targeting of the antigen binding agent compositions to a specific site or cell.

Other fusion constructs including heterologous polypeptides with desired properties, e.g., an Ig constant region to prolong serum half-life or an antibody or fragment thereof for targeting also are contemplated. Other fusion systems produce polypeptide hybrids where it is desirable to excise the fusion partner from the desired polypeptide. In one embodiment, the fusion partner is linked to the recombinant specific binding agent polypeptide by a peptide sequence containing a specific recognition sequence for a protease. Examples of suitable sequences are those recognized by the Tobacco Etch Virus protease (Life Technologies, Gaithersburg, Md.) or Factor Xa (New England Biolabs, Beverley, Mass.).

The disclosure also provides fusion polypeptides comprising all or part of a variable domain of an JAML or JAML D1 antibody, such as a heavy chain variable region with an amino acid sequence as described herein or a light chain variable region with an amino acid sequence as described herein in combination with truncated tissue factor (tTF), a vascular targeting agent consisting of a truncated form of a human coagulation-inducing protein that acts as a tumor blood vessel clotting agent. The fusion of tTF to the anti-JAML or JAML D1 antibody, or fragments thereof may facilitate the delivery of anti-JAML or JAML D1 to target cells.

Variants of Specific Binding Agents

Variants of Specific Binding Agents of the present disclosure include insertion, deletion, and/or substitution variants. In one aspect of the disclosure, insertion variants are provided wherein one or more amino acid residues supplement a specific binding agent amino acid sequence. Insertions may be located at either or both termini of the protein, or may be positioned within internal regions of the specific binding agent amino acid sequence. Insertional variants with additional residues at either or both termini can include, for example, fusion proteins and proteins including amino acid tags or labels. Insertion variants include specific binding agent polypeptides wherein one or more amino acid residues are added to a specific binding agent amino acid sequence, or fragment thereof.

Variant products of the disclosure also include mature specific binding agent products. Such specific binding agent products have the leader or signal sequences removed, however the resulting protein has additional amino terminal residues. The additional amino terminal residues may be derived from another protein, or may include one or more residues that are not identifiable as being derived from a specific protein. Specific binding agent products with an additional methionine residue at position-1 (Met-1-specific binding agent) are contemplated, as are specific binding agent products with additional methionine and lysine residues at positions -2 and -1 (Met.2-Lys-1-specific binding agent). Variants of specific binding agents having additional Met, Met-Lys, Lys residues (or one or more basic residues in general) are particularly useful for enhanced recombinant protein production in bacterial host cells.

The disclosure also embraces specific binding agent variants having additional amino acid residues that arise from use of specific expression systems. For example, use of commercially available vectors that express a desired polypeptide as part of glutathione-S-transferase (GST) fusion product provides the desired polypeptide having an additional glycine residue at amino acid position-1 after cleavage of the GST component from the desired polypeptide. Variants which result from expression in other vector systems are also contemplated, including those wherein poly-histidine tags are incorporated into the amino acid sequence, generally at the carboxy and/or amino terminus of the sequence.

Insertional variants also include fusion proteins as described above, wherein the amino and/or carboxy termini of the specific binding agent-polypeptide is fused to another polypeptide, a fragment thereof, or amino acid sequences which are not generally recognized to be part of any specific protein sequence.

In another aspect, the disclosure provides deletion variants wherein one or more amino acid residues in a specific binding agent polypeptide are removed. Deletions can be effected at one or both termini of the specific binding agent polypeptide, or from removal of one or more residues within the specific binding agent amino acid sequence. Deletion variants necessarily include all fragments of a specific binding agent polypeptide.

Antibody fragments include those portions of the antibody that bind to an epitope on the antigen polypeptide. Examples of such fragments include Fab and F(ab')2 fragments generated, for example, by enzymatic or chemical cleavage of full-length antibodies. Other binding fragments include those generated by recombinant DNA techniques, such as the expression of recombinant plasmids containing nucleic acid sequences encoding antibody variable regions. The disclosure also embraces polypeptide fragments of a JAML or JAML D1 binding agent wherein the fragments maintain the ability to specifically bind an JAML or JAML D1 polypeptide. Fragments comprising at least 5, 10, 15, 20, 25, 30, 35, 40, 45 or 50 or more consecutive amino acids of a peptide or polypeptide of the disclosure are comprehended herein. Preferred polypeptide fragments display immunological properties unique to or specific for the antigen-binding agent so of the disclosure. Fragments of the disclosure having the desired immunological properties can be prepared by any of the methods well known and routinely practiced in the art.

In still another aspect, the disclosure provides substitution variants of specific binding agents of the disclosure. Substitution variants are generally considered to be "similar" to the original polypeptide or to have a certain "percent identity" to the original polypeptide, and include those polypeptides wherein one or more amino acid residues of a polypeptide are removed and replaced with alternative residues. In one aspect, the substitutions are conservative in nature, however, the disclosure embraces substitutions that are also non-conservative.

Identity and similarity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., SIAM J. Applied Math., 48:1073 (1988).

Typical methods to determine the relatedness or percent identity of two polypeptides are designed to give the largest match between the sequences tested. Methods to determine identity are described in publicly available computer programs. Preferred computer program methods to determine identity between two sequences include, but are not limited to, the GCG program package, including GAP (Devereux et al., Nucl. Acid. Res., 12:387 (1984); Genetics Computer Group, University of Wisconsin, Madison, Wis., BLASTP, BLASTN, and FASTA (Altschul et al., J. Mol. Biol., 215: 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in certain embodiments, the selected alignment method (GAP program) will result in an alignment that spans at least ten percent of the full length of the target polypeptide being compared, i.e., at least 40 contiguous amino acids where sequences of at least 400 amino acids are being compared, 30 contiguous amino acids where sequences of at least 300 to about 400 amino acids are being compared, at least 20 contiguous amino acids where sequences of 200 to about 300 amino acids are being compared, and at least 10 contiguous amino acids where sequences of about 100 to 200 amino acids are being compared.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). In certain embodiments, a gap opening penalty (which is typically calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see Dayhoff et al., Atlas of Protein Sequence and Structure, 5(3)(1978) for the PAM 250 comparison matrix; Henikoff et al., Proc. Natl. Acad. Sci. USA, 89:10915-10919 (1992) for the BLOSUM 62 comparison matrix) is also used by the algorithm.

In certain embodiments, the parameters for a polypeptide sequence comparison include the following:
Algorithm: Needleman et al., J. Mol. Biol., 48:443-453 (1970);
Comparison matrix: BLOSUM 62 from Henikoff et al., supra (1992);
Gap Penalty: 12
Gap Length Penalty: 4
Threshold of Similarity: 0

The GAP program may be useful with the above parameters. In certain embodiments, the aforementioned parameters are the default parameters for polypeptide comparisons (along with no penalty for end gaps) using the GAP algorithm.

In certain embodiments, the parameters for polynucleotide molecule sequence comparisons include the following:
Algorithm: Needleman et al., supra (1970); Comparison matrix: matches=+10, mismatch=0 Gap Penalty: 50 Gap Length Penalty: 3

The GAP program may also be useful with the above parameters. The aforementioned parameters are the default parameters for polynucleotide molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

As used herein, the twenty conventional amino acids and their abbreviations follow conventional usage. See Immunology-A Synthesis (2nd Edition, E. S. Golub and D. R. Gren, Eds., Sinauer Associates, Sunderland, Mass. (1991)), which is incorporated herein by reference for any purpose.

The amino acids may have either L or D stereochemistry (except for Gly, which is neither L nor D) and the polypeptides and compositions of the present disclosure may comprise a combination of stereochemistries. However, the L stereochemistry is typical. The disclosure also provides reverse molecules wherein the amino terminal to carboxy terminal sequence of the amino acids is reversed. For example, the reverse of a molecule having the normal sequence X1-X2-X3 would be X3-X2-X1. The disclosure also provides retro-reverse molecules wherein, as above, the amino terminal to carboxy terminal sequence of amino acids is reversed and residues that are normally "L" enantiomers are altered to the "D" stereoisomer form.

Stereoisomers (e.g., D-amino acids) of the twenty conventional amino acids, unnatural amino acids such as alpha-, alpha-disubstituted amino acids, N-alkyl amino acids, lactic acid, and other unconventional amino acids may also be suitable components for polypeptides of the present disclosure. Examples of unconventional amino acids include, without limitation: aminoadipic acid, beta-alanine, beta-aminopropionic acid, aminobutyric acid, piperidinic acid, aminocaprioic acid, aminoheptanoic acid, aminoisobutyric acid, aminopimelic acid, diaminobutyric acid, desmosine, diaminopimelic acid, diaminopropionic acid, N-ethylglycine, N-ethylaspargine, hyroxylysine, allo-hydroxylysine, hydroxyproline, isodesmosine, allo-isoleucine, N-methylglycine, sarcosine, N-methylisoleucine, N-methylvaline, norvaline, norleucine, orithine, 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, sigma-N-methylarginine, and other similar amino acids and amino acids (e.g., 4-hydroxyproline).

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

Naturally occurring residues may be divided into classes based on common side chain properties:
1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human antibody that are homologous with non-human antibodies, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., J. Mol. Biol., 157:105-131 (1982). It is known that certain amino acids may be substituted for other amino acids having a similar hydropathic index or score and still retain a similar biological activity. In making changes based upon the hydropathic index, in certain embodiments, the substitution of amino acids whose hydropathic indices are within 0.2 is included. In certain embodiments, those which are within 0.1 are included, and in certain embodiments, those within 0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within 0.2 is included, in certain embodiments, those which are within 0.1 are included, and in certain embodiments, those within 0.5 are included. One may also identify epitopes from primary amino acid sequences on the basis of hydrophilicity. These regions are also referred to as "epitopic core regions."

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2): 211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nuci. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)).

In certain embodiments, antibody variants include glycosylation variants wherein the number and/or type of glycosylation site has been altered compared to the amino acid sequences of the parent polypeptide. In certain embodiments, protein variants comprise a greater or a lesser number of N-linked glycosylation sites than the native protein. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

According to certain embodiments, amino acid substitutions are those which: (1) reduce susceptibility to proteolysis, (2) reduce susceptibility to oxidation, (3) alter binding affinity for forming protein complexes, (4) alter binding affinities, and/or (5) confer or modify other functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et at. Nature 354:105 (1991).

The specific binding agent molecules of this disclosure that are polypeptide or peptide substitution variants may have up to about ten to twelve percent of the original amino acid sequence replaced. For antibody variants, the heavy chain may have 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 amino acid replaced, while the light chain may have 25, 24, 23, 22, 21, 20, 19, 18, 17, 16, 15, 14, 13, 12, 11, 10, 9, 8, 7, 6, 5, 4, 3, 2, or 1 amino acid replaced.

Derivatives of Specific Binding Agents

The disclosure also provides derivatives of specific binding agent polypeptides. Derivatives include specific binding agent polypeptides bearing modifications other than insertion, deletion, or substitution of amino acid residues. Preferably, the modifications are covalent in nature, and include for example, chemical bonding with polymers, lipids, other organic, and inorganic moieties. Derivatives of the disclosure may be prepared to increase circulating half-life of a specific binding agent polypeptide, or may be designed to improve targeting capacity for the polypeptide to desired cells, tissues, or organs.

The disclosure further embraces derivative binding agents covalently modified to include one or more water soluble polymer attachments such as polyethylene glycol, polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are specific binding agent products covalently modified with polyethylene glycol (PEG) subunits. Water-soluble polymers may be bonded at specific positions, for example at the amino terminus of the specific binding agent products, or randomly attached to one or more side chains of the polypeptide. The use of PEG for improving the therapeutic capacity for specific binding agent, and for humanized antibodies in particular, is described in U.S. Pat. No. 6,133,426 to Gonzales et al., issued Oct. 17, 2000.

Target Sites for Antibody Mutagenesis

Certain strategies can be employed to manipulate inherent properties of a JAML or JAML D1-specific antibody, such as the affinity of the antibody for its target. These strategies include the use of site-specific or random mutagenesis of the polynucleotide molecule encoding the antibody to generate antibody variants, followed by a screening step designed to recover antibody variants that exhibit the desired change, e.g. increased or decreased affinity.

The amino acid residues most commonly targeted in mutagenic strategies are those in the CDRs. As described supra, these regions contain the residues that actually interact with JAML or JAML D1 and other amino acids that affect the spatial arrangement of these residues. However, amino acids in the framework regions of the variable domains outside the CDR regions have also been shown to make contributions to the antigen-binding properties of the antibody, and can be targeted to manipulate such properties. See Hudson, Curr Opin Biotech, 9:395-402 (1999) and references therein.

Smaller and more effectively screened libraries of antibody variants can be produced by restricting random or site-directed mutagenesis to sites in the CDRs that correspond to areas prone to "hyper-mutation" during the somatic affinity maturation process. See Chowdhury and Pastan, Nature Biotech, 17: 568-572 [1999] and references therein. The types of DNA elements known to define hyper-mutation sites in this manner include direct and inverted repeats, certain consensus sequences, secondary structures, and palindromes. The consensus DNA sequences include the tetrabase sequence Purine-G-Pyrimidine-A/T (i.e. A or G-G-C or T-A or T) and the serine codon AGY (wherein Y can be a C or a T).

Thus, an embodiment of the present disclosure includes mutagenic strategies with the goal of increasing the affinity of an antibody for its target. These strategies include mutagenesis of the entire variable heavy and light chain, mutagenesis of the CDR regions only, mutagenesis of the consensus hypermutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished though solving the structure of the antibody in question, and the antibody-ligand complex, through techniques known to those skilled in the art, such as X-ray crystallography. Various methods based on analysis and characterization of such antibody crystal structures are known to those of skill in the art and can be employed, although not definitive, to approximate the CDR regions. Examples of such commonly used methods include the Kabat, Chothia, AbM and contact definitions.

The Kabat definition is based on the sequence variability and is the most commonly used definition to predict CDR regions. [Johnson and Wu, Nucleic Acids Res, 28: 214-8 (2000)]. The Chothia definition is based on the location of the structural loop regions. [Chothia et al., J Mol Biol, 196: 901-17 (1986); Chothia et al., Nature, 342: 877-83 (1989)]. The AbM definition is a compromise between the Kabat and Chothia definition. AbM is an integral suite of programs for antibody structure modeling produced by Oxford Molecular Group [Martin et al., Proc Natl Acad Sci (USA) 86:9268-9272 (1989); Rees, et al., ABM™, a computer program for modeling variable regions of antibodies, Oxford, UK; Oxford Molecular, Ltd.]. The AbM suite models the tertiary structure of an antibody from primary sequencing using a combination of knowledge databases and ab initio methods. An additional definition, known as the contact definition, has been recently introduced. [MacCallum et al., J Mol Biol, 5:732-45 (1996)]. This definition is based on an analysis of the available complex crystal structures.

By convention, the CDR regions in the heavy chain are typically referred to as H1, H2 and H3 and are numbered sequentially in order counting from the amino terminus to the carboxy terminus. The CDR regions in the light chain are typically referred to as L1, L2 and L3 and are numbered sequentially in order counting from the amino terminus to the carboxy terminus.

The CDR-H1 is approximately 10 to 12 residues in length and typically starts 4 residues after a Cys according to the Chothia and AbM definitions or typically 5 residues later according to the Kabat definition. The H1 is typically followed by a Trp, typically Trp-Val, but also Trp-Ile, or Trp-Ala. The length of H1 is approximately 10 to 12 residues according to the AbM definition while the Chothia definition excludes the last 4 residues.

The CDR-H2 typically starts 15 residues after the end of H1 according to the Kabat and AbM definition. The residues preceding H2 are typically Leu-Glu-Trp-Ile-Gly but there are a number of variations. H2 is typically followed by the amino acid sequence Lys/Arg-Leu/Ile/Val/Phe/Thr/Ala-Thr/Ser/Ile/Ala. According to the Kabat definition, the length of the H2 is approximately 16 to 19 residues where the AbM definition predicts the length to be typically 9 to 12 residues.

The CDR-H3 typically starts 33 residues after the end of H2 and is typically preceded by the amino acid sequence (typically Cys-Ala-Arg). The H3 is typically followed by the amino acid sequence-Gly. The length of H3 can be anywhere between 3 to 25 residues.

The CDR-L1 typically starts at approximately residue 24 and will typically follow a Cys. The residue after the CDR-L1 is always a Trp and will typically begin the sequence Trp-Tyr-Gln, Trp-Leu-Gln, Trp-Phe-Gln, or Trp-Tyr-Leu. The length of CDR-L1 is approximately 10 to 17 residues. The punitive CDR-L1 for the antibodies of the disclosure follows this pattern exactly with a Cys residue followed by 15 amino acids then Trp-Tyr-Gln.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-XXX-Gly. The length of L3 is approximately 7 to 11 residues.

Various methods for modifying antibodies have been described in the art. For example, U.S. Pat. No. 5,530,101 (to Queen et al., Jun. 25, 1996) describes methods to produce humanized antibodies wherein the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to affect binding affinity, such as one or more amino acids which are immediately adjacent to a CDR in the donor immunoglobulin or those within about 3 angstroms as predicted by molecular modeling. The heavy and light chains may each be designed by using any one or all of various position criteria. When combined into an intact antibody, the humanized immunoglobulins of the present disclosure will be substantially non-immunogenic in humans and retain substantially the same affinity as the donor immunoglobulin to the antigen, such as a protein or other compound containing an epitope. See also, related methods in U.S. Pat. No. 5,693,761 to Queen, et al., issued Dec. 2, 1997 ("Polynucleotides encoding improved humanized immunoglobulins"); U.S. Pat. No. 5,693,762 to Queen, et al., issued Dec. 2, 1997 ("Humanized Immunoglobulins"); U.S. Pat. No. 5,585,089 to Queen, et al. issued Dec. 17, 1996 ("Humanized Immunoglobulins").

In one example, U.S. Pat. No. 5,565,332 to Hoogenboom et al. issued Oct. 15, 1996 ("Production of chimeric antibodies—a combinatorial approach") describes methods for the production of antibodies, and antibody fragments which have similar binding specificity as a parent antibody but which have increased human characteristics. Humanized antibodies are obtained by chain shuffling, using, for example, phage display technology, and a polypeptide comprising a heavy or light chain variable domain of a non-human antibody specific for an antigen of interest is combined with a repertoire of human complementary (light or heavy) chain variable domains. Hybrid pairings that are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and used in a second humanizing shuffling step. Alternatively, this second step is eliminated if the hybrid is already of sufficient human character to be of therapeutic value. Methods of modification to increase human character are also described. See also Winter, FEBS Letts 430:92-92 (1998).

As another example, U.S. Pat. No. 6,054,297 to Carter et al., issued Apr. 25, 2000 describes a method for making humanized antibodies by substituting a CDR amino acid sequence for the corresponding human CDR amino acid sequence and/or substituting a FR amino acid sequence for the corresponding human FR amino acid sequences.

As another example, U.S. Pat. No. 5,766,886 to Studnicka et al., issued Jun. 16, 1998 ("Modified antibody variable domains") describes methods for identifying the amino acid residues of an antibody variable domain which may be modified without diminishing the native affinity of the antigen binding domain while reducing its immunogenicity with respect to a heterologous species and methods for preparing these modified antibody variable domains which are useful for administration to heterologous species. See also U.S. Pat. No. 5,869,619 to Studnicka issued Feb. 9, 1999.

Modification of an antibody by any of the methods known in the art is typically designed to achieve increased binding affinity for an antigen and/or reduce immunogenicity of the antibody in the recipient. In one approach, humanized antibodies can be modified to eliminate glycosylation sites in order to increase affinity of the antibody for its cognate antigen [Co et al., Mol Immunol 30:1361-1367 (1993)]. Techniques such as "reshaping," "hyperchimerization," and "veneering/resurfacing" have produced humanized antibodies with greater therapeutic potential. [Vaswami et al, Annals of Allergy, Asthma, & Immunol 81:105 (1998); Roguska et al., Prot Engineer 9:895-904 (1996)]. See also U.S. Pat. No. 6,072,035 to Hardman et al., issued Jun. 6, 2000, which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., J Immunol 62(6): 3663-71 (1999).

In certain instances, humanizing antibodies result in a loss of antigen binding capacity. It is therefore preferable to "back mutate" the humanized antibody to include one or more of the amino acid residues found in the original (most often rodent) antibody in an attempt to restore binding affinity of the antibody. See, for example, Saldanha et al., Mol Immunol 36:709-19 (1999).

Non-Peptide Specific Binding Agent Analogs/Protein Mimetics

Furthermore, nonpeptide specific binding agent analogs of peptides that provide a stabilized structure or lessened bio-degradation, are also contemplated. Specific binding agent peptide mimetic analogs can be prepared based on a selected inhibitory peptide by replacement of one or more residues by nonpeptide moieties. Preferably, the nonpeptide moieties permit the peptide to retain its natural confirmation, or stabilize a preferred, e.g., bioactive, confirmation which retains the ability to recognize and bind JAML or JAML D1. In one aspect, the resulting analog/mimetic exhibits increased binding affinity for JAML or JAML D1. One example of methods for preparation of nonpeptide mimetic analogs from specific binding agent peptides is described in Nachman et al., Regul Pept 57:359-370 (1995). If desired, the specific binding agent peptides of the disclosure can be modified, for instance, by glycosylation, amidation, carboxylation, or phosphorylation, or by the creation of acid addition salts, amides, esters, in particular C-terminal esters, and N-acyl derivatives of the peptides of the disclosure. The specific binding agent peptides also can be modified to create peptide derivatives by forming covalent or noncovalent complexes with other moieties. Covalently-bound complexes can be prepared by linking the chemical moieties to functional groups on the side chains of amino acids comprising the specific binding agent peptides, or at the N- or C-terminus.

In particular, it is anticipated that the specific binding agent peptides can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). The disclosure accordingly provides a molecule comprising an antibody molecule, wherein the molecule preferably further comprises a reporter group selected from the group consisting of a radiolabel, a fluorescent label, an enzyme, a substrate, a solid matrix, and a carrier. Such labels are well known to those of skill in the art, e.g., biotin labels are particularly contemplated. The use of such labels is well known to those of skill in the art and is described in, e.g., U.S. Pat. No. 3,817,837; U.S. Pat. No. 3,850,752; U.S. Pat. No. 3,996,345 and U.S. Pat. No. 4,277,437. Other labels that will be useful include but are not limited to radioactive labels, fluorescent labels and chemiluminescent labels. U.S. Patents concerning use of such labels include for example U.S. Pat. No. 3,817,837; U.S. Pat. No. 3,850,752; U.S. Pat. No. 3,939,350 and U.S. Pat. No. 3,996,345. Any of the peptides of the present disclosure may comprise one, two, or more of any of these labels.

Methods of Making Specific Binding Agents

Specific binding agents of the present disclosure that are proteins can be prepared by chemical synthesis in solution or on a solid support in accordance with conventional techniques. The current limit for solid phase synthesis is about 85-100 amino acids in length. However, chemical synthesis techniques can often be used to chemically ligate a series of smaller peptides to generate full length polypeptides. Various automatic synthesizers are commercially available and can be used in accordance with known protocols. See, for example, Stewart and Young, Solid Phase Peptide Synthesis, 2d. ed., Pierce Chemical Co., (1984); Tam et al., J Am Chem Soc, 105:6442, (1983); Merrifield, Science, 232:341-347, (1986); and Barany and Merrifield, The Peptides, Gross and Meienhofer, eds, Academic Press, New York, 1-284; Barany et al., Int. J. Peptide Protein Res., 30, 705-739 (1987); and U.S. Pat. No. 5,424,398), each incorporated herein by reference.

Solid phase peptide synthesis methods use a copoly (styrene-divinylbenzene) containing 0.1-1.0 mM amines/g polymer. These methods for peptide synthesis use butyloxy-carbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide (See, Coligan et al., Current Protocols in Immunology, Wiley Interscience, 1991, Unit 9). On completion of chemical synthesis, the synthetic peptide can be deprotected to remove the t-BOC or FMOC amino acid blocking groups and cleaved from the polymer by treatment with acid at reduced temperature (e.g., liquid HF-10% anisole for about 0.25 to about 1 hour at 0 degree C.). After evaporation of the reagents, the specific binding agent peptides are extracted from the polymer with 1% acetic acid solution that is then lyophilized to yield the crude material. This can normally be purified by such techniques as gel filtration on Sephadex G-15 using 5% acetic acid as a solvent. Lyophilization of appropriate fractions of the column will yield the homogeneous specific binding agent peptide or peptide derivatives, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Chemical synthesis of anti-JAML or JAML D1 antibodies, derivatives, variants, and fragments thereof, as well as other protein-based JAML or JAML D1 binding agents permits incorporation of non-naturally occurring amino acids into the agent.

Recombinant DNA techniques are a convenient method for preparing full length antibodies and other large proteinaceous specific binding agents of the present disclosure, or fragments thereof. A cDNA molecule encoding the antibody or fragment may be inserted into an expression vector, which can in turn be inserted into a host cell for production of the antibody or fragment. It is understood that the cDNAs encoding such antibodies may be modified to vary from the "original" cDNA (translated from the mRNA) to provide for codon degeneracy or to permit codon preference usage in various host cells.

Generally, a DNA molecule encoding an antibody can be obtained using procedures described herein in the Examples. Where it is desirable to obtain Fab molecules or CDRs that are related to the original antibody molecule, one can screen a suitable library (phage display library; lymphocyte library, etc.) using standard techniques to identify and clone related Fabs/CDRs. Probes used for such screening may be full length or truncated Fab probes encoding the Fab portion of the original antibody, probes against one or more CDRs from the Fab portion of the original antibody, or other suitable probes. Where DNA fragments are used as probes, typical hybridization conditions are those such as set forth in Ausubel et al. (Current Protocols in Molecular Biology, Current Protocols Press [1994]). After hybridization, the probed blot can be washed at a suitable stringency, depending on such factors as probe size, expected homology of probe to clone, the type of library being screened, and the number of clones being screened. Examples of high stringency screening are 0.1 times SSC, and 0.1 percent SDS at a temperature between 50-65 degree C.

A variety of expression vector/host systems may be utilized to contain and express the polynucleotide molecules encoding the specific binding agent polypeptides of the disclosure. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian cells that are useful in recombinant specific binding agent protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells, as well as hybridoma cell lines as described herein. Mammalian cells are preferred for preparation of those specific binding agents such as antibodies and antibody fragments that are typically glycosylated and require proper refolding for activity. Preferred mammalian cells include CHO cells, hybridoma cells, and myeloid cells.

Some exemplary protocols for the recombinant expression of the specific binding agent proteins are described herein below.

The term "expression vector" refers to a plasmid, phage, virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or sequence that encodes the binding agent which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant specific binding agent protein is expressed without a leader or transport sequence, it may include an amino terminal methionine residue. This residue may or may not be subsequently cleaved from the expressed recombinant protein to provide a final specific binding agent product.

For example, the specific binding agents may be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted specific binding agent peptide is purified from the yeast growth medium by, e.g., the methods used to purify the peptide from bacterial and mammalian cell supernatants.

Alternatively, the cDNA encoding the specific binding agent peptide may be cloned into the baculovirus expression vector pVL1393 (PharMingen, San Diego, Calif.). This vector can be used according to the manufacturer's directions (PharMingen) to infect *Spodoptera frugiperda* cells in sF9 protein-free media and to produce recombinant protein. The specific binding agent protein can be purified and concentrated from the media using a heparin-Sepharose column (Pharmacia).

Alternatively, the peptide may be expressed in an insect system. Insect systems for protein expression are well known to those of skill in the art. In one such system, *Autographa californica* nuclear polyhedrosis virus (AcNPV) can be used as a vector to express foreign genes in *Spodoptera frugiperda* cells or in *Trichoplusia* larvae. The specific binding agent peptide coding sequence can be cloned into a nonessential region of the virus, such as the polyhedrin gene, and placed under control of the polyhedrin promoter. Successful insertion of the specific binding agent peptide will render the polyhedrin gene inactive and produce recombinant virus lacking coat protein coat. The recombinant viruses can be used to infect *S. frugiperda* cells or *Trichoplusia* larvae in which peptide is expressed [Smith et al., J Virol 46: 584 (1983); Engelhard et al., Proc Nat Acad Sci (USA) 91: 3224-7 (1994)].

In another example, the DNA sequence encoding the specific binding agent peptide can be amplified by PCR and cloned into an appropriate vector for example, pGEX-3X (Pharmacia). The pGEX vector is designed to produce a fusion protein comprising glutathione-S-transferase (GST), encoded by the vector, and a specific binding agent protein encoded by a DNA fragment inserted into the vector's cloning site. The primers for the PCR can be generated to include for example, an appropriate cleavage site. Where the specific binding agent fusion moiety is used solely to facilitate expression or is otherwise not desirable as an attachment to the peptide of interest, the recombinant specific binding agent fusion protein may then be cleaved from the GST portion of the fusion protein. The pGEX-3x/specific binding agent peptide construct is transformed into E. coli XL-1 Blue cells (Stratagene, La Jolla Calif.), and individual transformants isolated and grown. Plasmid DNA from individual transformants can be purified and partially sequenced using an automated sequencer to confirm the presence of the desired specific binding agent encoding nucleic acid insert in the proper orientation.

Expression of polynucleotides encoding anti-JAML or JAML D1 antibodies and fragments thereof using the recombinant systems described above may result in production of antibodies or fragments thereof that must be "re-folded" (to properly create various disulphide bridges) in order to be biologically active. Typical refolding procedures for such antibodies are set forth in the Examples herein and in the following section.

Specific binding agents made in bacterial cells may be produced as an insoluble inclusion body in the bacteria, can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000.times.g. The specific binding agent-containing pellet can be resuspended in 50 mM Tris, pH 8, and 10 mM EDTA, layered over 50% glycerol, and centrifuged for 30 min. at 6000 times g. The pellet can be resuspended in standard phosphate buffered saline solution (PBS) free of Mg and Ca. The specific binding agent can be further purified by fractionating the resuspended pellet in a denaturing SDS polyacrylamide gel (Sambrook et al., supra). The gel can be soaked in 0.4 M KCl to visualize the protein, which can be excised and electroeluted in gel-running buffer lacking SDS. If the GST fusion protein is produced in bacteria, as a soluble protein, it can be purified using the GST Purification Module (Pharmacia).

Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, WI38, as well as hybridoma cell lines, and the like have specific cellular machinery and characteristic mechanisms for such post-translational activities and can be chosen to ensure the correct modification and processing of the introduced, foreign protein.

A number of selection systems can be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk–, hgprt– or aprt– cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

Purification and Refolding of Specific Binding Agents

In some cases, the specific binding agents produced using procedures described above may need to be "refolded" and oxidized into a proper tertiary structure and generating di-sulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization, however a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for dusykfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

It will be desirable to purify specific binding agent proteins or variants thereof of the present disclosure. Protein purification techniques are well known to those of skill in the art. These techniques involve, at one level, the crude fractionation of the polypeptide and non-polypeptide fractions. Having separated the specific binding agent polypeptide from other proteins, the polypeptide of interest can be further purified using chromatographic and electrophoretic techniques to achieve partial or complete purification (or purification to homogeneity). Analytical methods particularly suited to the preparation of a pure specific binding agent peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present disclosure concerns the purification, and in particular embodiments, the substantial purification, of an encoded specific binding agent protein or peptide. The term "purified specific binding agent protein or peptide" as used herein, is intended to refer to a composition, isolatable from other components, wherein the specific binding agent protein or peptide is purified to any degree relative to its naturally-obtainable state. A purified specific binding agent protein or peptide therefore also refers to a specific binding agent protein or peptide, free from the environment in which it may naturally occur.

Generally, "purified" will refer to a specific binding agent composition that has been subjected to fractionation to remove various other components, and which composition substantially retains its expressed biological activity. Where the term "substantially purified" is used, this designation will refer to a specific binding agent composition in which the specific binding agent protein or peptide forms the major component of the composition, such as constituting about 50%, about 60%, about 70%, about 80%, about 90%, about 95% or more of the proteins in the composition.

Various methods for quantifying the degree of purification of the specific binding agent will be known to those of skill in the art in light of the present disclosure. These include, for example, determining the specific binding activity of an active fraction, or assessing the amount of specific binding agent polypeptides within a fraction by SDS/PAGE analysis. A preferred method for assessing the purity of a specific binding agent fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the expressed specific binding agent protein or peptide exhibits a detectable binding activity.

Various techniques suitable for use in specific binding agent protein purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified specific binding agent.

There is no general requirement that the specific binding agent always be provided in its most purified state. Indeed, it is contemplated that less substantially specific binding agent products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low-pressure chromatography system. Methods exhibiting a lower degree of relative purification may have advantages in total recovery of specific binding agent protein product, or in maintaining binding activity of an expressed specific binding agent protein.

It is known that the migration of a polypeptide can vary, sometimes significantly, with different conditions of SDS/PAGE [Capaldi et al., Biochem Biophys \Res Comm, 76: 425 (1977)]. It will therefore be appreciated that under differing electrophoresis conditions, the apparent molecular weights of purified or partially purified specific binding agent expression products may vary.

Binding Assays

Immunological binding assays typically utilize a capture agent to bind specifically to and often immobilize the analyte target antigen. The capture agent is a moiety that specifically binds to the analyte. In one embodiment of the present disclosure, the capture agent is an antibody or fragment thereof that specifically binds JAML or JAML D1.

Immunological binding assays frequently utilize a labeling agent that will signal the existence of the bound complex formed by the capture agent and antigen. The labeling agent can be one of the molecules comprising the bound complex; i.e. it can be labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species [see, generally Akerstrom, J Immunol, 135:2589-2542 (1985); and Chaubert, Mod Pathol, 10:585-591 (1997)].

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized antibodies then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. [See, Harlow and Lane, Antibodies, A Laboratory Manual, Ch 14, Cold Spring Harbor Laboratory, NY (1988), incorporated herein by reference].

Immunological binding assays can be of the competitive type. The amount of analyte present in the sample is measure indirectly by measuring the amount of an added analyte displaced, or competed away, from a capture agent by the analyte present in the sample. In one preferred competitive binding assay, a known amount of analyte, usually labeled, is added to the sample and the sample is then contacted with an antibody (the capture agent). The amount of labeled analyze bound to the antibody is inversely proportional to the concentration of analyte present in the sample. (See, Harlow and Lane, Antibodies, A Laboratory Manual, Ch 14, pp. 579-583, supra).

In another preferred competitive binding assay, the antibody is immobilized on a solid substrate. The amount of protein bound to the antibody may be determined either by measuring the amount of protein present in a protein/antibody complex, or alternatively by measuring the amount of remaining uncomplexed protein. The amount of protein may be detected by providing a labeled protein. See, Harlow and Lane, Antibodies, A Laboratory Manual, Ch 14, supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

The competitive binding assays can be used for cross-reactivity determinations to permit a skilled artisan to determine if a protein or enzyme complex which is recognized by a specific binding agent of the disclosure is the desired protein and not a cross-reacting molecule or to determine whether the antibody is specific for the antigen and does not bind unrelated antigens. In assays of this type, antigen can be immobilized to a solid support and an unknown protein mixture is added to the assay, which will compete with the binding of the specific binding agents to the immobilized protein. The competing molecule also binds one or more antigens unrelated to the antigen. The ability of the proteins to compete with the binding of the specific binding agents antibodies to the immobilized antigen is compared to the binding by the same protein that was immobilized to the solid support to determine the cross-reactivity of the protein mix.

The present disclosure also provides Western blot methods to detect or quantify the presence of JAML or JAML D1 in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or fragments thereof that specifically bind JAML or JAML D1 and the resulting complex is detected. These antibodies may be directly labeled or alternatively may be subsequently detected using labeled antibodies that specifically bind to the antibody.

Diagnostic Assays

The antibodies or antigen-binding fragments thereof of present disclosure are useful for the diagnosis of conditions or diseases characterized by expression of JAML or JAML D1 or subunits, or in assays to monitor patients being treated with inducers of JAML or JAML D1, its fragments, agonists or inhibitors of JAML or JAML D1 activity. Diagnostic assays for JAML or JAML D1 include methods utilizing a specific binding agent and a label to detect JAML or JAML D1 in human body fluids or extracts of cells or tissues. The specific binding agents of the present disclosure can be used with or without modification. In a preferred diagnostic assay, the specific binding agents will be labeled by attaching, e.g., a label or a reporter molecule. A wide variety of labels and reporter molecules are known, some of which have been already described herein. In particular, the present disclosure is useful for diagnosis of human disease.

A variety of protocols for measuring JAML or JAML D1 proteins using either polyclonal or monoclonal antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on JAML or JAML D1 is preferred, but a competitive binding assay can be employed. These assays are described, for example, in Maddox et al., J Exp Med, 158:1211 [1983].

In order to provide a basis for diagnosis, normal or standard values for human JAML or JAML D1 expression are usually established. This determination can be accomplished by combining body fluids or cell extracts from normal subjects, preferably human, with a specific binding agent, for example, an antibody, to JAML or JAML D1, under conditions suitable for complex formation that are well known in the art. The amount of standard complex formation can be quantified by comparing the binding of the specific binding agents to known quantities of JAML or JAML D1 protein, with both control and disease samples. Then, standard values obtained from normal samples can be compared with values obtained from samples from subjects potentially affected by disease. Deviation between standard and subject values suggests a role for JAML or JAML D1 in the disease state.

For diagnostic applications, in certain embodiments, specific binding agents typically will be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin; or an enzyme, such as alkaline phosphatase, beta-galactosidase, or horseradish peroxidase [Bayer et al., Meth Enz, 184: 138-163, (1990)].

Conditions and Diseases

The present disclosure provides a specific binding agent that binds to JAML or JAML D1 that is useful for the treatment of human diseases and pathological conditions. Agents that modulate JAML or JAML D1 binding activity, or other cellular activity, may be used in combination with other therapeutic agents to enhance their therapeutic effects or decrease potential side effects.

In one aspect, the present disclosure provides reagents and methods useful for treating diseases and conditions characterized by undesirable or aberrant levels of JAML or JAML D1 activity in an epithelial cell such as allergies, scarring, periodontal disease, and respiratory diseases such as athsma, chronic obstructive pulmonary disorder, and multiple sclerosis. These diseases include inflammatory diseases, viral infections cancers, and other hyperproliferative conditions, such as hyperplasia, psoriasis, contact dermatitis, immunological disorders, and infertility.

In certain embodiments, the inflammatory disease is atherosclerosis, and ischaemic heart disease, acne vulgaris, asthma, chronic prostatitis, hypersensitivities, inflammatory bowel diseases, pelvic inflammatory disease, reperfusion injury, or transplant rejection.

In certain embodiments, the autoimmune disease is rheumatoid arthritis, amyotrophic lateral sclerosis, Crohn's disease, type 1 diabetes, psoriasis, sarcoidosis, interstitial cystitis, glomerulonephritis, vasculitis, and ulcerative colitis.

Other contemplated diseases or conditions include acne vulgaris, Celiac disease, chronic prostatitis, glomerulonephritis, and hypersensitivities.

Other aspects of the present disclosure include treating various retinopathies (including diabetic retinopathy and age-related macular degeneration) in which angiogenesis is involved, as well as disorders/diseases of the female reproductive tract such as endometriosis, uterine fibroids, and other such conditions associated with dysfunctional vascular proliferation (including endometrial microvascular growth) during the female reproductive cycle.

The present disclosure also provides methods of treating cancer in an animal, including humans, comprising administering to the animal an effective amount of a specific binding agent that inhibits or decreases JAML or JAML D1 activity. The disclosure is further directed to methods of inhibiting cancer cell growth, including processes of cellular proliferation, invasiveness, and metastasis in biological systems. Methods include use of a compound of the disclosure as an inhibitor of cancer cell growth. Preferably, the methods are employed to inhibit or reduce cancer cell growth, invasiveness, metastasis, or tumor incidence in living animals, such as mammals. Methods of the disclosure are also readily adaptable for use in assay systems, e.g., assaying cancer cell growth and properties thereof, as well as identifying compounds that affect cancer cell growth. Cancers whose invasiveness or metastasis is associated with JAML or JAML D1 expression or activity are especially susceptible to being inhibited or even induced to regress by means of the disclosure.

The cancers treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle.

Combination Therapies

The disclosure can also be practiced by including with a specific binding agent of the disclosure, such as an antibody, in combination with another therapeutic agent.

Chemotherapy treatment can employ anti-neoplastic agents including, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy can done in conjunction with the growth factors listed below or with agents that are designed to inhibit the growth factors listed below. The growth factors include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin.

With regard to asthma the binding agent may be administered in combination with short acting beta 2-adrenoceptor agonists (SABA), such as salbutamol (albuterol), anticholinergic medications, such as ipratropium bromide, anticholinergic, epinephrine, fluticasone propionate, glucocorticoids, long acting beta-adrenoceptor agonists (LABA) leukotriene antagonists such as zafirlukast, mast cell stabilizers such as cromolyn sodium.

The combination therapy also contemplates use of the disclosed pharmaceutical compositions with radiation therapy or surgery, as an alternative, or a supplement, to a second therapeutic or chemotherapeutic agent.

In some embodiments, the disclosure relates to treating a viral infection by administering JAML or JAML D1 specific binding agents disclosed herein in combination with a second antiviral agent. In further embodiments, a GM-CSF and IL-7 conjugate is administered in combination with one or more of the following agents: abacavir, acyclovir, acyclovir, adefovir, amantadine, amprenavir, ampligen, arbidol, atazanavir, atripla, boceprevir, cidofovir, combivir, darunavir, delavirdine, didanosine, docosanol, edoxudine, efavirenz, emtricitabine, enfuvirtide, entecavir, famciclovir, fomivirsen, fosamprenavir, foscarnet, fosfonet, ganciclovir, ibacitabine, immunovir, idoxuridine, imiquimod, indinavir, inosine, interferon type III, interferon type II, interferon type I, lamivudine, lopinavir, loviride, maraviroc, moroxydine, methisazone, nelfinavir, nevirapine, nexavir, oseltamivir (Tamiflu), peginterferon alfa-2a, penciclovir, peramivir, pleconaril, podophyllotoxin, raltegravir, ribavirin, rimantadine, ritonavir, pyramidine, saquinavir, stavudine, tenofovir, tenofovir disoproxil, tipranavir, trifluridine, trizivir, tromantadine, truvada, valaciclovir (Valtrex), valganciclovir, vicriviroc, vidarabine, viramidine zalcitabine, zanamivir (Relenza), and/or zidovudine (AZT).

Pharmaceutical Compositions

Pharmaceutical compositions of JAML or JAML D1 specific binding agents are within the scope of the present disclosure. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of a specific binding agent, such as an antibody, or a fragment, variant, derivative or fusion thereof as described herein, in admixture with a pharmaceutically acceptable agent. In a preferred embodiment, pharmaceutical compositions comprise antagonist specific binding agents that modulate partially or completely at least one biological activity of JAML in admixture with a pharmaceutically acceptable agent. Typically, the specific binding agents will be sufficiently purified for administration to an animal The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific binding agent.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present disclosure, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When parenteral administration is contemplated, the therapeutic compositions for use in this disclosure may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present disclosure, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., Biopolymers, 22:547-556 (1983)], poly(2-hydroxyethyl-methacrylate) [Langer et al., J Biomed Mater Res, 15:167-277, (1981)] and [Langer et al., Chem Tech, 12:98-105 (1982)], ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., Proc Natl Acad Sci (USA), 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present disclosure is directed to kits for producing a single-dose administration unit. The kits may each contain both a first container having a dried protein and a second container having an aqueous formulation. Also included within the scope of this disclosure are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding agent molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent which is a polypeptide can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Terms

Junctional adhesion molecules (JAM) typically form tight junctions between epithelial cells serving as a physical barrier to prevent solutes and water from passing freely through the paracellular space. The terms "JAM-like protein" or "JAML" refer to a polypeptide containing two extracellular immunoglobulin-like domains, a transmembrane segment, and a cytoplasmic tail with a conserved dimerization motif among JAM members. One contemplated human isoform of JAML has the sequence (SEQ ID NO:67) MFCPLKLILL PVLLDYSLGL NDLNVSPPEL TVHVGDSALM GCVFQSTEDK CIFKIDWTLS 61 PGEHAKDEYV LYYYSNLSVP IGRFQNRVHL MGDILCNDGS LLLQDVQEAD QGTYICEIRL 121 KGESQVFKKA VVLHVLPEEP KELMVHVGGL IQMGCVFQST EVKHVTKVEW IFSGRRAKEE 181 IVFRYYHKLR MSVEYSQSWG HFQNRVNLVG DIFRNDGSIM LQGVRESDGG NYTCSIHLGN 241 LVFKKTIVLH VSPEEPRTLV TPAALRPLVL GGNQLVIIVG IVCATILLLP VLILIVKKTC 301 GNKSSVNSTV LVKNTKKTNP EIKEKPCHFE RCEGEKHIYS PIIVREVIEE EEPSEKSEAT 361 YMTMHPVWPS LRSDRNNSLE KKSGGGMPKT QQAF. The N-terminal D1 domain of human junctional adhesion molecules and like molecules contains two antiparallel β-sheets which are an Ig-like domain of the variable type. One contemplated human JAML D1 domain has the sequence of a.a 1-140.

The term "specific binding agent" refers to a molecule, preferably a proteinaceous molecule, that binds JAML or in certain instances JAML D1 with a greater affinity than other JAM proteins or domains, e.g., JAMA, JAMC, JAML D2. Typically the specific binding agent is an antibody, such as a polyclonal antibody, a monoclonal antibody (mAb), a chimeric antibody, a CDR-grafted antibody, a multi-specific antibody, a bi-specific antibody, a catalytic antibody, a humanized antibody, a human antibody, an anti-idiotypic (anti-Id) antibody, and antibodies that can be labeled in soluble or bound form, as well as antigen-binding fragments, variants or derivatives thereof, either alone or in combination with other amino acid sequences, provided by known techniques.

The term "polyclonal antibody" refers to a heterogeneous mixture of antibodies that recognize and bind to different epitopes on the same antigen. Polyclonal antibodies may be obtained from crude serum preparations or may be purified using, for example, antigen affinity chromatography, or Protein A/Protein G affinity chromatography.

The term "monoclonal antibodies" refers to a collection of antibodies encoded by the same nucleic acid molecule that are optionally produced by a single hybridoma (or clone thereof) or other cell line, or by a transgenic mammal such that each monoclonal antibody will typically recognize the same epitope on the antigen. The term "monoclonal" is not limited to any particular method for making the antibody, nor is the term limited to antibodies produced in a particular species, e.g., mouse, rat, etc.

The term "chimeric antibodies" refers to antibodies in which a portion of the heavy and/or light chain is identical with or homologous to a corresponding sequence in an antibody derived from a particular species or belonging to a particular antibody class or subclass, while the remainder of the chain(s) is/are identical with or homologous to a corresponding sequence in antibodies derived from another species or belonging to another antibody class or subclass. Also included are antigen-binding fragments of such antibodies that exhibit the desired biological activity (i.e., the ability to specifically bind JAML or JAML-D1). See, U.S. Pat. No. 4,816,567 and Morrison et al., Proc Natl Acad Sci (USA), 81:6851-6855 [1985].

The term "CDR grafted antibody" refers to an antibody in which the CDR from one antibody of a particular species or isotype is recombinantly inserted into the framework of another antibody of the same or different species or isotype.

The term "multi-specific antibody" refers to an antibody having variable regions that recognize more than one epitope on one or more antigens. A subclass of this type of antibody is a "bi-specific antibody" which recognizes two distinct epitopes on the same or different antigens.

The term "humanized antibody" refers to a specific type of CDR-grafted antibody in which the antibody framework region is derived from a human but each CDR is replaced with that derived from another species, such as a murine CDR. The term "CDR" is defined infra.

The term "fully human" antibody refers to an antibody in which both the CDR and the framework are derived from one or more human DNA molecules.

The term "variants," as used herein, include those polypeptides wherein amino acid residues are inserted into, deleted from and/or substituted into the naturally occurring (or at least a known) amino acid sequence for the binding agent. Variants of the disclosure include fusion proteins as described below.

"Specifically binds" refers to the ability of a specific binding agent (such as an antibody or fragment thereof) of the present disclosure to recognize and bind mature, full-length or partial-length target polypeptide (herein JAML and JAML D1), or an ortholog thereof, such that its affinity (as determined by, e.g., Affinity ELISA or assays as described herein) or its neutralization capability (as determined by e.g., Neutralization ELISA assays described herein, or similar assays) is at least 10 times as great, but optionally 50 times as great, 100, 250 or 500 times as great, or even at least 1000 times as great as the affinity or neutralization capability of the same for any other or other peptide or polypeptide.

The term "antigen binding domain" or "antigen binding region" refers to that portion of the specific binding agent (such as an antibody molecule) which contains the specific binding agent amino acid residues (or other moieties) that interact with an antigen and confer on the binding agent its specificity and affinity for the antigen. In an antibody, the antigen-binding domain is commonly referred to as the "complementarity-determining region, or CDR."

The term "epitope" refers to that portion of any molecule capable of being recognized by and bound by a specific binding agent, e.g. an antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous. Moreover, epitopes may be mimetic in that they comprise a three dimensional structure that is identical to the epitope used to generate the antibody, yet comprise none or only some of the amino acid residues found in the JAML or JAML D1 used to stimulate the antibody immune response.

The term "inhibiting and/or neutralizing epitope" is an epitope, which when bound by a specific binding agent such as an antibody, results in the loss of (or at least the decrease in) biological activity of the molecule, cell, or organism containing such epitope, in vivo, in vitro, or in situ. In the context of the present disclosure, the neutralizing epitope is located on or is associated with a biologically active region of JAML.

The term "antibody fragment" refers to a peptide or polypeptide which comprises less than a complete, intact antibody. Complete antibodies comprise two functionally independent parts or fragments: an antigen binding fragment known as "Fab," and a carboxy terminal crystallizable fragment known as the "Fc" fragment. The Fab fragment includes the first constant domain from both the heavy and light chain (CH1 and CL1) together with the variable regions from both the heavy and light chains that bind the specific antigen. Each of the heavy and light chain variable regions includes three complementarity determining regions (CDRs) and framework amino acid residues which separate the individual CDRs. The Fc region comprises the second and third heavy chain constant regions (CH2 and CH3) and is involved in effector functions such as complement activation and attack by phagocytic cells. In some antibodies, the Fc and Fab regions are separated by an antibody "hinge region," and depending on how the full length antibody is proteolytically cleaved, the hinge region may be associated with either the Fab or Fc fragment. For example, cleavage of an antibody with the protease papain results in the hinge region being associated with the resulting Fc fragment, while cleavage with the protease pepsin provides a fragment wherein the hinge is associated with both Fab fragment simultaneously. Because the two Fab fragments are in fact covalently linked following pepsin cleavage, the resulting fragment is termed the F(ab')2 fragment.

An Fc domain may have a relatively long serum half-life, whereas a Fab is short-lived. [Capon et al., Nature, 337: 525-31 (1989)] When expressed as part of a fusion protein, an Fc domain can impart longer half-life or incorporate such functions as Fc receptor binding, Protein A binding, complement fixation and perhaps even placental transfer into the protein to which it is fused. The Fc region may be a naturally occurring Fc region, or may be altered to improve certain qualities, such as therapeutic qualities or circulation time.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable regions typically differ extensively in amino acid sequence even among antibodies of the same species. The variable region of an antibody typically determines the binding and specificity of each particular antibody for its particular antigen. The variability in sequence is concentrated in those regions referred to as complementarity-determining regions (CDRs), while the more highly conserved regions in the variable domain are called framework regions (FR). The CDRs of the light and heavy chains contain within them the amino acids which are largely responsible for the direct interaction of the antibody with antigen, however, amino acids in the FRs can significantly affect antigen binding/recognition as discussed herein infra.

The term "light chain" when used in reference to an antibody collectively refers to two distinct types, called kappa (k) or lambda (l) based on the amino acid sequence of the constant domains.

The term "heavy chain" when used in reference to an antibody collectively refers to five distinct types, called alpha, delta, epsilon, gamma and mu, based on the amino acid sequence of the heavy chain constant domain. The combination of heavy and light chains give rise to five known classes of antibodies: IgA, IgD, IgE, IgG and IgM, respectively, including four known subclasses of IgG, designated as IgG1, IgG$_2$, IgG$_3$ and IgG$_4$.

The term "naturally occurring" when used in connection with biological materials such as nucleic acid molecules, polypeptides, host cells, and the like, refers to those which are found in nature and not modified by a human being.

The term "isolated" when used in relation to a specific binding agent of JAML refers to a compound that is free from at least one contaminating polypeptide or compound that is found in its natural environment, and preferably substantially free from any other contaminating mammalian polypeptides that would interfere with its therapeutic or diagnostic use, e.g., purified.

As used herein, the term "combination with" when used to describe administration with an additional treatment means that the agent may be administered prior to, together with, or after the additional treatment, or a combination thereof.

As used herein, "subject" refers to any animal, typically a human patient, livestock, or domestic pet.

As used herein "a" and "an" refer to one or more.

As used herein "X" means an amino acid e.g., A, R, N, D, C, E, Q, G, H, I, L, K, M, F, P, S, T, W, Y, V, as recognized by IUPAC/IUBMB.

EXPERIMENTAL

Example 1

Generation of Monoclonal Antibodies Specific for Human JAML

Initially, fusions using standard methods were employed from immunizing mice with rabbit Fc-tagged soluble human JAML followed by screening with an ELISA to detected antibody binding to same antigen construct. In parallel, antibodies that reacted by ELISA to purified rabbit Fc were identified in order to eliminate antibodies that bound to the Fc tag. Using this approach, antibodies reactive to the Fc tag were found, but only weak signals against JAML. Over four years fusion attempts failed to identify any monoclonal antibodies specific for human JAML.

For hybridoma selection, soluble extracellular domains of JAML were employed as well as full-length JAML expressed on the cell surface of CHO-transfectants. Soluble recombinant, and full length JAML were tagged at the C-terminus with 6×Myc since the immunogen consisted of the extracellular domain of JAML tagged with 10 Histidine residues. Constructs were cloned into pcDNA3.0 for eukaryotic expression. Soluble recombinant extracellular domain of human JAML was generated in the supernatants of transfected HEK293T cells and identified by dot blot, spotting 5 µl supernatant on a nitrocellulose membrane and using the mAb 9E10 anti Myc, followed by HRP-conjugated secondary antibody and chemiluminescence. To identify antibodies to JAML, a novel capture ELISA was designed by coating Immulon II plates with the purified extracellular domain of CAR that was tagged with GST (CAR-GST). After blocking and washing coated wells, supernatants of HEK293T cells expressing soluble JAML-6×Myc were added to the CAR-coated plate. To detect immune serum titers against anti JAML-His, dilutions sera were applied from immunized mice followed by detection with HRP-conjugated secondary anti mouse IgG (H+L) antibody revealed with ABTS and colorimetric measurements. This assay was used in parallel with ELISA assays employing purified JAML-6×Myc to detect specific antibodies.

Parallel assays were performed that involved screening for direct antibody binding to CHO-K1 cells transfected with pcDNA3 construct encoding the full-length JAML gene with a 6×Myc tag at its C-terminus using the PEI reagent. After 3 days post transfection, cultures were selected with 500 µg G418 and incubated in the selection medium for 7-10 days at which time the culture was trypsinized. To identify JAML expressing transfectants, cells were stained with immune serum from the JAML immunized mice and cloned by limiting dilution. Individual clones were again stained with polyclonal anti JAML serum and positively labeled cells were selected for high surface expression of JAML. JAML expression was also revealed by Western Blot using the Myc antibody 9E10.

Highly purified recombinant soluble JAML-His was generated by transfecting the soluble JAML gene construct into human HEK293Tcells. The recombinant protein tagged at the C-terminus with 10 Histidine residues was purified on Ni-Agarose column, eluted with imidazole and subjected to size-exclusion chromatography on a Biologic Duo Flow System. Protein purity was verified by gel electrophoresis and Coomassie staining as well as Western Blotting using an HRP-conjugated goat anti His.

Balb/C female mice were immunized by intraperitoneal injection (I.P.) with 50 µg of purified, recombinant soluble JAML-His in complete Freund's adjuvant. This first injection was followed by an extended schedule of repeated boosts of 50 µg each at 2-week intervals in incomplete Freund's adjuvant. After four immunizations, animals were allowed to rest for three weeks followed by a final boost administered three days before the fusion. Serum was collected prior sacrificing the animal. Splenocytes were collected and fused to P3U1 myeloma cells (propagated in DMEM, 10% FBS with supplements) at a ratio of 3 to 1 respectively, using 1500 MW polyethylene glycol (PEG) (Roche Diagnostics, Mannheim, Germany). Resultant hybridomas were plated in 10×96 tissue culture wells and selected in HAT medium (ATCC, Manassas, Va.). Supernatants of individual wells were screened in parallel by ELISA assays using the novel capture ELISA described above (coating with CAR-GST, applying supernatants containing sJAML-6×Myc) and a standard binding ELISA assay detecting binding of supernatant IgG to microtiter wells coated with soluble JAML-6×Myc. Approximately ¼ of the total hybridomas reacted in either of the two assays above as determined by binding levels that were above twice the background value.

These hybridomas were further tested for reactivity against tagged, full-length JAML expressed on the surface of cultured cells. CHO-JAML-6×Myc transfectants were aliquoted and pelleted into round bottom 96 well plates. 100 µl hybridoma supernatants were added for 1 hr at 4° C. Cells were washed and positive wells were identified by FACS analysis using Goat anti Mouse-AlexaFluor 488. Cells from positive wells were cloned by limiting dilution at one cell per well and expanded first in DMEM-10% FBS containing HAT then in medium containing HT (ATCC) and later DMEM, 10% FBS. The cloned cells of interest were sent to Harlan Laboratories (Indianapolis, Ind.) for production of ascites. Antibodies were purified from ascitic fluid using proteinA-Sepharose (GE Healthcare) followed by dialysis against PBS. Aliquots were frozen at −80° C. Ig subclass of each antibody was determined by using the IsoStrip Mouse Monoclonal Antibody Isotyping Kit (Roche Applied Science). Using this approach, several hybridoma were identified that react with JAML. However, a hybridoma was identified that cross reacted with JAM-A. Thus, further specificity testing was done.

Figure 1B:
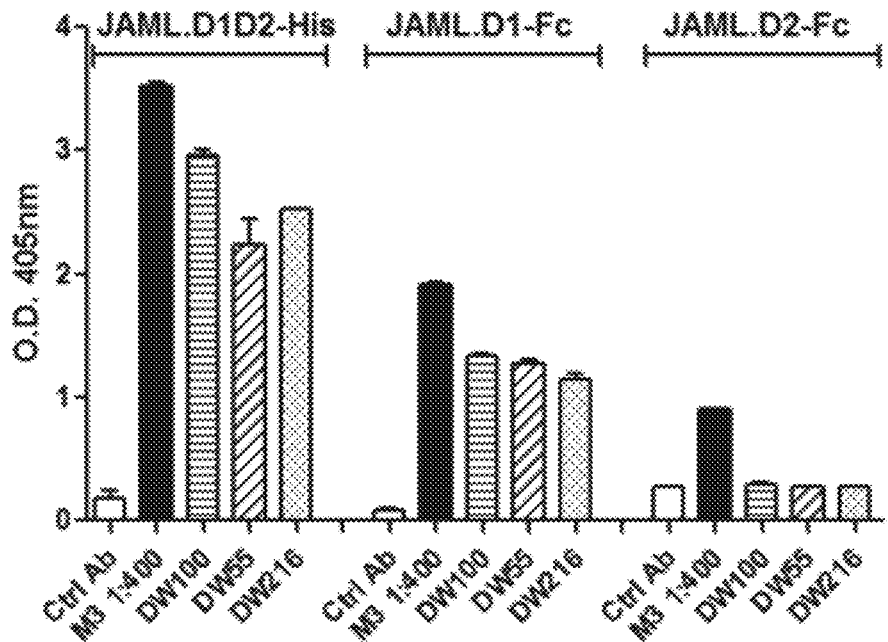
FIG. 1B. sJAML-His and purified soluble, mutant fragments of JAML, tagged with rabbit Fc (membrane distal Ig loop: sJAML.D1-Fc and membrane proximal Ig loop: sJAML.D2-Fc) were coated on Immulon II microtiter wells overnight at 4° C. After blocking and washing, antibodies were added to wells for 1 hour and the assay developed with HRP conjugated goat anti mouse Ig (H+L). After addition of ABTS, microtiter wells were analyzed in a microtiter plate reader at 405 nm wavelength. M3 is polyclonal mouse serum collected from the sJAML-His immunized mouse before the fusion. 9E10 anti Myc was used as control. The results show that specificities of the three monoclonal antibodies are directed to the membrane distal domain of JAML.

To determine the domain specificity of monoclonal antibodies, soluble full length JAML.D1D2-His (sJAML-His), truncated extracellular fragments: soluble membrane distal fragment JAML.D1-Fc (sJAML.D1-Fc), and soluble membrane proximal fragment JAML.D2-Fc (sJAML.D2-Fc), both tagged with rabbit Fc, were generated and tested for antibody binding. FIG. 1B shows that antibodies bound to sJAML.D1D2 and to sJAML.D1. Polyclonal serum (M3) was collected from the immunized mouse prior the fusion and was used as the positive control in the binding assay.

Since there is approximately a 35-45% degree of homology between human JAM proteins, antibodies were tested against other closely related divergent proteins belonging to the Ig super family (IgSF) in order to ascertain their specificity for JAML. Cross-reactivity with JAMA (Martin-Padura et al., 1998) was eliminated by staining CHO-JAMA transfectants. By ELISA, antibody binding was measured to immobilized purified soluble fragments of various IgSF receptors such as JAMC (Aurrand-Lions et al., 2000; Arrate et al., 2001), CLMP (CAR-like membrane protein (Raschperger et al., 1997)), CAR (Bergelson et al., 1997), EVA1 (Chatterjee et al., BBRC 2008, 372(2) 412-417) and SIRPA (van Beek E. M, et al., 2005 J. Immunol. 175, 7781-7787).

As can be seen in Table 1, the DW100, DW55 and DW216 reacted with exquisite specificity to JAML. Purified recombinant fusion proteins were coated on Immulon II 96 well microtiter wells at 5 µg/ml in TBS. Microtiter wells were blocked with 5% Roche blocking reagent, washed and antibody solutions were added at 10 µg/ml in TTBS/5% blocking reagent for 1 hour RT. After washing, HRP conjugated goat anti Mouse (Light chain specific) was added for 1 hour RT, washed again followed by color development with ABTS and OD measurement.

TABLE 1

Specificity of Antibodies for JAML and not other IgG superfamily members

|  | DW100 | DW55 | DW216 |
| --- | --- | --- | --- |
| BSA | − | − | − |
| JAML-Fc | +++ | ++ | ++++ |
| JAMA-Fc | − | − | − |
| JAMC_Fc | − | − | − |
| CLMP-Fc | − | − | − |
| Fc only | − | − | − |
| JAML-His | ++++ | +++ | ++++ |
| EVA-His | − | − | − |
| SIRPA-HIS | − | − | − |
| CAR-GST | − | − | − |
| JAMA-GST | − | − | − |

Figure 1C:
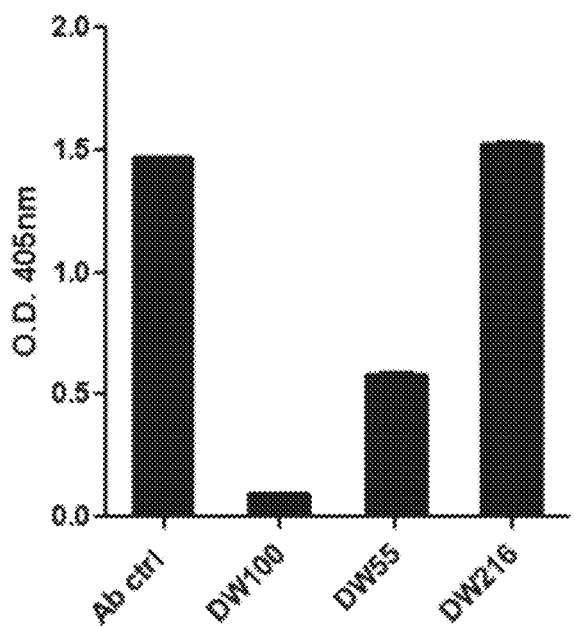
FIG. 1C. CAR binding assay: sJAML-His was coated in Immulon II microtiter microtiter wells overnight, at 4° C. Microtiter wells were washed and blocked and 100 µl antibody solutions were added to wells for 1 hour RT. After washing, CAR-GST was added at 10 µg/ml for 1 hour RT, washed and the assay was developed with HRP conjugated goat anti GST followed by ABTS and OD measurement at 405 nm. DW100 completely inhibited CAR binding to JAML, DW55 partially inhibited binding and DW216 did not inhibit at all.
Figure 1D:
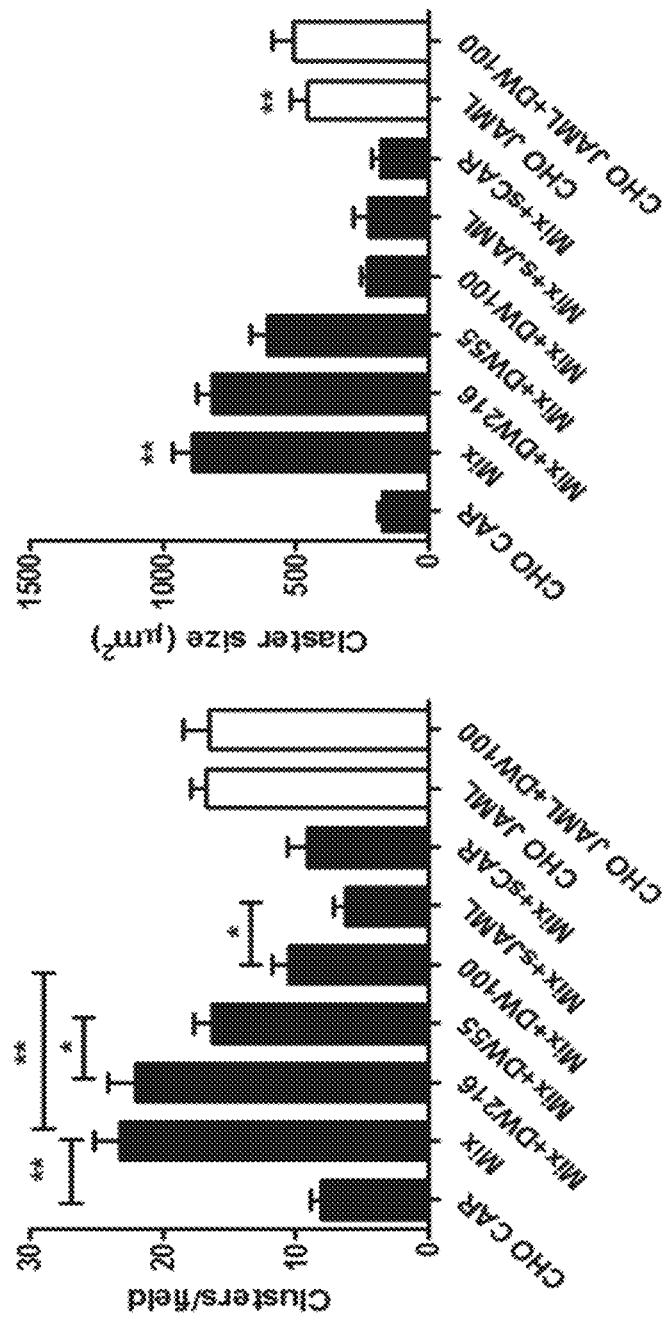
FIG. 1D. CHO-K1 cells stably transfected with either JAML (CHO-JAML) or CAR (CHO-CAR) proteins were allowed to aggregate (1 hour at 37° C. on a shaker at 50 RPM) separately (1×10$^6$ cells/BSA coated 3 ml Petri dish), or as a mix (5×10$^5$ each cell type/dish), in the absence or presence of anti-JAML monoclonal antibodies DW100, DW55 and DW216 (30 μg/ml). The number of clusters (left) and the area of the clusters (right) were quantified in 7 randomly chosen fields using light microscopy. The results are representative of four independent experiments. CHO-CAR and CHO-JAML in mixed cultures formed large aggregates. This could be blocked with DW100 (blocks JAML-CAR binding) and to some degree with DW55 but not DW216, suggesting that JAML-CAR binding results in aggregation of CHO-K1 cells. * significantly different from each other ($p<0.05$), ** ($p<0.01$).

Because certain antibodies recognize the membrane distal domain of JAML, their ability to inhibit binding to CAR was tested. By ELISA, the levels of soluble CAR-GST bound to immobilized sJAML-His preincubated with anti JAML antibodies was measured. As shown in FIG. 1C, DW100 completely inhibited binding of JAML to CAR, DW55 partially inhibited and DW216 did not inhibit at all. Thus, these antibodies recognize three different epitopes on JAML and that both DW100 and DW55 bind epitopes close to the JAML binding site. Using a cell aggregation assay, the possibility that DW100 could inhibit the binding of JAML to CAR expressed on the surface of cells was examined. As seen in FIG. 1D, stable transfectants of CHO cells expressing either CAR or JAML on their surface were mixed in culture and numerous clusters were observed to form. DW100 but not DW216 significantly decreased both the size and the number of formed clusters in the mixed cultures compared to those in cultures of CHO-CAR or CHO-JAML alone. Aggregation of CHO-CAR and CHO JAML cells was also blocked by the addition of either soluble JAML or soluble CAR. This again confirms previously described JAML binding to CAR, as well as the specificity of DW100 (blocking) and DW216 (non-blocking) Abs to JAML. Interestingly, increased cluster formation was observed in cultures of CHO-JAML alone, suggesting a possible JAML JAML interaction.

Example 2

JAML Expression on PMN and Cell Lines

Figure 2A:
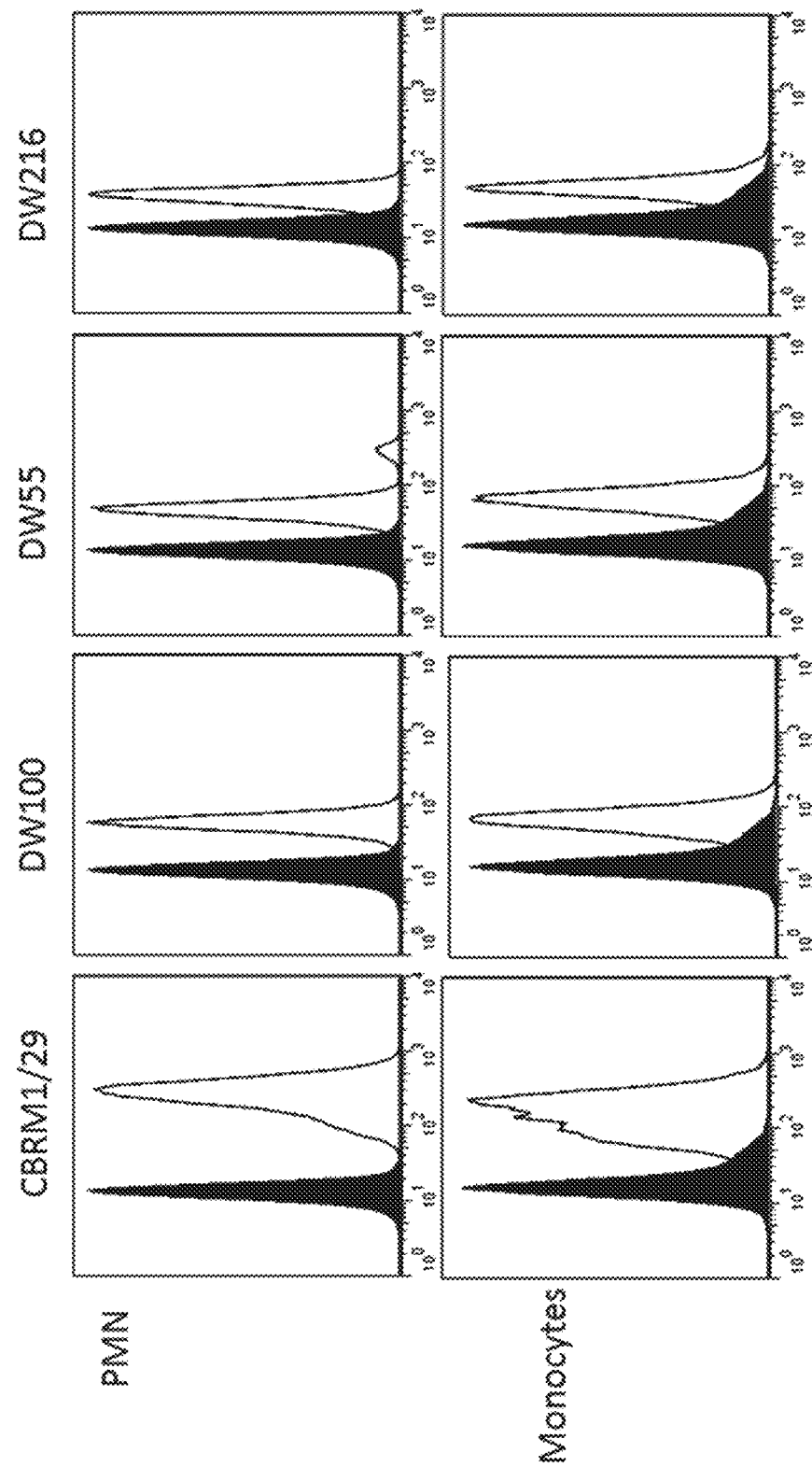
FIG. 2A shows data suggesting JAML expression in primary cells and cell lines. PMN and monocytes were isolated and purified from whole blood of healthy donors, incubated on ice with either control anti Myc (9E10, solid histograms), anti-CD11b/Cd18 (CBRM1/29) or purified anti-JAML antibodies at 5 μg/ml, followed by Alexa Fluor 488 conjugated goat anti Mouse antibody. JAML surface expression was analyzed by flow cytometry.
Figure 2B:
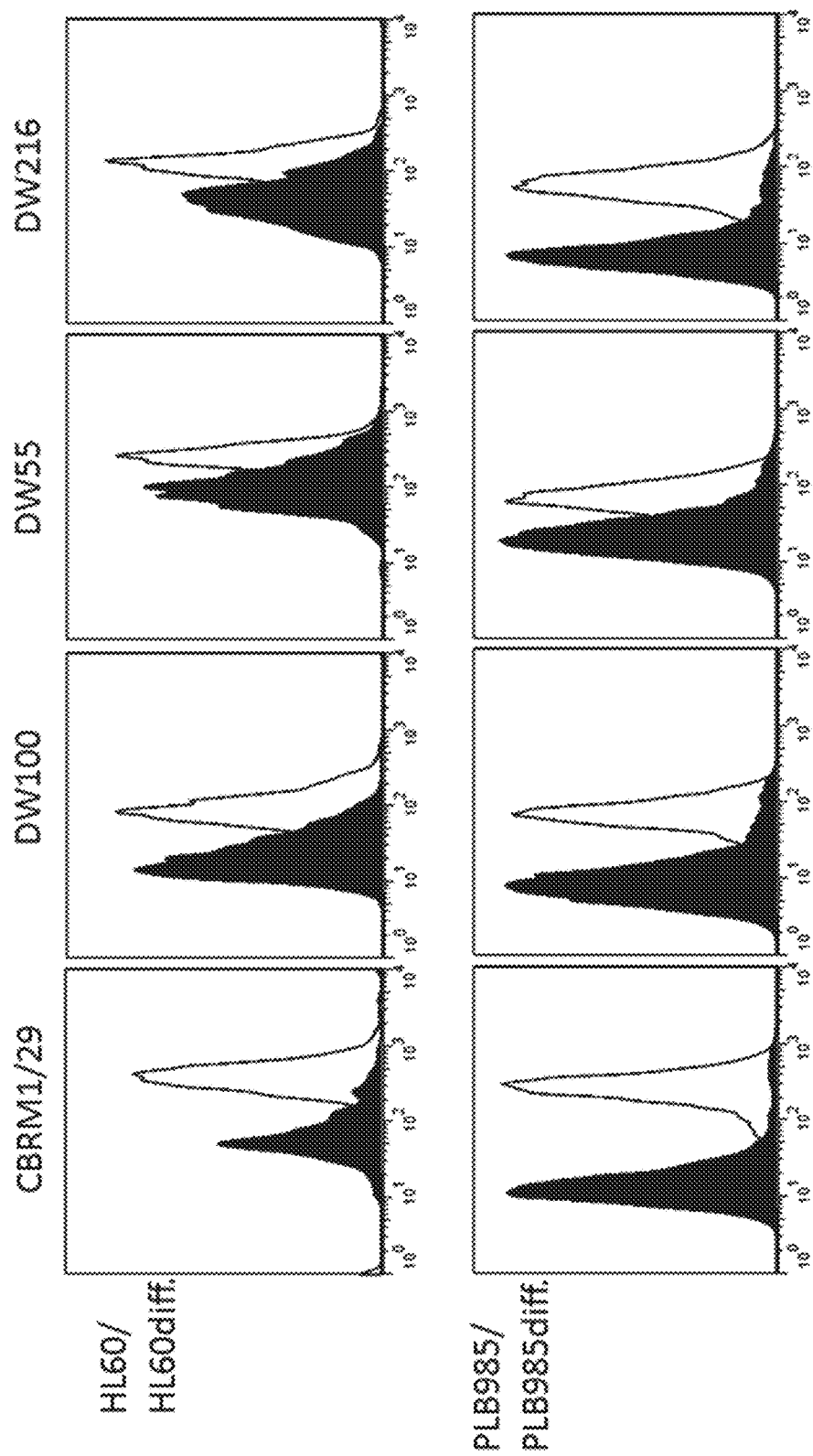
FIG. 2B. Staining of HL60 and PLB985, non-differentiated (solid histograms) and differentiated for 6 days with DMSO (line histograms). The staining shows upregulation of surface JAML during differentiation.
Figure 2C:
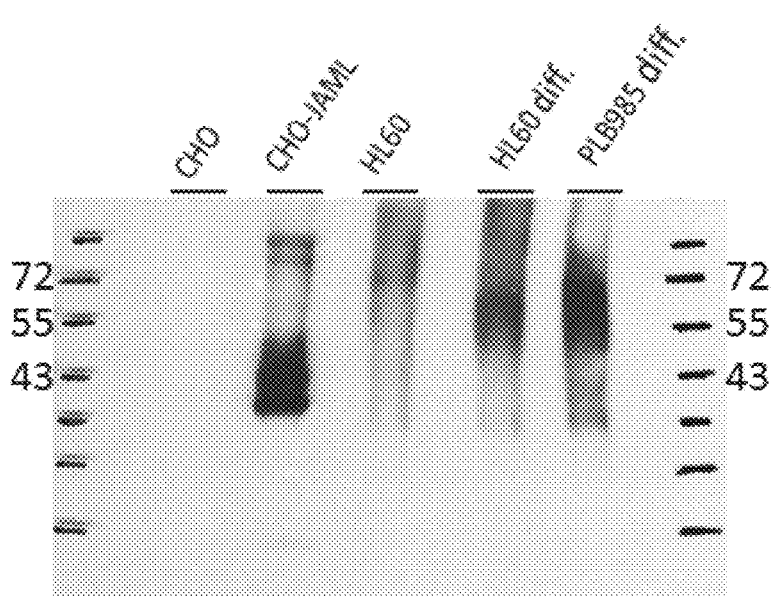
FIG. 2C. Cells were biotinylated prior lysis in RIPA buffer with protease inhibitors. IP was performed with a DW216-sepharose conjugate, samples were eluted by boiling in non-reducing sample buffer and applied to 4-15% acrylamide gel, transferred to PVDF membrane and probed with streptavidin-HRP followed by ECL. A wide band is visible in differentiated cell lysates, at approximately 55 to 60 KD

Using anti JAML monoclonal antibodies JAML expression was detected on freshly isolated PMN and blood monocytes (FIG. 2A) (Luissint et al., 2008, JCB 183 No6 1159-1173). We further extended these observations to neutrophil-like cell lines, HL60 (a promyeloblast cell line) and the subclone of HL60, PLB-985. As seen in FIG. 2C, when undifferentiated, both cell lines expressed JAML at very low levels but the expression was significantly increased during differentiation. The expression of CD11b/CD18 was also increased during differentiation as detected with mAb CBRM1/29. Since our monoclonal antibodies revealed no band by Western blotting, in order to identify the size of JAML protein in cell lysates of HL60, PLB-985 and PMN, cells in suspension were biotinylated and lysates probed by immunoprecipitation with our antibodies that had been covalently linked to Sepharose beads. The streptavidin blot revealed a wide band around 55-60 kD in the lysates of PMNs and differentiated HL60 as well as PLB-985 (FIG. 2C). It was barely visible in non-differentiated cell lysates. Interestingly, the band obtained from the lysate of CHO-JAML-His transfectants appeared to be lower, around 45 KD, which is likely due to differential glycoforms of JAML.

Example 3

JAML Expression During PMN Transmigration

Figure 3A:
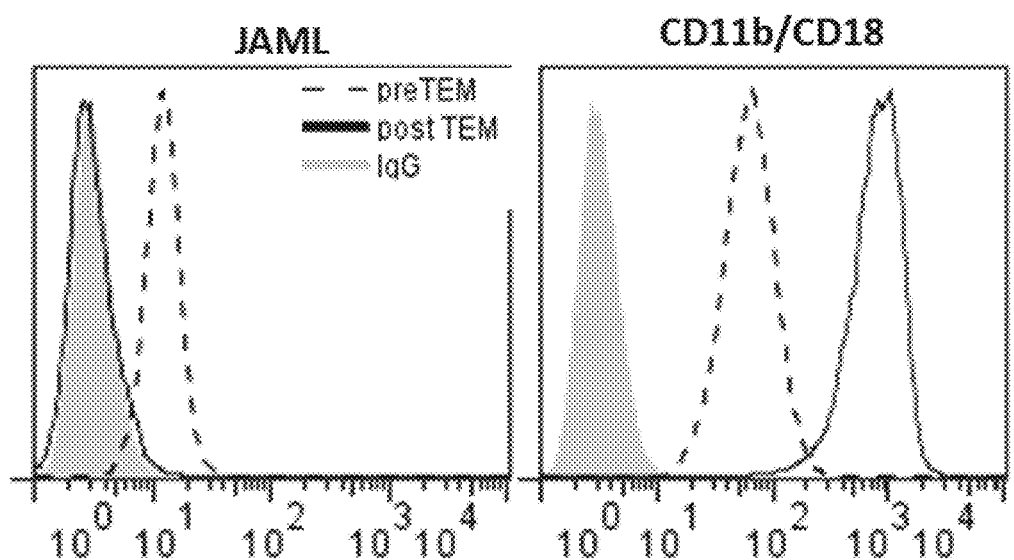
FIG. 3A shows data suggesting PMNs shed JAML during transepithelial migration. Freshly isolated PMN were either immediately fixed with 1% paraformaldehyde (PFA) or allowed to migrate across T84 epithelial cells into wells coated with poly 2-hydroxyethylmethacrylate (to prevent transmigrated PMN from adhering to the well), followed immediately by fixation with 1% PFA. PMN were then stained for JAML (DW100) and CD11b/CD18 (CBRM 1/29) and analyzed for surface expression by flow cytometry.

JAML interaction with epithelial CAR plays a role in PMN transepithelial migration (Zen et al., 2005, Mol. Biol. Cell, Vol 16, 2694-2703). In that study, JAML-Fc fusion protein was reported to partially block PMN transepithelial migration. Interestingly, highly specific mAb DW100 only had a small inhibitory effect (~15%). To further investigate this and to further define the role for JAML in PMN transepithelial migration (TEM), JAML expression was examined on PMN during transepithelial migration. PMN were allowed to migrate across epithelial cells (T84/Caco2) in the physiologically relevant basolateral to apical direction towards an fMLF gradient into wells coated with poly 2-hydroxyethylmethacrylate (to keep PMN in suspension). Transmigrated PMN were collected, stained for JAML using two different monoclonal antibodies and analyzed by flow cytometry (FIG. 3). Surprisingly, after transmigration, surface expression of JAML on PMNs was completely lost. At the same time, CD11b/CD18 expression was dramatically increased, which is indicative of PMN activation (FIG. 3A). The loss of JAML in post-migrated PMNs was also confirmed by immunofluorescence.

Figure 3B:
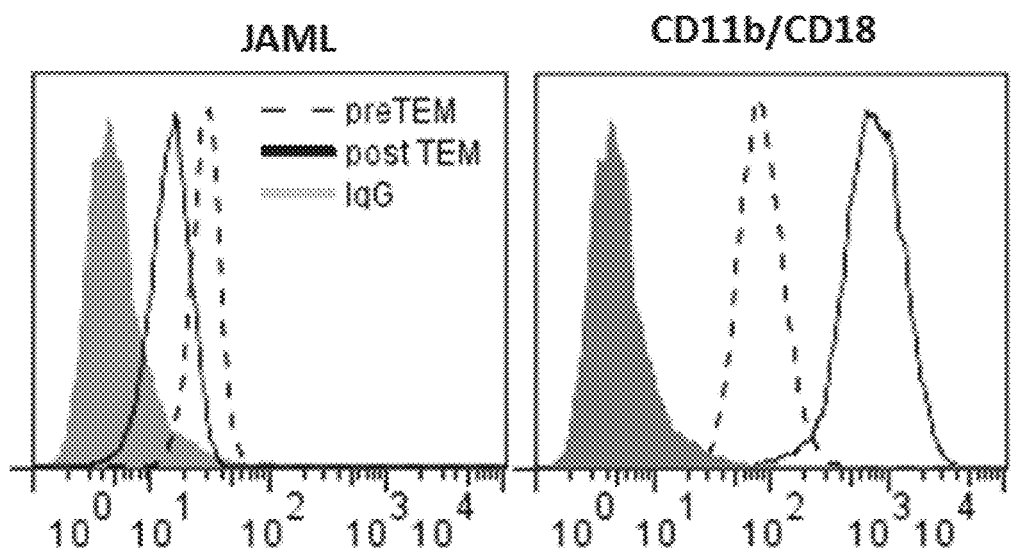
FIG. 3B shows data for endothelial cells (HDMVEC).
Figure 3C:
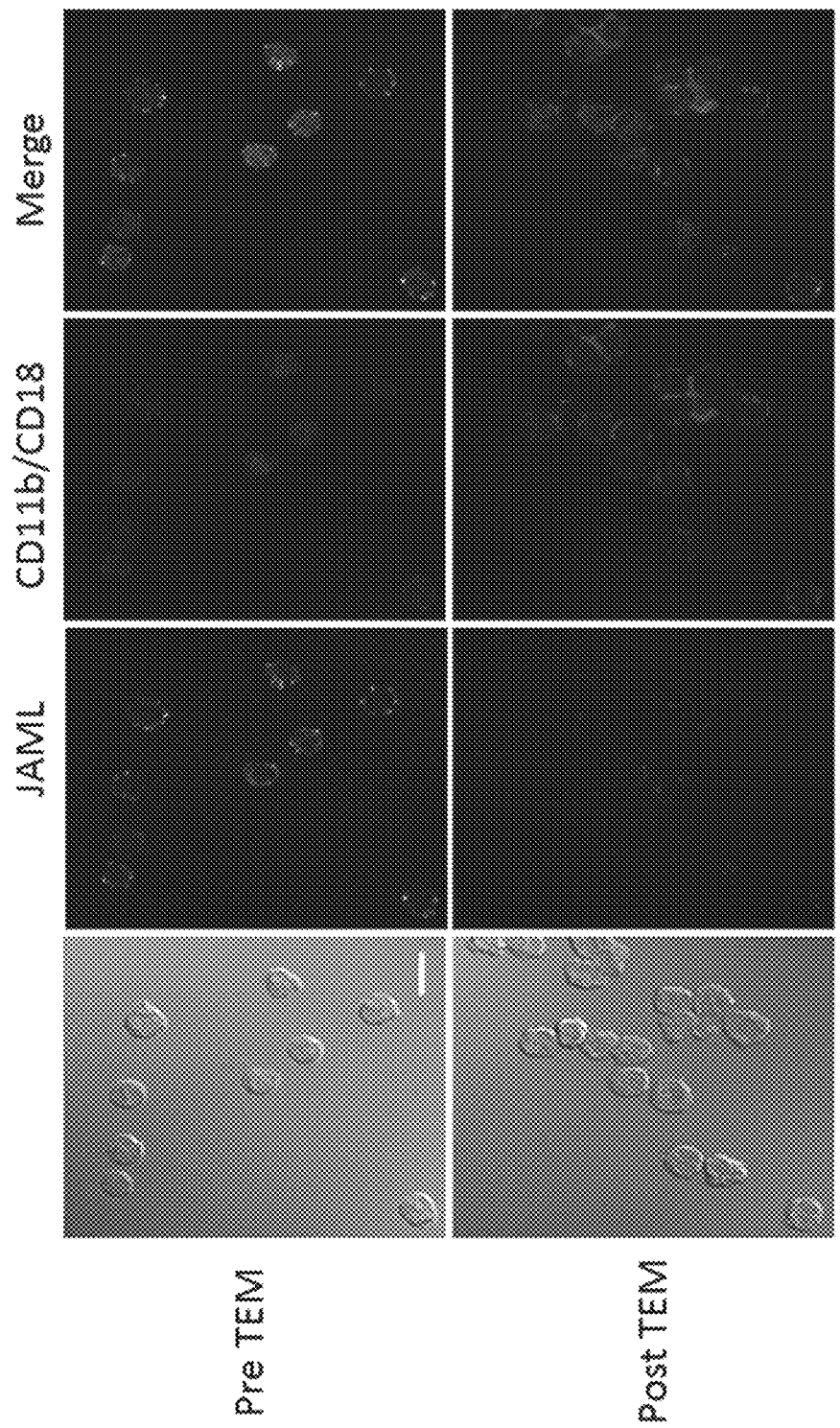
FIG. 3C shows representative images of PMN before (upper panel) and after (bottom panel) transepithelial migration. A complete loss of surface JAML can be seen in post-migrated PMN. All micrographs are representatives of 5 independent experiments. The scale bar is 10 μm.

As shown in FIG. 3C, PMN prior to TEM stained strongly for JAML (upper panel), in contrast, post TEM, PMNs lost staining for JAML, but exhibited a concomitant increase in CD11b/CD18 expression. Zen et al., Mol. Biol. Cell, 2005, 16(6):2694-2703 reported increased staining of activated PMN using a polyclonal anti JAML antiserum. However, as discussed above, some of the antibodies generated against recombinant JAML revealed cross reactivity with other JAM proteins raising the likelihood of cross reactivity with other cell surface molecules with polyclonal anti-JAML antiserum.

Since prior to transepithelial migration PMNs exit the blood vessels, whether JAML expression on PMNs would be preserved during migration across endothelial cells (HDMECs) towards a 10 µM fMLF, as described previously was evaluated. Indeed under similar conditions only a small portion of surface JAML was lost, but most of it was still detectable on PMN surface (FIG. 3B). Interestingly, PMN treatment with 10 µM fMLF had no significant effect on JAML expression, suggesting that the observed small decrease in JAML expression was induced by PMN-endothelial cell contact.

Example 4

Loss of JAML Upon PMN Activation

Figure 4A:
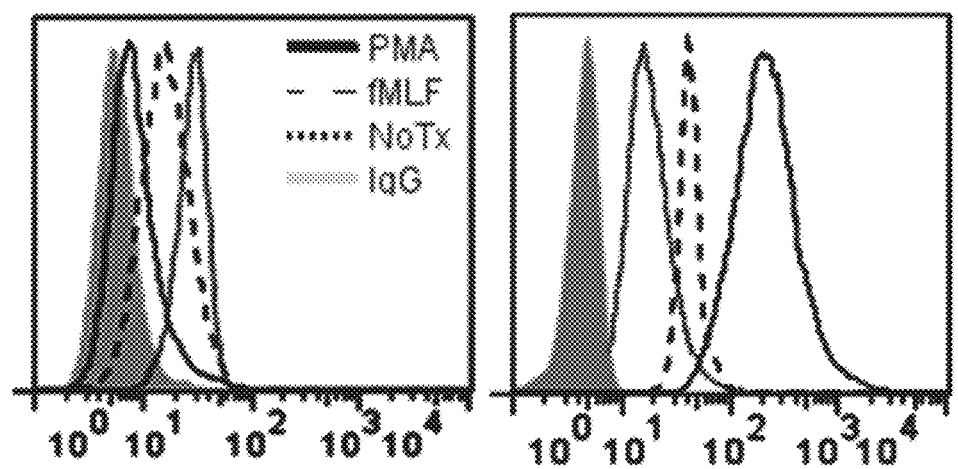
FIG. 4A shows data suggesting PMNs shed JAML upon activation, and the loss of JAML correlates to the degree of PMN activation. Freshly isolated PMN, not treated (No Tx), or treated with either fMLF (100 nM) or PMA (200 nM) in suspension for 15 minutes at 37° C. were fixed with 1% paraformaldehyde, stained for JAML (DW100) and CD11b/CD18 (CBRM 1/29) and analyzed for surface expression by flow cytometry. PMN activation with fMLF (as indicated by the increased expression of CD11b/CD18, right panel) resulted in partial loss of JAML (left panel). A higher degree of activation caused by PMA resulted in a complete loss of surface JAML.
Figure 4B:
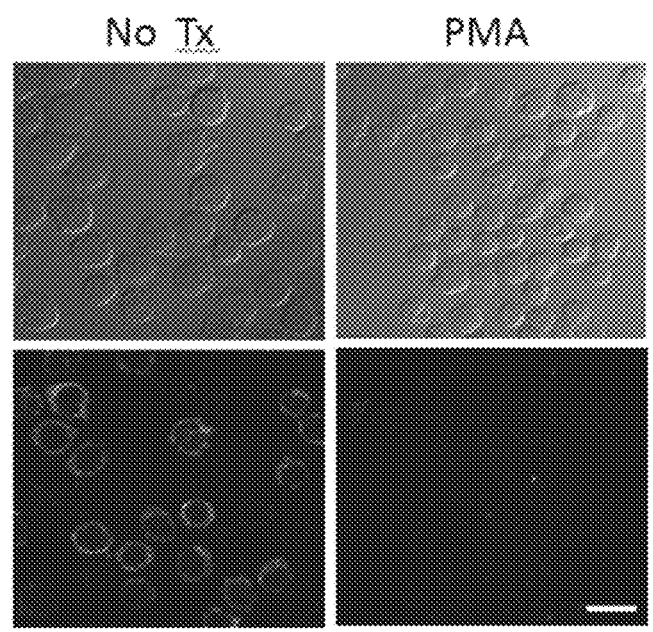
FIG. 4B. Representative images of PMN untreated (No Tx), or treated with PMA that were immunofluorescently labeled for JAML (DW100). Loss of JAML is apparent after PMA treatment.
Figure 4C:
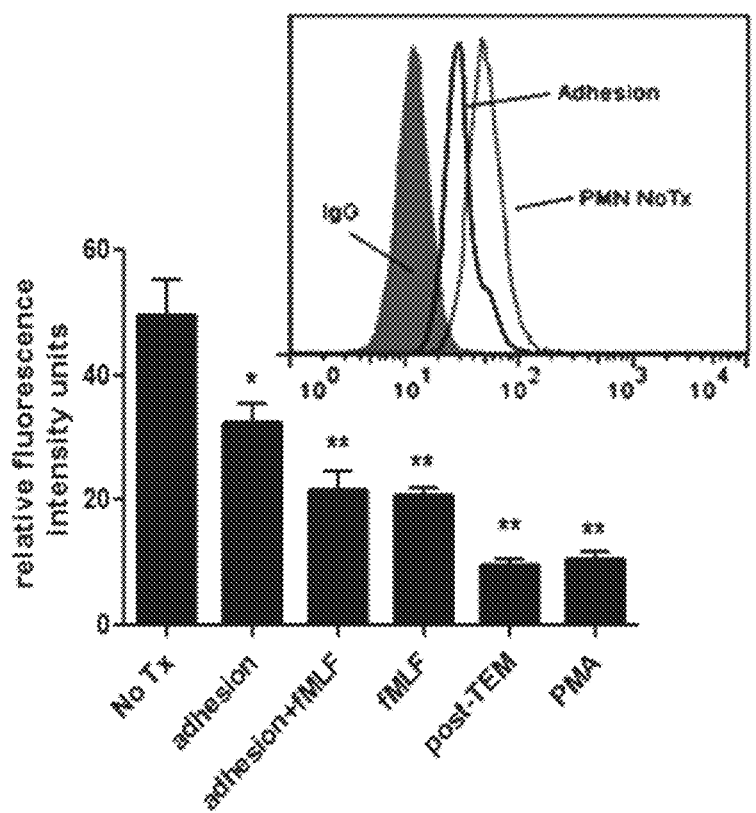
FIG. 4C. JAML expression on PMN as measured by flow cytometry under the given conditions. JAML expression after adhesion to epithelial cells was measured. N=4 independent experiments. The insert is a representative flow diagram where loss of JAML can be seen after adhesion to epithelial cells in the absence of other stimulus.
Figure 4D:
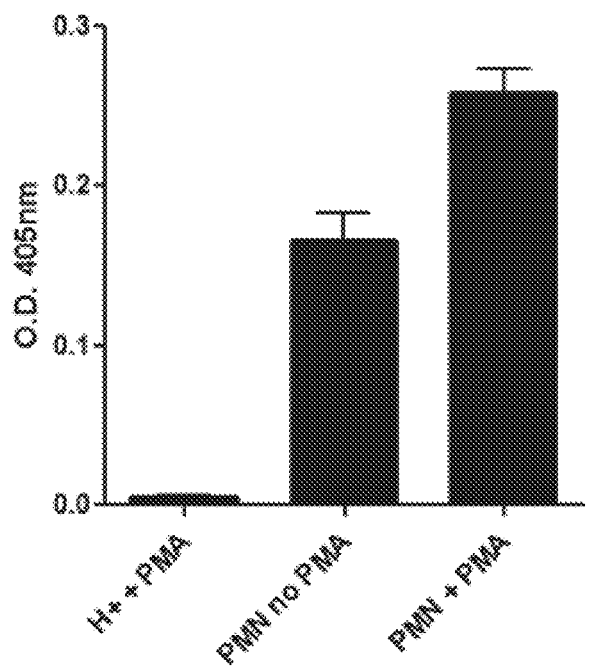
FIG. 4D. Freshly isolated PMN were washed in Hanks solution with Ca++ and Mg++ (H+) at $25\times10^6$ cells per condition and resuspended in 350 μl H+ alone or H+ containing 200 nM PMA followed by 30 minutes incubation at 37° C. Soluble JAML was detected in sandwich ELISA: briefly, Immulon II microtiter wells were coated with DW100 (10 μg/ml) overnight at 4° C. The supernatants were applied in triplicates to the wells (100 μl/well) and incubated for 1 hour at RT. After washing, microtiter wells were incubated with biotinylated DW216 (100 μl at 10 μg/ml) for 1 hour at RT, followed by HRP conjugated streptavidin, ABTS and OD measurement.

Increased expression of CD11b/CD18 during TEM is suggestive of PMNs activation. Thus whether PMN activation alone is sufficient to induce the loss of surface JAML or whether direct contact with the epithelium is required was examined. To test this, the expression of JAML was analyzed on PMNs that were stimulated in suspension with fMLF (100 µM) and PMA (200 nM). PMNs were allowed to adhere to epithelial cells for 1 hour. The loss of JAML could be correlated to the degree of PMN activation. As shown in FIG. 4A, treatment with 100 µM fMLF, unlike treatment with 10 µM, resulted in partial but significant loss of JAML (FIG. 4). Moreover, treatment with PMA (200 nM), a more potent activator (confirmed by the increase in the expression of CD11b/CD18 in FIG. 3 and FIG. 4A) induced a complete loss of surface JAML from PMNs (FIG. 4 A). This was again confirmed by immunofluorescence (FIG. 4B). PMN adhesion to epithelium in the absence of proinflamatory stimulus (as measured by flow cytometry, gating on Mac-1 positive PMNs) was also sufficient to induce a partial loss of surface JAML (FIG. 4C), in agreement with the small loss of surface JAML observed after migration through endothelial cells (FIG. 3B). Thus data shows that the loss of JAML can be induced independently of interactions with the epithelium, however, the contact with epithelial/endothelial cells during PMN migration contributes to PMN activation and loss of JAML. The loss of JAML from PMN surface under the conditions described above is summarized in FIG. 4C. Next, the observed loss of JAML during PMN activation may be due to its shedding from PMN surface and thus would be detectable in the supernatant of activated cells. To test this hypothesis, two antibodies, DW100 and DW216 that recognize two different epitopes of JAML were used in a sandwich ELISA assay to capture solubilized molecules in the supernatant of activated PMN. Low amounts of JAML were detected in the supernatant of activated PMN as seen in FIG. 4D.

Figure 5A:
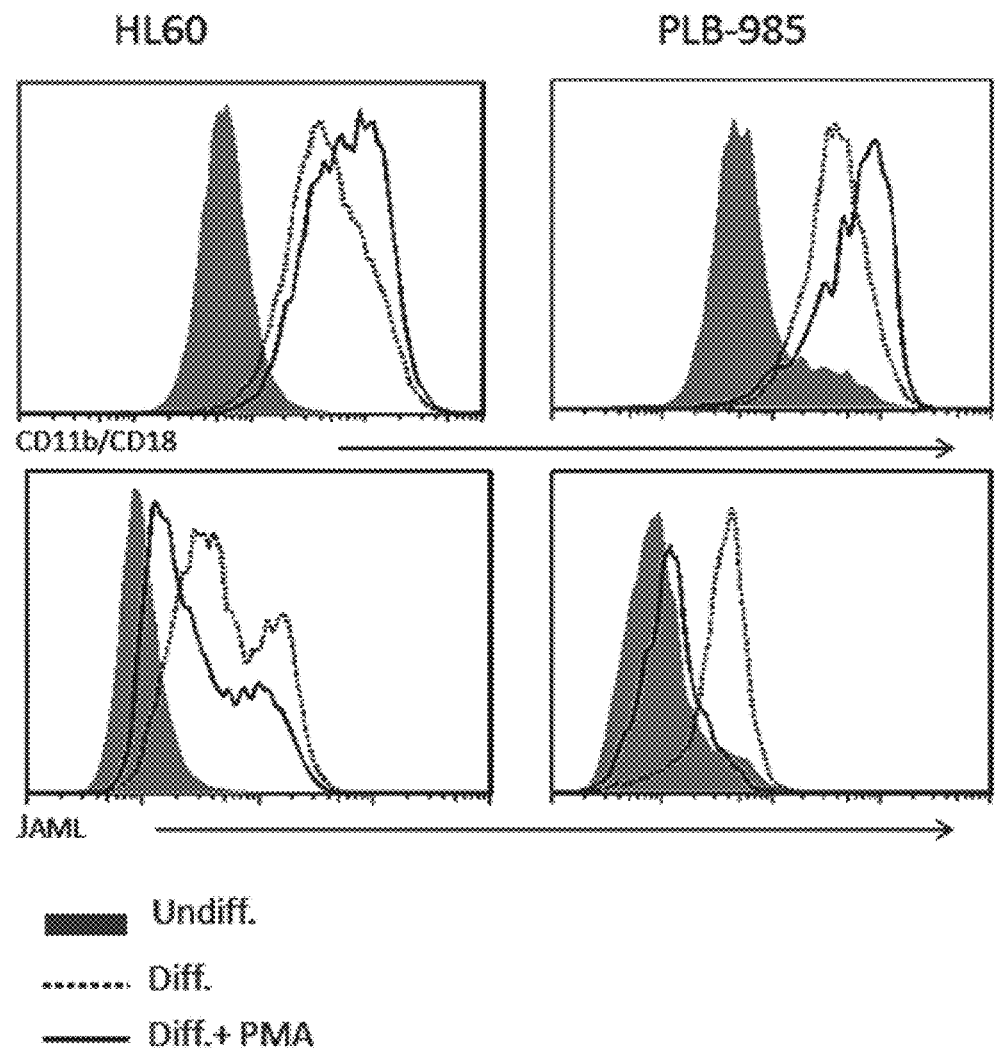
FIG. 5A shows data suggesting JAML shedding by differentiated HL60 and PLB985 upon activation. Both HL60 and PLB985 (non-differentiated and differentiated) were washed in Hanks solution with $Ca^{++}$ and $Mg^{++}$ ($H^+$) at $30\times10^6$ cells per condition and resuspended in 350 μl $H^+$ or $H^+$ containing 200 nM PMA followed by 30 minutes incubation at 37° C. A cell aliquot was set aside for flow cytometry and cells were stained with monoclonal CBRM1/29 (CD11b/CD18) or DW100 anti JAML followed by Alexa Fluor 488 conjugated goat anti mouse antibody.
Figure 5B:
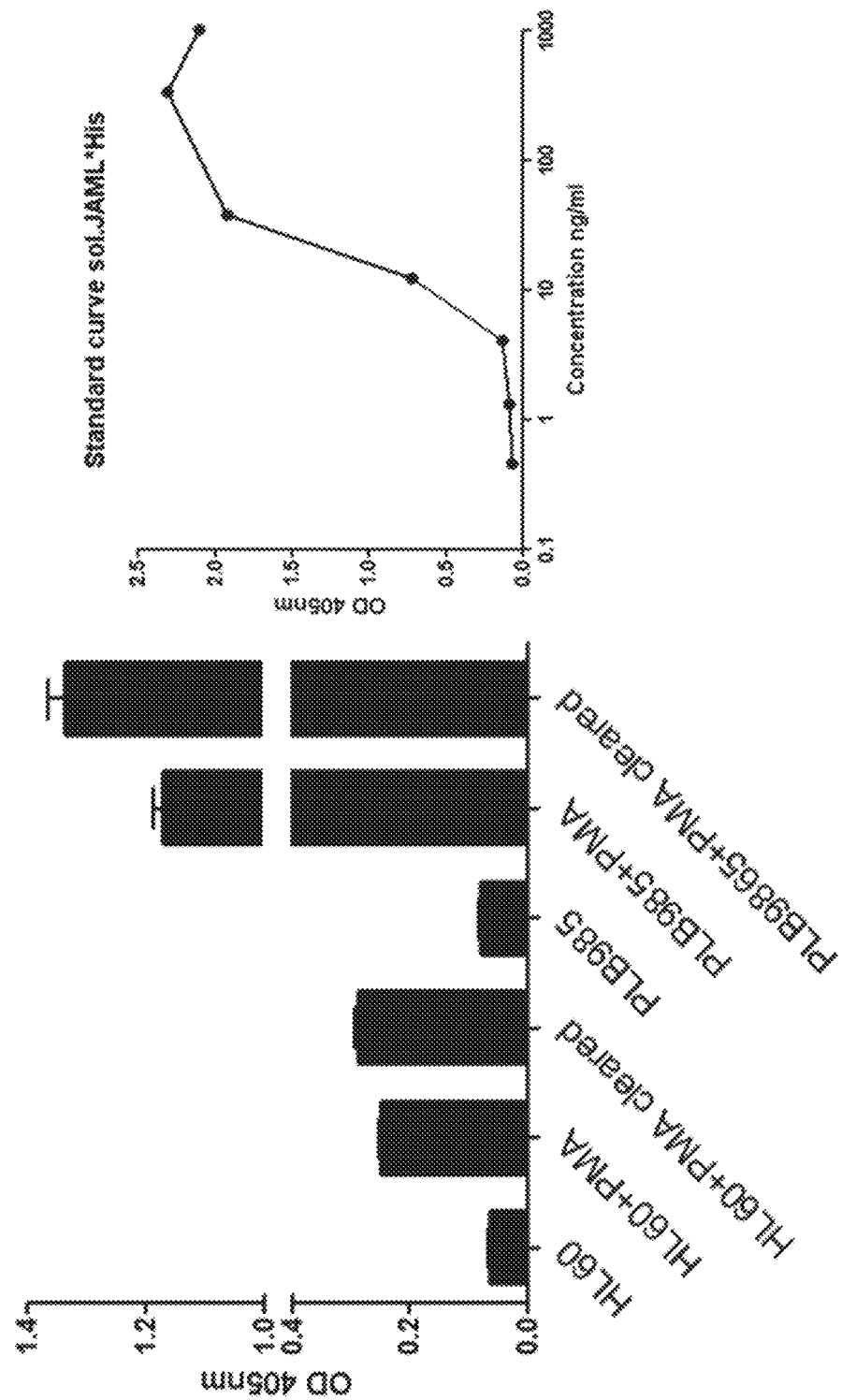
FIG. 5B. After incubation in presence or absence of PMA, cells were pelleted and supernatants collected by centrifugation. To clear the supernatants of microparticles, supernatants were subjected to ultra-centrifugation (100,000×g), prior assaying for the presence of soluble JAML. Soluble JAML was detected in sandwich ELISA as described in FIG. 4. For standard curve, soluble JAML-His generated in HEK 293T cells and purified over a nickel column was diluted serially and 100 μl applied to DW100 coated wells. Assay was conducted as described in Materials and Methods.
Figure 5C:
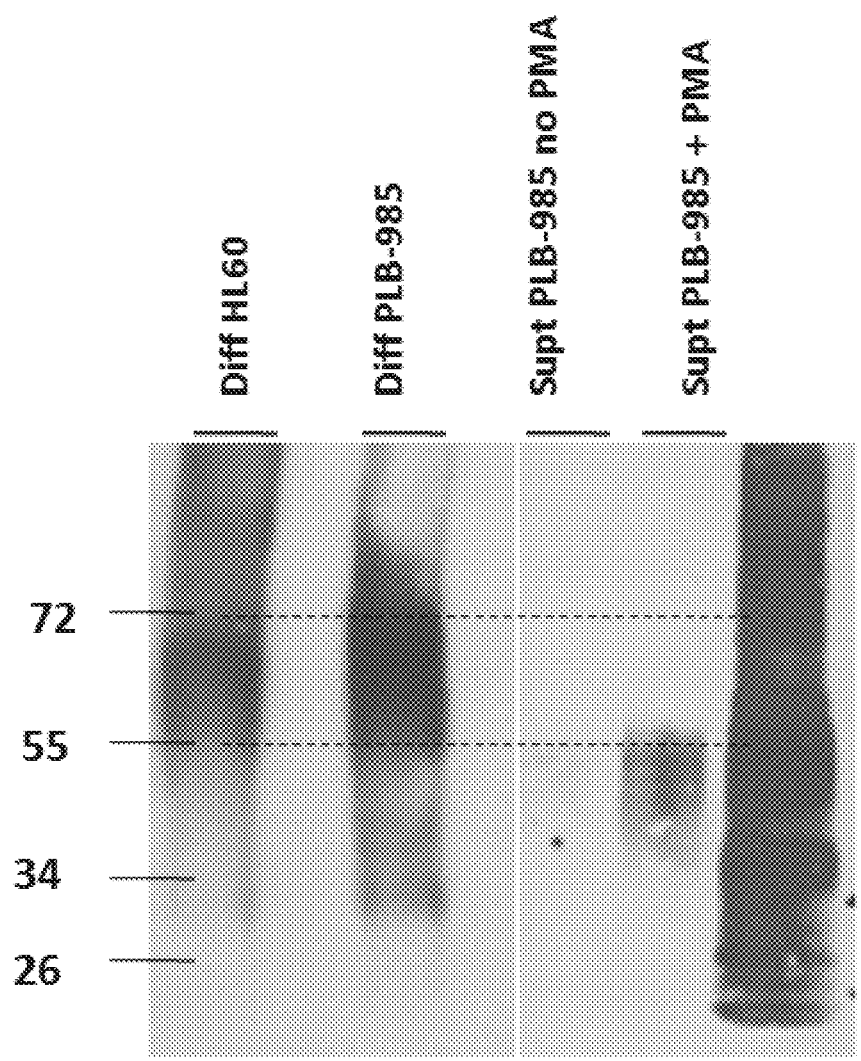
FIG. 5C. Immunoprecipitation of JAML from biotinylated PMA-treated cells. Supernatants of PMA treated cells were collected as described in panel B and IP was performed with DW216-sepharose conjugate from both cell lysates and supernatants. JAML shed in the supernatant of PMA treated PLB-985 is identified by a wide band between 45-55 KD and suggests that it represents a majority of the extracellular domain of JAML.

The findings of JAML shedding were extended to both HL-60 and PLB-985 cell lines. Similarly to PMNs, PMA activation of both cells resulted in a complete loss of surface JAML (FIG. 5A) with concomitant upregulation of CD11b/CD18. Furthermore, significant amounts of soluble JAML were measured in the supernatant of these cells in the ELISA capture assay as seen in FIG. 5B. Upon activation, human neutrophils release microparticles, called ectosomes, directly from the cell surface and that ectosomes are implicated in the inflammatory response (Eken et al., 2008, J. Immunol. 180, 817-824). To test whether JAML molecules were released in microparticles, supernatants from activated cells were subjected to ultracentrifuge (100,000×g). The "cleared" supernatant was used in our capture ELISA assay and did not show any decrease in the amount of JAML present as seen in FIG. 5B. Thus, JAML is indeed shed into the medium upon PMN activation as a soluble molecule. JAML was identified by Western blot in the supernatant of differentiated PLB-985 and HL60 treated with PMA as a ~45 KD band suggesting that the shed molecule represents a majority of the entire ectodomain of JAML (FIG. 5C).

Example 5

Shedding of JAML Ectodomain is a Zinc Metalloprotease-Dependent Process

Figure 6A:
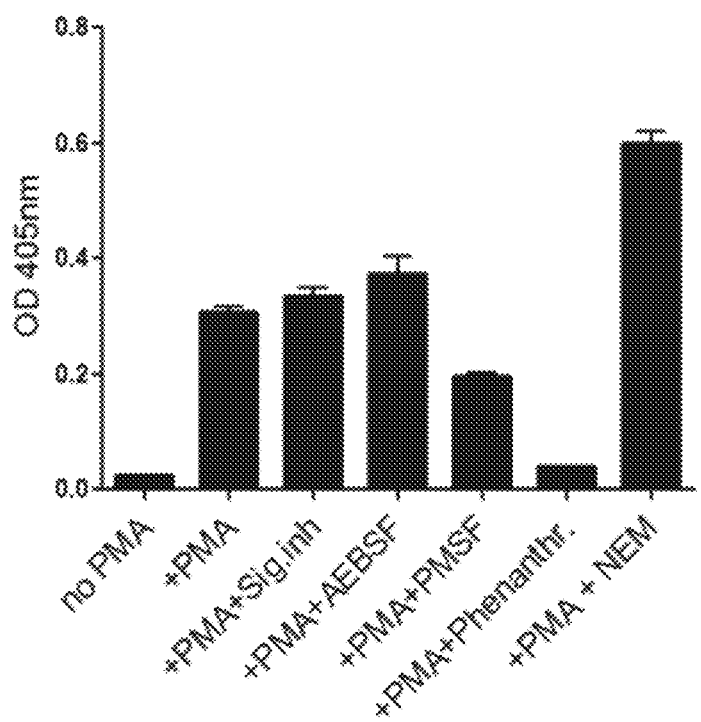
FIG. 6A shows data suggesting $Zn^{++}$-dependent Metalloprotease control the shedding of JAML. JAML shedding from differentiated HL60 was assayed as described in the legend for FIG. 5. Protease inhibitors were added to cell suspensions during incubation in H' with or without PMA Inhibitors used were Sigma inhibitor cocktail (Cat #P8340) used at 1:50 dilution, AEBSF 1 mM, PMSF 2 mM, Phenanthroline 5 mM and NEM 6 mM.
Figure 6B:
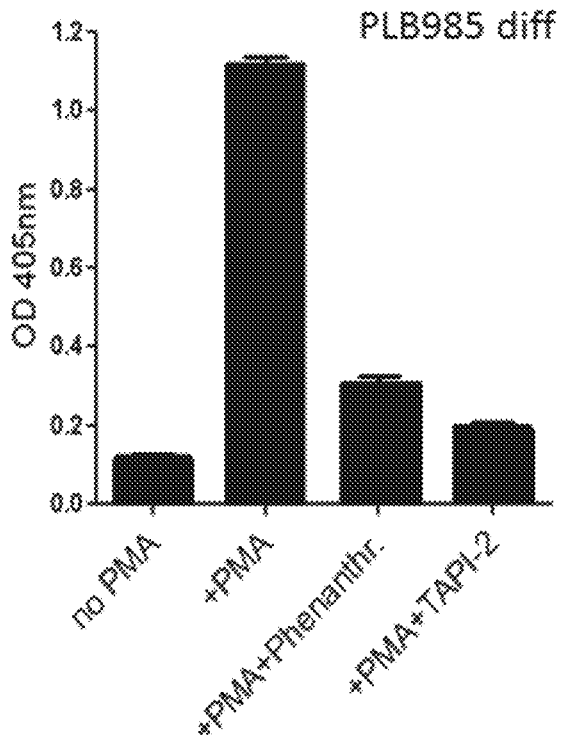
Figure 6C:
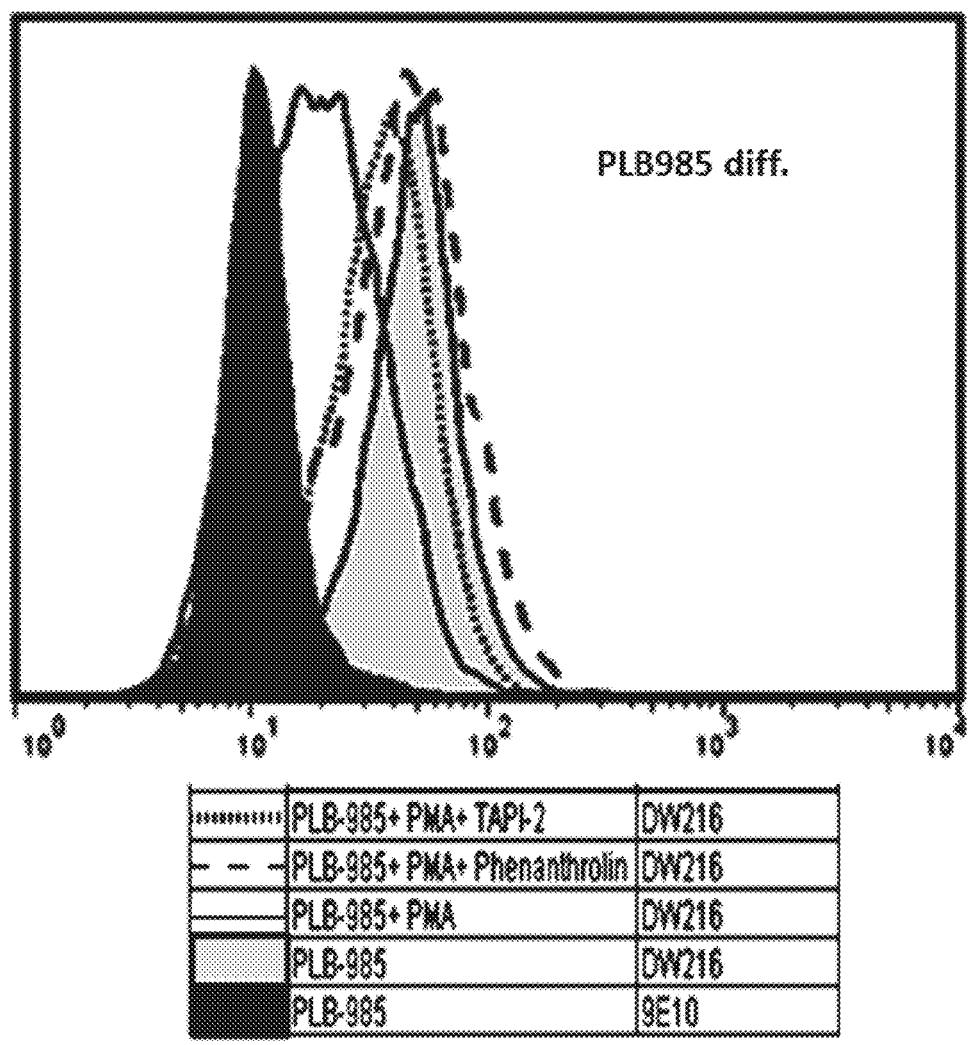

To explore the mechanisms for release of JAML from the surface of differentiated HL60 and PLB-985 cells during activation with PMA, PMA was added to cells in the presence or absence of a variety of protease inhibitors. The protease inhibitor cocktail from Sigma that targets serine proteases was used as well as cysteine proteases and several independent inhibitors. No decrease in JAML shedding was observed with the Sigma protease inhibitor cocktail, AEBSF (inhibits thrombin and other serine proteases) or N-Ethyl maleimide (inhibits cysteine proteases). While PMSF showed some inhibition, these results are most likely due to toxic effects since AEBSF had no effect. However, phenanthroline, an inhibitor of zinc metalloproteinases, completely inhibited this process (FIG. 6A). Zinc-dependent metalloproteinases have been shown to be active at the surface of CHO cells upon stimulation with PMA. (Le Gall et al., 2003, JBC 278 No46 45255-45268). CHO-JAML-His transfectants cells were stimulated with PMA in the presence or absence of Phenanthroline or TAPI-2, both are specific inhibitors of Zn++ dependent metalloproteinases and strongly inhibited JAML release due to PMA activation. The specificity of the shedding inhibition was confirmed in other cell lines, as seen in FIG. 6B, with PLB-985 using a very specific inhibitor TAPI2. This inhibition was also verified by FACS staining with DW216 antibody as seen in FIG. 6C: in the presence of inhibitors, the level of JAML retained at the cell surface after PMA activation is the same level of non-activated cells whereas it is significantly lower in the absence of inhibitors

Example 6

Soluble JAML Binding to Epithelial CAR

Figure 7A:
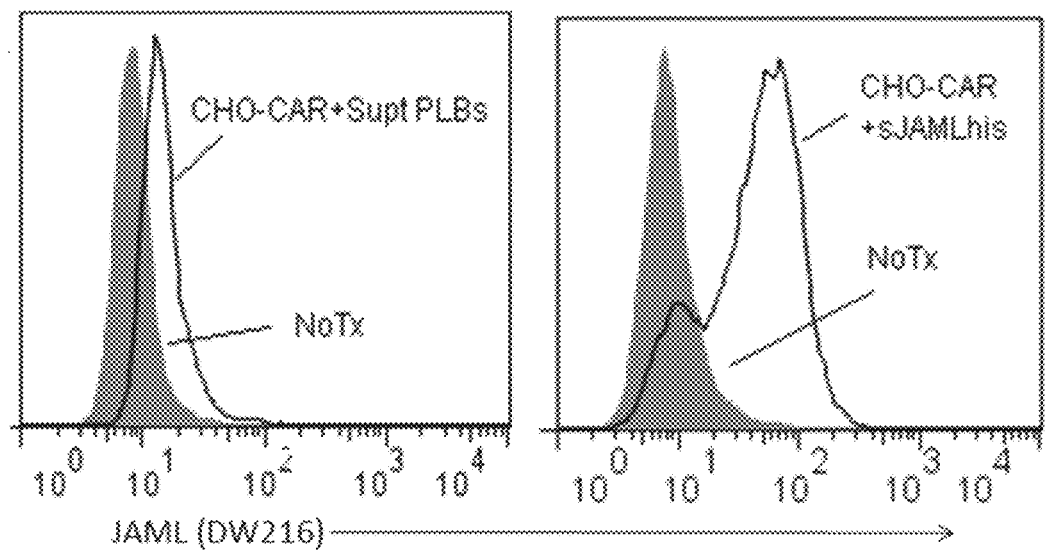
FIG. 7A shows data suggesting soluble JAML binds to CAR. CHO-K1 cells stably expressing CAR (CHO-CAR) were incubated with supernatants from PMA activated PLB cells ($5\times10^7$ cell activated in 1 ml, left panel) or recombinant soluble JAML-His (sJAML, 20 μg/ml, right panel) for 1 h at 4° C. JAML binding to CAR on the cell surface was measured by flow cytometry and compared to CHO-CAR cells alone (NoTx). The flow micrograph is representative of 4 independent experiments.
Figure 7B:
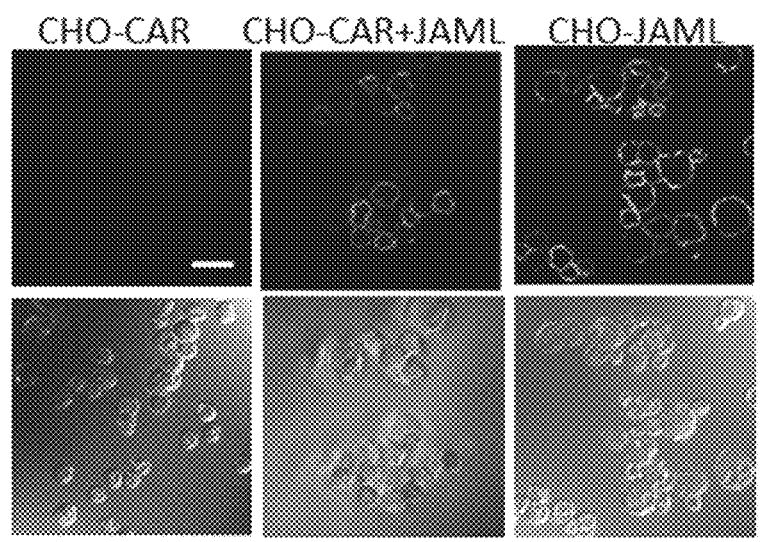
FIG. 7B. Representative images depict JAML binding to CAR expressed on CHO cell surface as confirmed by immunofluorescence and confocal microscopy. The scale bar is 10 µm.
Figure 7C:
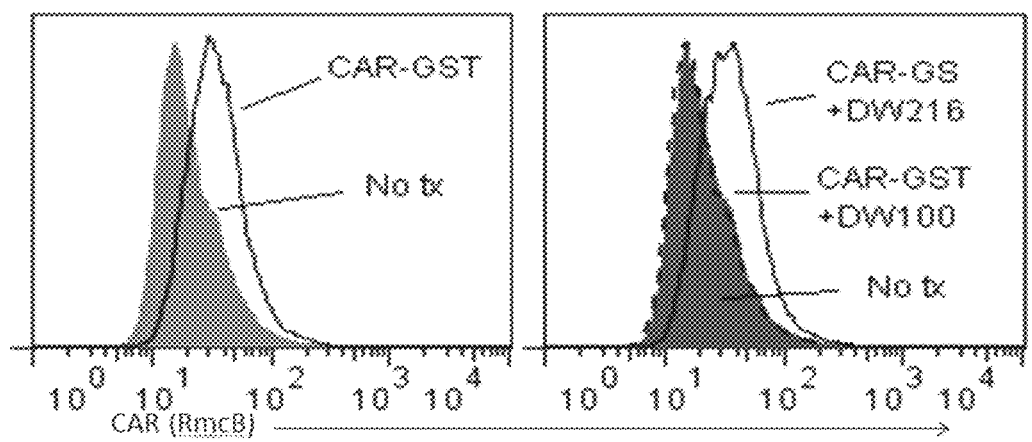
FIG. 7C. CHO-K1 cells stably expressing JAML (CHO-JAML) were incubated with CAR-GST alone (20 µg/ml, left panel) or in the presence of DW216 and DW100 mAbs (30 µg/ml, right panel) as described for sJAML and the binding was measured by flow cytometry. DW100 but not DW216 was able to prevent CAR binding to JAML on CHO cells.
Figure 7D:
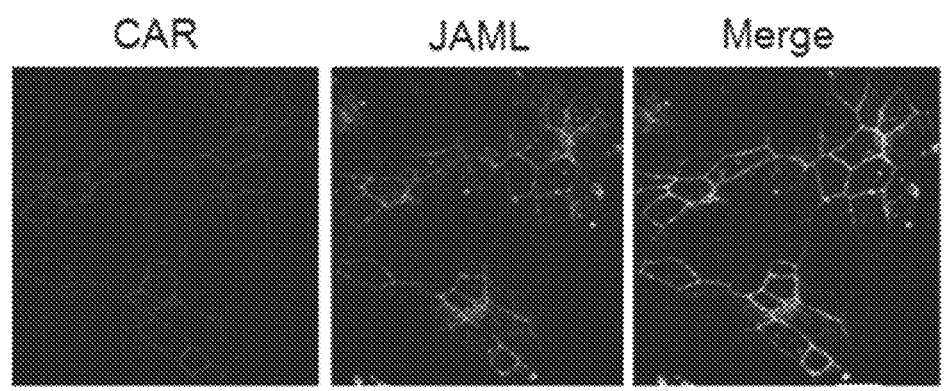
FIG. 7D. T84 monolayers were subjected to transient calcium depletion by preincubation in $Ca^{2+}$ free buffer (PBS) for 20 min to increase access to tight junctions, were incubated with sJAML (20 µg/ml) for 1 h at 37° C. The labeling pattern of JAML highly colocalizes with staining of CAR. The scale bar is 20 µm.
Figure 8A:
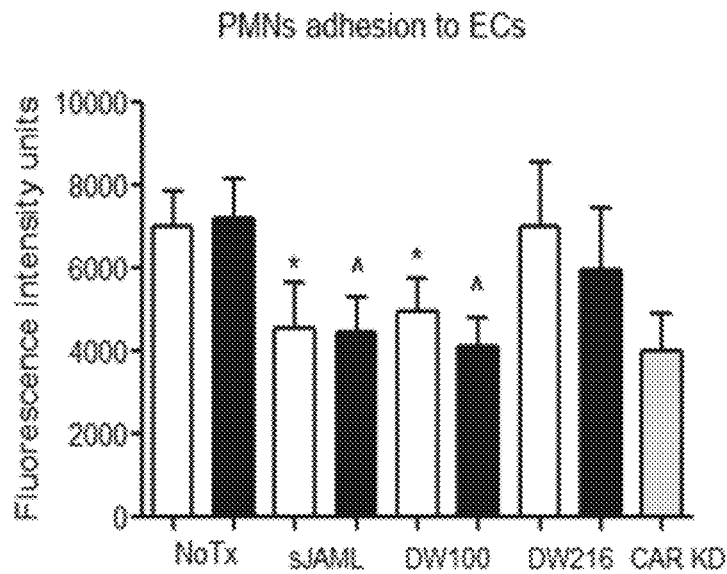
FIG. 8A shows data suggesting inhibition of JAML-CAR binding decreases adhesion of PMN and differentiated HL60 cells to epithelial cells. PMN cells were pre-labeled with CellTracker™ Green (CMFDA). Labeled cells ($2.5 \times 10^5$/well) were allowed to adhere for 1 hour to T84 (white bars) and CACO-2 (black bars) cells grown to confluency in 24 well tissue culture microtiter wells, in the absence (NoTx) or presence of soluble JAML (sJAML-His), 30 µg/ml), anti-JAML monoclonal antibodies DW100 and DW216 (30 µg/ml), or alternatively to stable CACO-2 cells lacking CAR. Non-adherent HL60 cells and PMN were removed by 3 washes with HBSS. Adherent cells were harvested by treating the monolayers with trypsin, followed by lysis with 0.1% Triton 100×. Fluorescence intensity was measured using FluoStar Galaxy plate reader at excitation/emission wavelengths of 485/535 nm. Both soluble JAML and DW100 (blocks JAML-CAR binding) but not DW216 (non-blocking mAb) decreased adhesion of HL60 cells and PMN to epithelial monolayer.
Figure 8B:
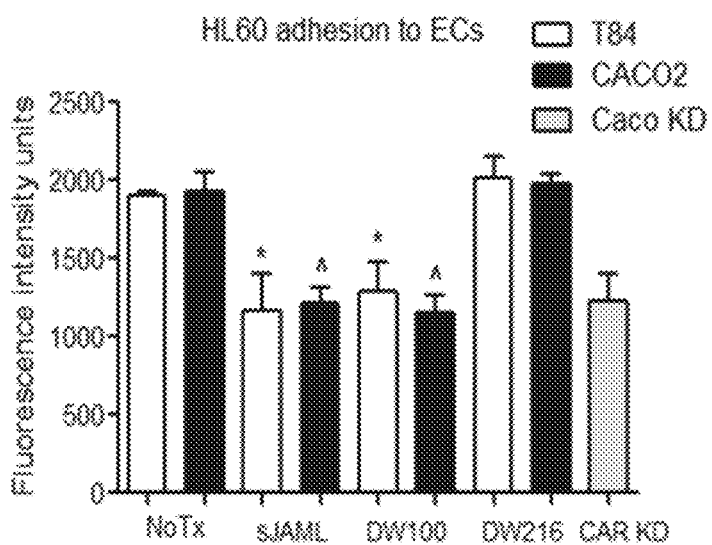
FIG. 8B shows data for HL60 cells.

As it has been established that epithelial CAR is the ligand for JAML on PMN. Whether shed JAML, as well as the recombinant protein could bind to CAR was investigated. To do this, CHO cells stably expressing CAR protein (CHO-CAR) were incubated with either supernatants from PMA activated differentiated PLB-985 (that release high levels of soluble JAML upon activation, (FIG. 2)), or recombinant soluble JAML and stained with DW216 to detect bound JAML. As shown in representative flow cytometric analysis, JAML binding to CHO-CAR was detected in both cases (FIG. 7A). As the concentration of the recombinant soluble JAML used in the assay was significantly higher than in the PLB-985 supernatants, a significantly greater shift in fluorescence was observed. The same observation was verified by IF (FIG. 7B). In FIG. 7C, in a reciprocal assay, we show that CHO cells expressing full length JAML bind soluble CAR. Moreover, confirming the specificity of our mAbs against JAML, this binding was blocked by DW100, but not DW216. Confirming previous observations, we also showed binding of soluble JAML to epithelial CAR (FIG. 7D, bottom panel) after a short calcium depletion: T84 monolayers were preincubated for 20 min in a Ca2+ free solution (PBS) before addition of soluble JAML. The calcium depletion disrupts intercellular junctions of the epithelium and allows for better penetration of soluble JAML. As seen in FIG. 8D, the chicken-wire pattern of JAML staining is typical of tight junctional staining JAML-CAR interactions are involved in PMN adhesion to epithelium. Data demonstrates that during transepitehlial migration PMN undergo activation and shedding of surface JAML that is able to bind epithelial CAR. Zen et al., 2005, Mol. Biol. Cell, Vol 16, 2694-2703, reported that PMN adhesion to purified, immobilized CAR could be decreased by the addition of an anti-human JAML antiserum, suggesting that JAML-CAR interactions could contribute to PMN adhesion to epithelium. Indeed adhesion of both HL-60 cells and PMNs to epithelium is partly dependent upon JAML-CAR binding. In the presence of soluble JAML or DW100, but not DW216, adhesion of HL-60 cells and PMNs to either T84 or Caco2 cells was significantly decreased. HL-60 cells and PMNs also adhered to a lesser degree to Caco2 cells where the expression of CAR was stably knocked down, confirming the specificity of the adhesion events to JAML-CAR interactions. Moreover, it has been demonstrated (FIG. 4C) that partial loss of surface JAML occurs upon PMN adhesion to epithelium. These results suggest that JAML that is shed by PMNs might also be involved in the regulation of PMN recruitment into the intestine lumen during inflammation.

Example 7

Soluble JAML Decreases the Recovery of Epithelial Barrier after Ca2+Switch

Figure 9A:
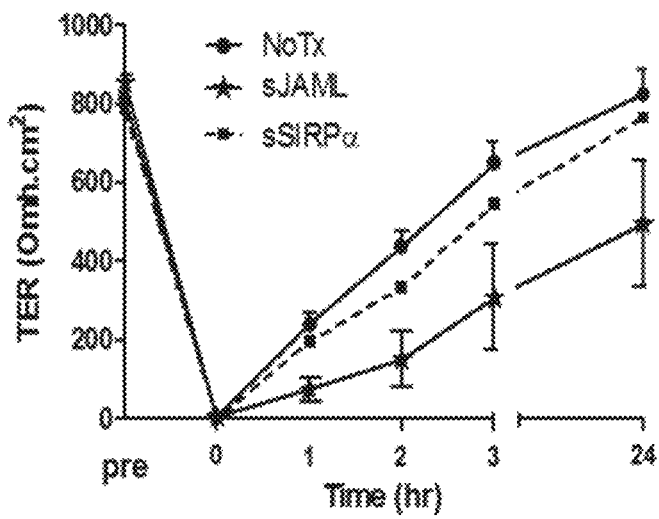
FIG. 9A shows data suggesting soluble JAML (sJAML) delays epithelial barrier recovery. T84 monolayers grown on permeable supports were subjected to transient calcium depletion by preincubation in Ca2+ free buffer (PBS) for 40 min to disassemble tight junctions, followed by switching back to calcium containing medium without (No Tx), or with sJAML or a control recombinant IgSF protein sSIRPa (30 µg/ml). Barrier recovery was measured as trans-epithelial resistance (TER) at time points as indicated.
Figure 9B:
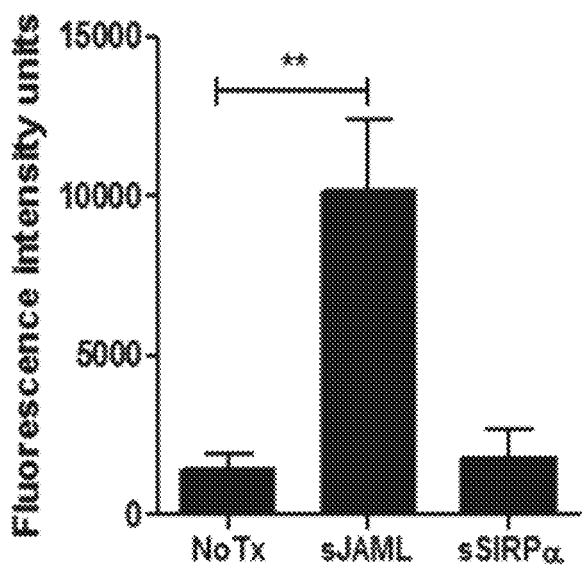
FIG. 9B. Flux of fluorescently labeled dextran (3 k) was measured at the 24 h time point for conditions as described in panel A. N=4. Soluble JAML decreased epithelial barrier recovery, suggesting that JAML shed from transmigrating PMMs may prolong the closing of the epithelial junctions by binding to CAR and assist PMN transmigration.
Figure 10A:
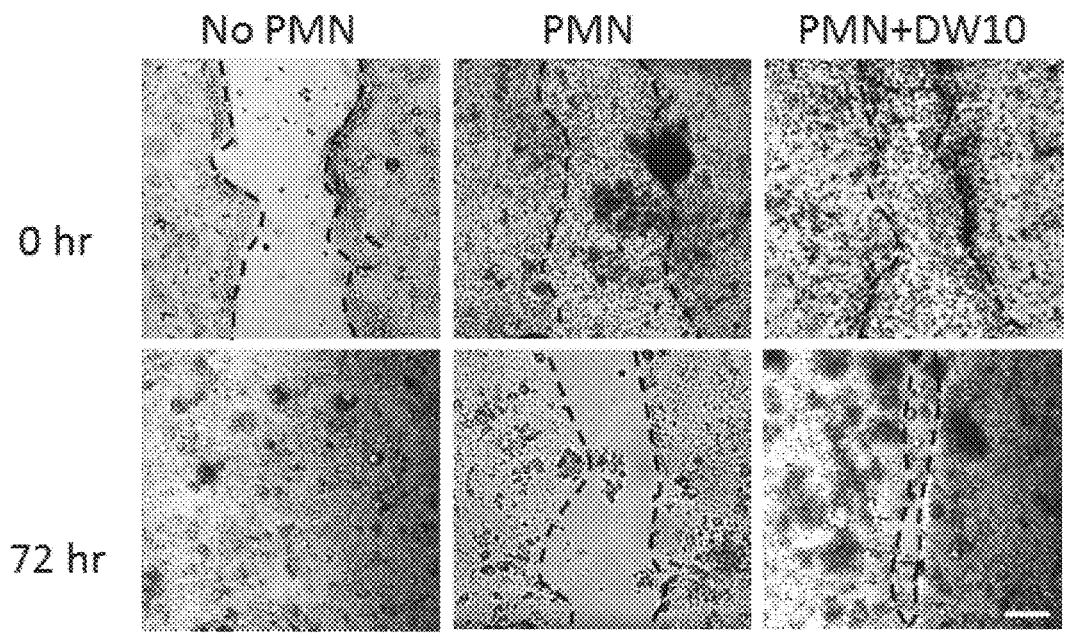
FIG. 10A shows data suggesting soluble JAML inhibits epithelial wound closure via binding to CAR and decreasing cell proliferation. T84 epithelial monolayers grown to confluence were wounded by introduction of a single linear scratch wound using a 20-µl plastic pipette tip. Wound closure was monitored over 72 h in the absence or presence of PMN or sJAML. The scale bar is 10 µm. While both PMN and sJAML inhibited wound closure, addition of DW100 but not DW216 reversed this inhibition.
Figure 10B:
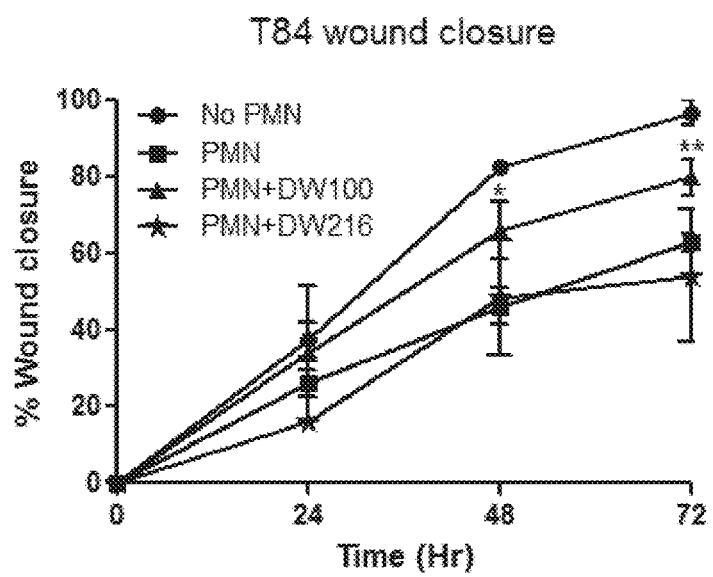
FIG. 10B shows data on T84 wound closure.
Figure 10C:
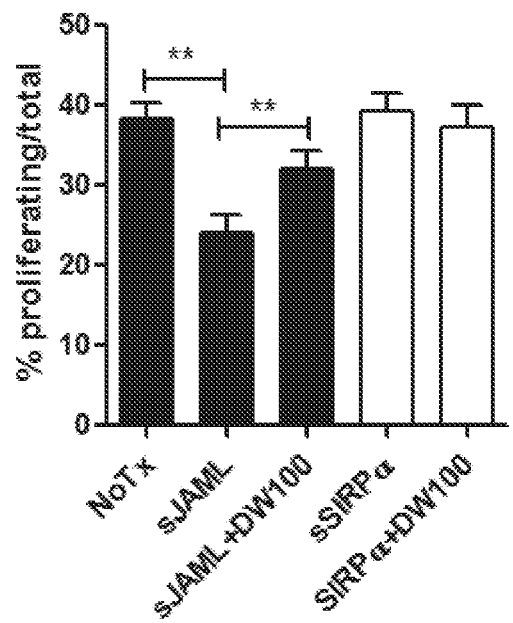
FIG. 10C Epithelial monolayers were wounded as described above and cell proliferation at the wound edge after 24 hours incubation with either sJAML or sSIRPa (30 µg/ml), with or without the addition of DW100 mAb was assessed by EdU incorporation assay. Data presented as proliferating cells (positively stained with EdU) out of all cells in the field multiplied by 100. Cells were counted in 7 randomly selected fields in 4 independent experiments.
Figure 10D:
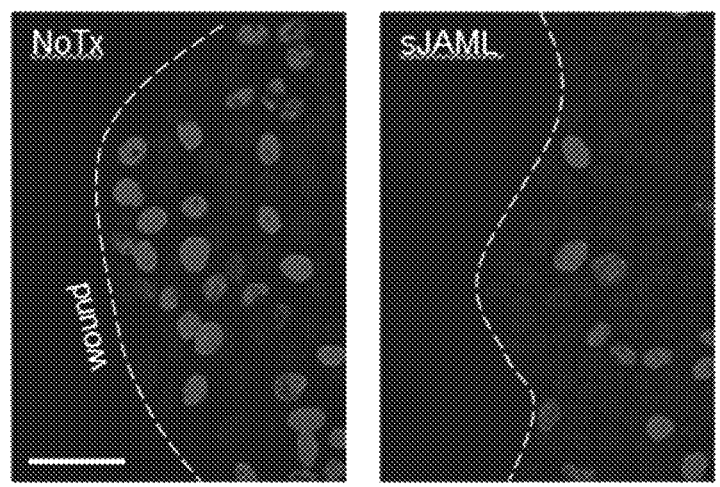
FIG. 10D. Representative images depicting the decrease in proliferating cells in the presence of JAML. The scale bar is 50 µm.

Since CAR plays a role in epithelial barrier, the effect of soluble JAML on epithelial barrier recovery was tested. Transepithelial resistance (TER) recovery experiments and dextran flux assay were performed with T84 cells grown in transwells (FIG. 9) as well as with Caco2 cells. As shown in FIG. 9, after calcium depletion and complete drop of TER, addition of soluble JAML (20 µg/ml) significantly impaired the recovery of epithelial barrier which was still evident at 24 hours (FIG. 9A), and which was confirmed by increased dextran flux (FIG. 9B). As a negative control, a related soluble IgSF molecule SIRPalpha had no effect.

Example 8

Figure 12:
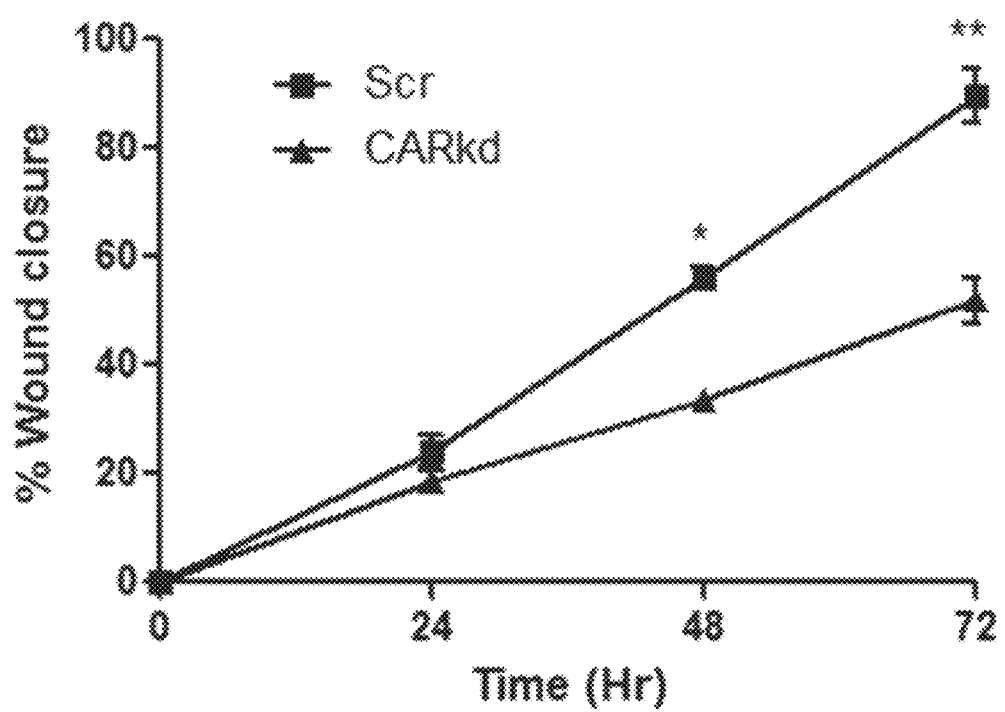
FIG. 12 shows data suggesting knockdown of epithelial CAR in Caco1 cells inhibits wound closure. Caco2 cells transfected with either scramble (Scr) or CAR encoding vectors were grown to confluence and wounded by introduction of a single linear scratch wound using a 20-µl plastic pipette tip. Wound closure was monitored over 72 h time period. Knockdown of CAR results in inhibition of wound closure. (N=three separate experiments).

JAML Released from Activated PMNs Delays Epithelial Wound Closure by Interacting with Epithelial CAR The expression of CAR is up-regulated at the edges of closing wounds. Knock down of CAR in Caco2 cells was observed to resulted in impaired wound restitution (FIG. 12). Whether JAML binding to CAR would affect epithelial wound restitution was investigated. Incubation of wounded epithelial monolayers with PMNs resulted in significantly delayed wound restitution (FIG. 10 A,B). If soluble JAML interactions with CAR play a role, the effect could be reversed with the addition of blocking DW100 mAb. Indeed, incubation of wounded T84 monolayer with PMN in the presence of DW100 mAb (30 µg/ml), but not DW216 mAb (30 µg/ml) significantly improved wound restitution (FIG. 10 A,B) approaching values observed with no PMN addition at all. Similar results were observed with Caco2 cells.

JAML binding CAR to inhibit epithelial cell proliferation was investigated as a possible mechanism for impeding wound healing. Indeed, as shown in FIG. 10, panels C and D, soluble JAML significantly inhibits proliferation of T84 intestinal epithelial cells and this is blocked by addition of DW100.

These effects are also probably relevant to monocytes. Monocytes also shed JAML and are the second responders to tissue injury during the inflammatory responses. Monocytes have JAML on their surface. See FIG. 11. CAR affects wound closure suggesting that JAML binding to CAR may and mimic loss of CAR in a regional manner, e.g., at sites of inflammation. JAML ligation of CAR neutralizes the pro-barrier and pro wound-healing effects of CAR and our antibodies ablate this negative effect of JAML. Thus, DW100 and DW55 may specifically and locally target inflammation. CAR is important in the heart muscle and since acute myocardial infarction is associated with massive recruitment of PMNs followed by monocytes to the injured heart, DW100 and DW55 could reduce some of the damage associated with myocardial infarction by improved healing.

Example 9

JAML Binding Humanized Ig Chimera

The light and heavy chains of DW100, DW55, and DW216 were sequenced and provided below.

```
H1 or DW100
                                    (SEQ ID NO: 19)
DVQLVESGAELVRPGASVKLSCKALAYTFTDYEMHWVKQTPVHGLEWIGI

IHPGSGGTVYNQKFKGKATLTADKSSSTAYMELSSLTSEDSTVYYCTRRR

YYGSSYWYFDVWGAGN;

H2 or DW55
                                    (SEQ ID NO: 20)
CDVQLVESGGGLVQPGGSRKLSCAASGFTFSDYGMAWVRQAPGKGPEWVA

FISNLAYSIYYSDTVTGRFTISRENAKNTLYLEMSSLRSEDTAMYYCARG

DYSGGMMDYWGQGT;
and

H3 or DW 216
                                    (SEQ ID NO: 21)
DVQLVESGPGLVKPSQSLSLTCTVTGYSITSDYAWNWIRQFPGNKLEWMG

YISSSGNSNYNPSLKSRISITRDTSKNQFFLQLNSVTTEDTATYYCAGAT

GYSMDYWGQGTTLTVK.

L1 or DW100
                                    (SEQ ID NO: 22)
VLTQSPASLAASVGETVTITCRASENIYYSLAWYQQKQGKSPQLL*IYNA

NSLEDGVPSRFSGSGSGTQYSLKINSMQPEDTATYFCEQTYDVPLTFGAG

TKLEL;
wherein L* is optionally substituted with M.

L2 or DW55
                                    (SEQ ID NO: 23)
VLTSQPASLAVSLGQRATISYRASKSVSTSGYSYMHWNQQKPGQPPRLLI

YLVSNLESGVPARFSGSGSGTDFTLNIHPVEEEDAATYYCQHIRELTRSE

GGPSWK;
and

L3 or DW216
                                    (SEQ ID NO: 24)
VLTQSPAIMSASLGERVTMTCTASSSVSSSYLHWYQQKPGSSPKLWIYST

SNLASGVPARFSGSGSGTSYSLTISSMEAEDAATYYCHQYHRSPFTFGSG

TKLELK.
```

One derives JAML binding peptides from these sequences, typically the consensus sequences, to express them in E. coli as fusions to human IgG1 Fc. The amino acid sequence of a human IgG1 Fc portion of certain embodied peptide-Fc fusion proteins are as follows:

(SEQ ID NO: 78)
DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQG

NVFSCSVMHEALHNHYTQKSLSLSPGK

The full amino acid sequences of the peptide-Fc fusion proteins are as follows

M-Fc-DW100 variable light chain
(SEQ ID NO: 79)
M DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSPGK VLTQSPASLAASVGETVTIT

CRASENIYYSLAWYQQKQGKSPQLLIYNANSLEDGVPSRFSGSGSGTQYS

LKINSMQPEDTATYFCEQTYDVPLTFGAGTKLEL

M-DW100 variable light chain-Fc
(SEQ ID NO: 80)
M VLTQSPASLAASVGETVTITCRASENIYYSLAWYQQKQGKSPQLLIYN

ANSLEDGVPSRFSGSGSGTQYSLKINSMQPEDTATYFCEQTYDVPLTFGA

GTKLEL DKTHTCPPCPAPELLGGPSVFLFPPKPKDTLMISRTPEVTCVV

VDVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQV

SLTCLVKGFYPSDIAVEWESNGQPENNYKTTPPVLDSDGSFFLYSKLTVD

KSRWQQGNVFSCSVMHEALHNHYTQKSLS

M-Fc-DW100 variable heavy chain
(SEQ ID NO: 81)
M DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSPGK DVQLVESGAELVRPGASVKL

SCKALAYTFTDYEMHWVKQTPVHGLEWIGIIHPGSGGTVYNQKFKGKATL

TADKSSSTAYMELSSLTSEDSTVYYCTRRRYYGSSYWYFDVWGAGN

M-DW100 variable heavy chain-Fc
(SEQ ID NO: 82)
M DVQLVESGAELVRPGASVKLSCKALAYTFTDYEMHWVKQTPVHGLEWI

GIIHPGSGGTVYNQKFKGKATLTADKSSSTAYMELSSLTSEDSTVYYCTR

RRYYGSSYWYFDVWGAGN DKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

-continued
PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGK

Also, the amino acid sequence of a human IgG-Light chain constant region is:

(SEQ ID NO: 84)
RADAAPTVSIFPPSSEQLTSGGASVVCFLNNFYPRDINVKWKIDGSERQN

GVLNSWTDQDSKDSTYSMSSTLTLTKDEYERHNSYTCEATHKTSTSPIVK

SFNRNEC

The full amino acid sequences of the peptide-Light chain constant region fusion protein is as follows:
M-DW 100 variable light chain (VL)-Light chain constant region:

(SEQ ID NO: 85)
M VLTQSPASLAASVGETVTITCRASENIYYSLAWYQQKQGKSPQLL*IY

NANSLEDG VPSRFSGSGSGTQYSLKINSMQPEDTATYFCE QTYDVPLT

FGAGTKLELRAD AAPTVSIFPPSSEQLTSGGASVVCFLNNFYPRDINVK

WKIDGSERQNGVLNSWTDQDSKDSTYSMSSTLTLTKDEYERHNSYTCEAT

HKTSTSPIVKSFNRNEC

One may lyse E. coli cells expressing peptide-Fc fusion proteins using high-pressure homogenization, and inclusion bodies. After subsequent protein folding, selective precipitation, and filtration, one may employ chromatographic purification steps (e.g., ion exchange chromatography, Protein A, or hydroxyapatite chromatography).

Example 10

Fully Human Monoclonal Antibodies (mAbs) to Human JAML

One generates fully human mAbs from nonhuman variable regions using information from the human germline repertoire. Residues within and proximal to CDRs and the $V_H/V_L$ interface (e.g., SEQ ID NOs 1-24) are iteratively explored for substitutions to the closest human germline sequences using semi-automated computational methods. See Bernett et al., J. Mol. Biology, 2010, 396(5):1474-1490, hereby incorporated by reference in its entirety. One generates fully human antibodies with substitutions compared to the parent murine sequences. Substitutions may be in the CDRs.

The engineering process to generate fully human mAbs from murine Fvs consists of five main steps: (1) design of framework-optimized VH and VL template sequences, (SEQ ID NOs: 19-24) (2) identification of the closest matching human germline sequence for the framework-optimized VH and VL, (3) screening of all possible single substitutions that increase the sequence identity of the framework-optimized sequence to the closest human germline sequence, (4) screening of VH and VL variants consisting of combinations of neutral or affinity enhancing single substitutions, and (5) screening of the highest-affinity VH and VL pairs to generate the final fully human mAb.

One defines two principal scores used to measure sequence humanness. Human identity is defined as the number of exact sequence matches between the Fv and the highest identity human germline VH, Vκ, JH, and Jκ chains (the D-segment for the heavy chain is not included). The second score is the number of total "human 9-mers", which is an exact count of 9-mer stretches in the Fv that perfectly match any one of the corresponding stretches of nine amino acids in our set of functional human germline sequences. Both human 9-mers and human identity are expressed as percentages throughout in order to enable comparison between antibody Fvs of different lengths.

Example 11

Ligation of CAR at the JAML Binding Site Delays Colonic Mucosal Wound Healing In-Vivo In-vitro data indicates that CAR is involved in the regulation of epithelial wound healing, and that JAML binding to CAR inhibits CAR mediated regulation of wound healing. To examine this in-vivo, the effect of inhibition of CAR function on mucosal wound recovery was analyzed. The adenoviral fiber knob protein Ad5 but not Ad11 has been reported to bind murine CAR and compete with JAML binding. See Witherden et al., Science, 2010, 329(5996): 1205-1210. Whether administration of recombinant Ad5 inhibits colonic wound healing was examined in mice in a fashion analogous to the endogenous CAR ligand, JAML. Colonic mucosal wounds were generated using a mouse colonoscope (FIG. 13, Panel A), and wound recovery was examined 2 and 4 days post wounding by endoscopic imaging in the presence of Ad5, Ad11 (administered I.P, twice a day1 Ogg in 200 µl PBS) or PBS alone. Ad5 but not Ad11 or PBS treatment resulted in significantly delayed mucosal wound healing 4 days after wounding (−20% vs. 76 and 83% respectively, FIG. 13, Panel B). The delayed wound closure was also evident from histological analysis (representative images, FIG. 13, Panel C) and whole mount preparation (representative images, FIG. 13, Panel D). Furthermore, using immunofluorescence labeling of wounded mouse colonic tissue (1 day after wounding) we confirmed that I.P. administered his-tagged Ad5 but not his tagged Ad11 colocalizes with epithelial CAR at wounded areas (colocalization of CAR and His tag in yellow, representative images, FIG. 13, Panel E).

Materials and Methods
Cells

HL60 and PLB-985, promyelocytic leukemia cells lines, CHO-K1 (CHO) wild type Chinese hamster ovary cell line, HEK293T human embryonic kidney cell line with T antigen are available from ATCC and were propagated according to provided protocols. HL60 and PLB-985 were passaged in RPMI supplemented with 20% heat inactivated FBS (Atlanta Biologicals) with supplements in 5% CO2 at 37° C. These cells can be differentiated into banded and segmented neutrophils by stimulation with DMSO for 5 to 7 days. (Pubmed 276884). To set up differentiated cultures, cells are plated at $0.25 \times 10^6$/ml in T162 flasks with addition of 1.25% DMSO. Differentiated cells are harvested at d.6. Both CHO and HEK293T cells were passaged in DMEM high Glucose with 10% FBS and supplements. Human T84 and Caco-2 epithelial cell lines were grown in high glucose DMEM (Dulbecco's modified Eagle's medium), supplemented with 10% FBS, 100 units/ml penicillin, 100 µg/ml streptomycin, 15 mM Hepes (pH 7.4), 2 mM L-glutamine, and 1% non-essential amino acids. T84 human epithelial cells (passage 68-72) (Parkos et al., J. Clin. Invest., 1991, 88:1605-1612) and Caco-2 cells (passage 28-38) were grown as previously described. HDMEC, human dermal microvascular endothelial cells (passage 4-9) were a kind gift from Nancy Louis and grown according to manufacturer's instructions.

Blood was drawn and handled according to protocols for the protection of human subjects, as approved by the Emory University Hospital Institutional Review Board, and all volunteer subjects gave informed consent in accordance with the Declaration of Helsinki (2000). PMNs were isolated by density gradient centrifugation as previously described (Mackarel, A. J. J. Immunol. 167:2839-2846) and resuspended in HBSS with 10 mM HEPES pH 7.4 without Ca and Mg at a concentration of $5 \times 10^7$ cells/ml. PMNs were used in experiments within 2 hours of isolation.

Generation of Recombinant Proteins

Plasmid constructs were generated at the Custom Cloning Center Facility of Emory University by Dr. Oskar Laur and fully sequenced. JAML gene (Accession # AJ515553) was cloned in pcDNA3.0 vector (Invitrogen Life Technologies) and tagged at the C-terminal with either 10 Histidine residues or with 6×Myc tag sequence or with rabbit Fc. Truncated constructs were generated by PCR, soluble JAMLD1D2 was truncated and tagged after residue Leucine-259, soluble JAML-D1 was truncated at residue Proline 140. Constructs for soluble proteins were transfected in HEK293 T cells using the reagent polyethylenimine (PEI) as in Boussif et al., Proc. Natl. Acad. Sci. U.S.A., 1995, 92, 7297-7301.

Supernatants of transfected cultures in T162 flasks were first assessed for the presence of soluble recombinant protein by dot blot using polyclonal rabbit anti His followed by HRP-conjugated goat anti rabbit secondary antibody and blots were developed with a chemiluminescence kit (Roche). Supernatants were collected once every fourth day until cessation of production as determined by dot blots. Soluble His-tagged proteins were purified on Ni-NTA agarose beads columns (Qiagen) and eluted with 250 mM imidazole (Fluka). Purified proteins were first dialyzed against PBS and concentrated using Centricon microconcentrators (Fisher). Purity of proteins was assessed by SDS-PAGE followed by Western blotting for the His tag as described above and concentrations measured by optical density at 280 nm wavelength (Nanodrop, Thermofisher). The same transfection reagent was used to generate stable JAML transfectants of CHO-K1 cells expressing full length genes tagged at the C-term with either 10 His or 6×Myc. Stable transfectants were selected by addition of 500 µg/ml G418 to the medium and cloned by limiting dilution. High expressing clones were identified by flow cytometry using serum from the immunized mice followed by goat anti mouse-Alexa-488. CAR-GST construct is described in Zen et al., Mol. Biol. of the Cell vol 16, 2694-2703, 2005. The full length gene of CAR was cloned into pcDNA3.1-Hygromycin (Invitrogen, Carlsbad, Calif.) and transfected into CHO-K1 cells. CHO-CAR transfectants were grown in DMEM, 10% FBS containing 500 µg/mlHygromycin B (Sigma). Single cell clones were generated by limiting dilution and grown in medium supplemented with Hygromycin B. Surface expression of CAR was assessed by flow cytometry. High expressing clones were identified by staining with mAb RmcB followed by goat anti mouse-Alexa488 using FACS Calibur (BD Biosciences) and FlowJo software (Treestar).

Antibodies and Reagents

RmcB monoclonal antibody (mAb) to human CAR and 9E10 mAb anti myc are available at ATCC, CBRM1/29 mAb anti CD11b/CD18 is described in Balsam et al., JI, 1998, 160:5058-5065. Goat anti Mouse-Alexa 488 was obtained from Invitrogen (Carlsbad, Calif.). HRP-conjugated goat anti mouse IgG, goat anti rabbit Ig γ specific were obtained from Jackson Immunoresearch (West Grove, Pa.). HRP-conjugated anti GST was obtained from GE Healthcare and rabbit anti His from Abcam, Cambridge, Mass. HRP-conjugated Streptavidin was purchased from Zymed, San Francisco, Calif. Antibodies were biotinylated using Ezlink Sulfo-NHS-LC-Biotin (Thermo Scientific, Rockford, Ill.) according to manufacturer's directions. Antibodies were conjugated to CNBr-Sepharose 4 Fast Flow beads (GE Healthcare) according to manufacturer's instructions.

Briefly, beads were washed with 100 mM HCl and equilibrated in coupling buffer (0.1M Na Carbonate buffer/ 0.5 M NaCl) at pH9.0. Beads were pelleted for 3 min. at 500 RPM. Antibody solution was brought to pH 9.0 by addition of 1M Na Carbonate buffer pH 9 ($\frac{1}{10}$ of antibody volume) and added to the beads. The suspension was placed on a rotator at 4° C. for 3 hours or overnight. Beads were pelleted, antibody bound was estimated by comparing optical densities at 280 nm of samples pre and post conjugation. Unbound protein was washed with 3 cycles of alternating buffers: 100 mM Na-Acetate buffer pH 4.0, 500 mM NaCl followed by 100 mM Tris-HCl buffer at pH 8.0, 500 mM NaCl. Beads were finally equilibrated in PBS as a 50/50 (vol/vol) suspension. ABTS, (2,2'-azinobis-(3-ethylbenzo-thiazoline-6-sulfonic acid), 2,10-Phenanthroline monohydrate, N-Ethylmaleimide, Phenylmethylsulfonyl fluoride (PMSF), protease inhibitor cocktail (cat #P8340), PMSF and Phorbol Myristate Acetate (PMA) are available at Sigma, St Louis, Mo. as well as chemotactic peptide fMLF. TAPI-2 was purchased from Calbiochem, Merk, Darmstadt, Germany.

Cell Biotinylation and Immunoprecipitation

HL60, PLB-985 or PMN were washed in cold Hanks medium without Ca or Mg (Sigma) and biotinylated as follows: briefly, after washing cells were resuspended and incubated with 8 mg Biotin reagent dissolved in 1 ml PBS. Final concentration of cells is $50 \times 10^6$/ml. The reaction is allowed to proceed for 30 min at 4° C. Cells were spun 8 min. at 1,200 RPM at 4° C. and resuspended in 20 ml 40 mM Tris-HCl pH 8.0, 100 mM NaCl for another 30 min to quench the unreacted moieties. Cells were washed once and resuspended at $50 \times 10^6$ cells/ml. Lysates of biotinylated cells were prepared in RIPA buffer containing protease inhibitors (Sigma), incubated for 1 hour on ice, with frequent vortexing. Lysates were sonicated briefly and spun at 10,000 RPM for 10 min. at 4° C. For preclearing, Sepharose 4B was equilibrated in PBS and 400 µl sepharose bead suspensions (50/50) were aliquoted in Eppindorf tubes. Supernatants were aspirated off and lysates were added to pelleted beads. Tubes were rotated overnight at 4° C. Beads were spun and cleared lysates were transferred to new tubes containing 100 µl pelleted antibody-conjugated beads. Again the suspension was rotated at 4° C. for 1½ hour. Beads were washed 5 times in RIPA buffer containing protease inhibitors followed by 2 washes in 1% Octyl-β-D-glucopyranoside (Sigma) in 100 mM Tris-HCl buffer pH 7.4. Beads were boiled 5 min. in non-reducing conditions. Samples were subjected to SDS-PAGE using BioRad criterion 4-15% gels and proteins were transferred to a nitrocellulose membrane (BioRad). Blots were revealed using Streptavidin-HRP conjugate and chemiluminescence.

To immunoprecipitate soluble JAML released from cells, biotinylated cells were resuspended in small volume of Hanks solution with Ca and Mg. Phorbol Myristate Acetate (PMA) was added to appropriate tubes to a final concentration of 200 nM. Cells were incubated at 37° C. for 30 min. then spun at 1,200 RPM and supernatants were collected and added first to Sepharose beads O.N. followed by antibody-conjugated beads as described above.

Detection of Soluble JAML by Capture ELISA Cells were suspended at $100 \times 10^6$ cells/ml in 50 ml centrifuge tubes. PMA was added at a final concentration of 200 nM and tubes incubated at 37° C. of 30 min. Supernatants were collected by centrifugation. To eliminate the presence of macroparticles in the supernatants, ultracentrifugation was performed in a table-top microcentrifuge (Beckman TL-100) at 100,000 g for 30 minutes. The "cleared" supernatants were assayed for the presence of soluble JAML.

Purified antibody DW100 (100 µl/well of 10 µg/ml dilution) was coated onto a high binding 96 well plate (Immulon II) overnight at 4° C. or 1½ hr at 37° C. After washing, 200 µl of 5% blocking solution (Roche) was added to each well for 1 hr at room temperature (RT). After washing, 100 µl supernatant samples in triplicates were added to the wells as well as serial dilutions of purified sJAML-His and incubated for 1 hr RT. After washing, 100 µl biotinylated DW216 antibodies was added at 10 µg/ml. This was followed after a wash by Streptavidin-HRP diluted at 1:4000. The wells were washed again and after addition of ABTS substrate, wells were analyzed using a microplate reader at 405 nm wavelength.

Flow Cytometry

Cells suspensions of adherent cells were prepared by trypsinization with Trypsin-EDTA (Sigma). After washing, cells were resuspended in FACS buffer (2% FBS in PBS+ 0.1% Na Azide). Approximately, $3-5 \times 10^5$ cells were incubated with 5-10 µg/ml of primary antibody for 1 hr at 4° C. followed by 3 washes in FACS buffer and incubation with 1 µg/ml secondary antibody conjugated with Alexa-488. After final washes, cells were analyzed using FACS Calibur. To measure JAML shedding from cells or inhibition of shedding, cell suspensions were first incubated with PMA (200 nM) in the presence or absence of specific inhibitors for 30 min at 37° C. (final concentrations: AEBSF 2 mM, Sigma protease inhibitors used at 1/50 dilution, PMSF: 1 mM, 2-10 Phenanthroline: 5 mM, NEM: 6 mM and TAPI-2: 1 µM.) Cells were washed, resuspended in FACS buffer and stained as described above. To measure JAML expression on PMNs after adhesion to epithelial cells, PMNs ($2.5 \times 10^5$ cell/well) were first allowed to adhere to a confluent layer of T84 cells for 15 minutes. All adhered cells were harvested by treating the monolayers with trypsin and prepared for flow cytometry as described above. All samples were stained for JAML (DW100 mAb) and CD11b/CD18 (CBRM 1/29), and only CD11b/CD18 positive cells (PMNs) were analyzed for JAML expression.

Cell Adhesion Assay

Epithelial cells (T84/Caco-2) were seeded on 24-well plates ($10^6$ cells/well) and cultured until they reached confluence. PMNs or HL60 cells were loaded with Cell-Tracker™ Green (CMFDA, 10 min at 370 C) and were allowed to adhere ($2.5 \times 10^5$ cell/well) for 1 hour in HBSS(−) buffer at 37° C. After three washes adherent cells were harvested by treating the monolayers with trypsin, and lysed with 1% Triton 100×. Fluorescence intensity was measured using FluoStar Galaxy plate reader at excitation/emission wavelengths of 485/535 nm. The background autofluorescence of the epithelial cells was subtracted from all samples.

Immunofluorescence Microscopy

For PMN staining, cells were stained in suspension using appropriate primary Ab (10 µg/ml) followed by fluorescently labeled secondary Abs, 1 hr each condition at 40 C. After washing cells were fixed in 3.7% PFA and mounted on 13-mm collagen coated coverslips. For epithelial cells, cells grown on 13-mm collagen coated coverslips fixed permeabilized with 95% ethanol at −200 C for 15 minutes, blocked with 3% BSA (wt/vol) for 1 hr and incubated with appropriate primary Ab (10 µg/ml) followed by fluorescently labeled secondary Abs, 1 hr each condition at 40 C. Nuclei were stained with ToPro-1 iodide (Invitrogen) and coverslips were mounted on slides in Prolong Gold (Invitrogen). All images were taken on LSM 510 confocal microscope (Carl Zeiss, Thornwood, N.Y.) with Plan-Neofluor 60× and 40× objectives.

Assessment of Cell Proliferation and Apoptosis

Cell proliferation was assessed in 5-ethyl-2'-deoxyuridine (EdU) incorporation assay, by using a Click-iT EdU Alexa 488 cell proliferation kit (Invitrogen). Cell apoptosis was assessed by staining with sulforhodamine labeled caspase inhibitor SR-VAD-FMK from APO LOGIX Sulforhodamine Caspase Detection kit (Cell Technology). Scratch wounded or confluent cells were subjected to treatment as indicated in the figure were incubated for 24 hrs at 370 C before addition of EdU or APO LOGIX Sulforhodamine Caspase Detection kits. At least 5 random fields per each condition were analyzed, the data are presented as % proliferating/apoptotic cells out of total cells in the field.

Wounding of Epithelial Monolayers

Cell grown in 24-well tissue culture plates received one linear wound using a 20-µl plastic pipette tip attached to low suction. Wounded monolayers were washed once with PBS to remove detached cells and debris, and incubated with the appropriate stimulus added to the medium. The rate of migration was measured by determining the wound area immediately after wounding (t=0) and at the indicated time points. The data are presented as the area of the wound at each time point normalized to t=0. The experiments were carried out in triplicates per condition, and the data shown are representative of 4 independent experiments.

All references cited herein are incorporated by reference in their entirety.

The invention claimed is:

1. A chimeric JAML antibody that substantially prevents human JAML from binding CAR having CDR1, CDR2, and CDR3 heavy chain respective sequences of:
   (SEQ ID NO:1) DYEMH;
   amino acid residues 46 to 68 of SEQ ID NO: 19; and
   (SEQ ID NO: 3) TRRRYYGSSYNWYFDV;
   and having CDR1, CDR2, and CDR3 light chain respective sequences of:
   (SEQ ID NO. 10) CRASENIYYSLAW;
   (SEQ ID NO. 11) NANSLEDGVPSR; and
   (SEQ ID NO. 12) YFCEQTYDVPLTFGAGT,
   wherein the antibody does not substantially bind to JAMA or JAMC.

2. The chimeric antibody of claim 1, wherein the antibody binds the D1 domain of JAML.

3. The chimeric antibody of claim 1, wherein the antibody is a monoclonal antibody.

4. A pharmaceutical composition comprising an antibody of claim 1.

* * * * *

```
                         SEQUENCE LISTING

<160> NUMBER OF SEQ ID NOS: 82

<210> SEQ ID NO 1
<211> LENGTH: 5
<212> TYPE: PRT
<213> ORGANISM: Artificial
<220> FEATURE:
<223> OTHER INFORMATION: Synthetic

<400> SEQUENCE: 1

Asp Tyr Glu Met His
1               5

<210> SEQ ID NO 2
<211> LENGTH: 22
<212> TYPE: PRT
<213> ORGANISM: Artificial
<220> FEATURE:
<223> OTHER INFORMATION: Synthetic

<400> SEQUENCE: 2

Trp Ile Gly Ile Ile His Pro Ser Gly Gly Thr Val Tyr Asn His
1               5                   10                  15

Lys Phe Lys Gly Lys Ala
            20

<210> SEQ ID NO 3
<211> LENGTH: 16
<212> TYPE: PRT
<213> ORGANISM: Artificial
<220> FEATURE:
<223> OTHER INFORMATION: Synthetic

<400> SEQUENCE: 3

Thr Arg Arg Arg Tyr Tyr Gly Ser Ser Tyr Asn Trp Tyr Phe Asp Val
1               5                   10                  15

<210> SEQ ID NO 4
<211> LENGTH: 5
<212> TYPE: PRT
<213> ORGANISM: Artificial
<220> FEATURE:
<223> OTHER INFORMATION: Synthetic

<400> SEQUENCE: 4
```

Asp Tyr Gly Met Ala
1               5

<210> SEQ ID NO 5
<211> LENGTH: 16
<212> TYPE: PRT
<213> ORGANISM: Artificial
<220> FEATURE:
<223> OTHER INFORMATION: Synthetic

<400> SEQUENCE: 5

Phe Ile Ser Asn Leu Ala Tyr Ser Ile Tyr Tyr Ser Asp Thr Val Thr
1               5                   10                  15

<210> SEQ ID NO 6
<211> LENGTH: 12
<212> TYPE: PRT
<213> ORGANISM: Artificial
<220> FEATURE:
<223> OTHER INFORMATION: Synthetic

<400> SEQUENCE: 6

Ala Arg Gly Asp Tyr Ser Gly Gly Met Met Asp Tyr
1               5                   10

<210> SEQ ID NO 7
<211> LENGTH: 5
<212> TYPE: PRT
<213> ORGANISM: Artificial
<220> FEATURE:
<223> OTHER INFORMATION: Synthetic

<400> SEQUENCE: 7

Asp Tyr Ala Trp Asn
1               5

<210> SEQ ID NO 8
<211> LENGTH: 14
<212> TYPE: PRT
<213> ORGANISM: Artificial
<220> FEATURE:
<223> OTHER INFORMATION: Synthetic

<400> SEQUENCE: 8

Ser Ser Ser Gly Asn Ser Asn Tyr Asn Pro Ser Leu Lys Ser
1               5                   10

<210> SEQ ID NO 9
<211> LENGTH: 10
<212> TYPE: PRT
<213> ORGANISM: Artificial
<220> FEATURE:
<223> OTHER INFORMATION: Synthetic

<400> SEQUENCE: 9

Ala Gly Ala Thr Gly Tyr Ser Met Asp Tyr
1               5                   10

<210> SEQ ID NO 10
<211> LENGTH: 13
<212> TYPE: PRT
<213> ORGANISM: Artificial
<220> FEATURE:
<223> OTHER INFORMATION: Synthetic

<400> SEQUENCE: 10

Cys Arg Ala Ser Glu Asn Ile Tyr Tyr Ser Leu Ala Trp

```
1               5                   10
```

<210> SEQ ID NO 11
<211> LENGTH: 12
<212> TYPE: PRT
<213> ORGANISM: Artificial
<220> FEATURE:
<223> OTHER INFORMATION: Synthetic

<400> SEQUENCE: 11

```
Asn Ala Asn Ser Leu Glu Asp Gly Val Pro Ser Arg
1               5                   10
```

<210> SEQ ID NO 12
<211> LENGTH: 17
<212> TYPE: PRT
<213> ORGANISM: Artificial
<220> FEATURE:
<223> OTHER INFORMATION: Synthetic

<400> SEQUENCE: 12

```
Tyr Phe Cys Glu Gln Thr Tyr Asp Val Pro Leu Thr Phe Gly Ala Gly
1               5                   10                  15
Thr
```

<210> SEQ ID NO 13
<211> LENGTH: 14
<212> TYPE: PRT
<213> ORGANISM: Artificial
<220> FEATURE:
<223> OTHER INFORMATION: Synthetic

<400> SEQUENCE: 13

```
Ser Tyr Arg Ala Ser Lys Ser Val Ser Thr Ser Gly Tyr Ser
1               5                   10
```

<210> SEQ ID NO 14
<211> LENGTH: 13
<212> TYPE: PRT
<213> ORGANISM: Artificial
<220> FEATURE:
<223> OTHER INFORMATION: Synthetic

<400> SEQUENCE: 14

```
Leu Val Ser Asn Leu Glu Ser Gly Val Pro Ala Arg Phe
1               5                   10
```

<210> SEQ ID NO 15
<211> LENGTH: 14
<212> TYPE: PRT
<213> ORGANISM: Artificial
<220> FEATURE:
<223> OTHER INFORMATION: Synthetic

<400> SEQUENCE: 15

```
Gln His Ile Arg Glu Leu Thr Arg Ser Glu Gly Gly Pro Ser
1               5                   10
```

<210> SEQ ID NO 16
<211> LENGTH: 11
<212> TYPE: PRT
<213> ORGANISM: Artificial
<220> FEATURE:
<223> OTHER INFORMATION: Synthetic

<400> SEQUENCE: 16

```
Thr Ala Ser Ser Ser Val Ser Ser Tyr Leu
1               5                   10
```

<210> SEQ ID NO 17
<211> LENGTH: 13
<212> TYPE: PRT
<213> ORGANISM: Artificial
<220> FEATURE:
<223> OTHER INFORMATION: Synthetic

<400> SEQUENCE: 17

```
Ser Thr Ser Asn Leu Ala Ser Gly Val Pro Ala Arg Phe
1               5                   10
```

<210> SEQ ID NO 18
<211> LENGTH: 12
<212> TYPE: PRT
<213> ORGANISM: Artificial
<220> FEATURE:
<223> OTHER INFORMATION: Synthetic

<400> SEQUENCE: 18

```
His Gln Tyr His Arg Ser Pro Phe Thr Phe Gly Ser
1               5                   10
```

<210> SEQ ID NO 19
<211> LENGTH: 116
<212> TYPE: PRT
<213> ORGANISM: Artificial
<220> FEATURE:
<223> OTHER INFORMATION: Synthetic

<400> SEQUENCE: 19

```
Asp Val Gln Leu Val Glu Ser Gly Ala Glu Leu Val Arg Pro Gly Ala
1               5                   10                  15

Ser Lys Leu Ser Cys Lys Ala Leu Ala Tyr Thr Phe Thr Asp Tyr Glu
                20                  25                  30

Met His Trp Val Lys Gln Thr Pro Val His Gly Leu Glu Trp Ile Gly
            35                  40                  45

Ile Ile His Pro Gly Ser Gly Gly Thr Val Tyr Asn Gln Lys Phe Lys
50                  55                  60

Gly Lys Ala Thr Leu Thr Ala Asp Lys Ser Ser Ser Thr Ala Tyr Met
65                  70                  75                  80

Glu Leu Ser Ser Leu Thr Ser Glu Asp Ser Thr Val Tyr Tyr Cys Thr
                85                  90                  95

Arg Arg Arg Tyr Tyr Gly Ser Ser Tyr Asn Trp Tyr Phe Asp Val Trp
            100                 105                 110

Gly Ala Gly Asn
            115
```

<210> SEQ ID NO 20
<211> LENGTH: 114
<212> TYPE: PRT
<213> ORGANISM: Artificial
<220> FEATURE:
<223> OTHER INFORMATION: Synthetic

<400> SEQUENCE: 20

```
Cys Asp Val Gln Leu Val Glu Ser Gly Gly Gly Leu Val Gln Pro Gly
1               5                   10                  15

Gly Ser Arg Lys Leu Ser Cys Ala Ala Ser Gly Phe Thr Phe Ser Asp
                20                  25                  30
```

Tyr Gly Met Ala Trp Val Arg Gln Ala Pro Gly Lys Gly Pro Glu Trp
            35                  40                  45

Val Ala Phe Ile Ser Asn Leu Ala Tyr Ser Ile Tyr Tyr Ser Asp Thr
 50                  55                  60

Val Thr Gly Arg Phe Thr Ile Ser Arg Glu Asn Ala Lys Asn Thr Leu
 65                  70                  75                  80

Tyr Leu Glu Met Ser Ser Leu Arg Ser Glu Asp Thr Ala Met Tyr Tyr
                85                  90                  95

Cys Ala Arg Gly Asp Tyr Ser Gly Gly Met Met Asp Tyr Trp Gly Gln
            100                 105                 110

Gly Thr

<210> SEQ ID NO 21
<211> LENGTH: 116
<212> TYPE: PRT
<213> ORGANISM: Artificial
<220> FEATURE:
<223> OTHER INFORMATION: Synthetic

<400> SEQUENCE: 21

Asp Val Gln Leu Val Glu Ser Gly Pro Gly Leu Val Lys Pro Ser Gln
 1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Ser Ser Ser Gly Asn Ser Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Glu Asp Thr Ala Thr Tyr Tyr Cys
                85                  90                  95

Ala Gly Ala Thr Gly Tyr Ser Met Asp Tyr Trp Gly Gln Gly Thr Thr
            100                 105                 110

Leu Thr Val Lys
        115

<210> SEQ ID NO 22
<211> LENGTH: 104
<212> TYPE: PRT
<213> ORGANISM: Artificial
<220> FEATURE:
<223> OTHER INFORMATION: Synthetic

<400> SEQUENCE: 22

Val Leu Thr Gln Ser Pro Ala Ser Leu Ala Ala Ser Val Gly Glu Thr
 1               5                   10                  15

Val Thr Ile Thr Cys Arg Ala Ser Glu Asn Ile Tyr Tyr Ser Leu Ala
                20                  25                  30

Trp Tyr Gln Gln Lys Gln Gly Lys Ser Pro Gln Leu Leu Ile Tyr Asn
            35                  40                  45

Ala Asn Ser Leu Glu Asp Gly Val Pro Ser Arg Phe Ser Gly Ser Gly
 50                  55                  60

Ser Gly Thr Gln Tyr Ser Leu Lys Ile Asn Ser Met Gln Pro Glu Asp
 65                  70                  75                  80

Thr Ala Thr Tyr Phe Cys Glu Gln Thr Tyr Asp Val Pro Leu Thr Phe
                85                  90                  95

Gly Ala Gly Thr Lys Leu Glu Leu
            100

<210> SEQ ID NO 23
<211> LENGTH: 106
<212> TYPE: PRT
<213> ORGANISM: Artificial
<220> FEATURE:
<223> OTHER INFORMATION: Synthetic

<400> SEQUENCE: 23

Val Leu Thr Ser Gln Pro Ala Ser Leu Ala Val Ser Leu Gly Gln Arg
1               5                   10                  15

Ala Thr Ile Ser Tyr Arg Ala Ser Lys Ser Val Ser Thr Ser Gly Tyr
            20                  25                  30

Ser Tyr Met His Trp Asn Gln Gln Lys Pro Gly Gln Pro Pro Arg Leu
        35                  40                  45

Leu Ile Tyr Leu Val Ser Asn Leu Glu Ser Gly Val Pro Ala Arg Phe
    50                  55                  60

Ser Gly Ser Gly Ser Gly Thr Asp Phe Thr Leu Asn Ile His Pro Val
65                  70                  75                  80

Glu Glu Glu Asp Ala Ala Thr Tyr Tyr Cys Gln His Ile Arg Glu Leu
                85                  90                  95

Thr Arg Ser Glu Gly Gly Pro Ser Trp Lys
            100                 105

<210> SEQ ID NO 24
<211> LENGTH: 106
<212> TYPE: PRT
<213> ORGANISM: Artificial
<220> FEATURE:
<223> OTHER INFORMATION: Synthetic

<400> SEQUENCE: 24

Val Leu Thr Gln Ser Pro Ala Ile Met Ser Ala Ser Leu Gly Glu Arg
1               5                   10                  15

Val Thr Met Thr Cys Thr Ala Ser Ser Ser Val Ser Ser Ser Tyr Leu
            20                  25                  30

His Trp Tyr Gln Gln Lys Pro Gly Ser Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys His Gln Tyr His Arg Ser Pro Phe Thr
                85                  90                  95

Phe Gly Ser Gly Thr Lys Leu Glu Leu Lys
            100                 105

<210> SEQ ID NO 25
<211> LENGTH: 11
<212> TYPE: PRT
<213> ORGANISM: Artificial
<220> FEATURE:
<223> OTHER INFORMATION: Synthetic

<400> SEQUENCE: 25

Ile His Pro Gly Ser Gly Gly Thr Val Tyr Asn
1               5                   10

```
<210> SEQ ID NO 26
<211> LENGTH: 7
<212> TYPE: PRT
<213> ORGANISM: Artificial
<220> FEATURE:
<223> OTHER INFORMATION: Synthetic

<400> SEQUENCE: 26

Tyr Tyr Gly Ser Ser Tyr Asn
1               5

<210> SEQ ID NO 27
<211> LENGTH: 3
<212> TYPE: PRT
<213> ORGANISM: Artificial
<220> FEATURE:
<223> OTHER INFORMATION: Synthetic

<400> SEQUENCE: 27

Asp Tyr Glu
1

<210> SEQ ID NO 28
<211> LENGTH: 10
<212> TYPE: PRT
<213> ORGANISM: Artificial
<220> FEATURE:
<223> OTHER INFORMATION: Synthetic

<400> SEQUENCE: 28

His Pro Gly Ser Gly Gly Thr Val Tyr Asn
1               5                   10

<210> SEQ ID NO 29
<211> LENGTH: 3
<212> TYPE: PRT
<213> ORGANISM: Artificial
<220> FEATURE:
<223> OTHER INFORMATION: Synthetic

<400> SEQUENCE: 29

Tyr Gly Ser
1

<210> SEQ ID NO 30
<211> LENGTH: 10
<212> TYPE: PRT
<213> ORGANISM: Artificial
<220> FEATURE:
<223> OTHER INFORMATION: Synthetic

<400> SEQUENCE: 30

Ile His Pro Gly Ser Gly Gly Thr Val Tyr
1               5                   10

<210> SEQ ID NO 31
<211> LENGTH: 6
<212> TYPE: PRT
<213> ORGANISM: Artificial
<220> FEATURE:
<223> OTHER INFORMATION: Synthetic

<400> SEQUENCE: 31

Tyr Gly Ser Ser Tyr Asn
1               5

<210> SEQ ID NO 32
```

```
<211> LENGTH: 9
<212> TYPE: PRT
<213> ORGANISM: Artificial
<220> FEATURE:
<223> OTHER INFORMATION: Synthetic

<400> SEQUENCE: 32

His Pro Gly Ser Gly Gly Thr Val Tyr
1               5

<210> SEQ ID NO 33
<211> LENGTH: 5
<212> TYPE: PRT
<213> ORGANISM: Artificial
<220> FEATURE:
<223> OTHER INFORMATION: Synthetic

<400> SEQUENCE: 33

Tyr Gly Ser Ser Tyr
1               5

<210> SEQ ID NO 34
<211> LENGTH: 8
<212> TYPE: PRT
<213> ORGANISM: Artificial
<220> FEATURE:
<223> OTHER INFORMATION: Synthetic

<400> SEQUENCE: 34

His Pro Gly Ser Gly Gly Thr Val
1               5

<210> SEQ ID NO 35
<211> LENGTH: 5
<212> TYPE: PRT
<213> ORGANISM: Artificial
<220> FEATURE:
<223> OTHER INFORMATION: Synthetic

<400> SEQUENCE: 35

Gly Ser Ser Tyr Asn
1               5

<210> SEQ ID NO 36
<211> LENGTH: 7
<212> TYPE: PRT
<213> ORGANISM: Artificial
<220> FEATURE:
<223> OTHER INFORMATION: Synthetic

<400> SEQUENCE: 36

His Pro Gly Ser Gly Gly Thr
1               5

<210> SEQ ID NO 37
<211> LENGTH: 6
<212> TYPE: PRT
<213> ORGANISM: Artificial
<220> FEATURE:
<223> OTHER INFORMATION: Synthetic

<400> SEQUENCE: 37

Pro Gly Ser Gly Gly Thr
1               5

<210> SEQ ID NO 38
<211> LENGTH: 11
```

```
<212> TYPE: PRT
<213> ORGANISM: Artificial
<220> FEATURE:
<223> OTHER INFORMATION: Synthetic

<400> SEQUENCE: 38

Arg Ala Ser Glu Asn Ile Tyr Tyr Ser Leu Ala
1               5                   10

<210> SEQ ID NO 39
<211> LENGTH: 11
<212> TYPE: PRT
<213> ORGANISM: Artificial
<220> FEATURE:
<223> OTHER INFORMATION: Synthetic

<400> SEQUENCE: 39

Asn Ala Asn Ser Leu Glu Asp Gly Val Pro Ser
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic

<400> SEQUENCE: 40

Ala Ser Glu Asn Ile Tyr Tyr Ser Leu Ala
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic

<400> SEQUENCE: 41

Ala Asn Ser Leu Glu Asp Gly Val Pro Ser
1               5                   10

<210> SEQ ID NO 42
<211> LENGTH: 212
<212> TYPE: PRT
<213> ORGANISM: Artificial
<220> FEATURE:
<223> OTHER INFORMATION: Synthetic

<400> SEQUENCE: 42

Met Val Leu Thr Gln Ser Pro Ala Ser Leu Ala Ala Ser Val Gly Glu
1               5                   10                  15

Thr Val Thr Ile Thr Cys Arg Ala Ser Glu Asn Ile Tyr Tyr Ser Leu
            20                  25                  30

Ala Trp Tyr Gln Gln Lys Gln Gly Lys Ser Pro Gln Leu Leu Ile Tyr
        35                  40                  45

Asn Ala Asn Ser Leu Glu Asp Gly Val Pro Ser Arg Phe Ser Gly Ser
    50                  55                  60

Gly Ser Gly Thr Gln Tyr Ser Leu Lys Ile Asn Ser Met Gln Pro Glu
65                  70                  75                  80

Asp Thr Ala Thr Tyr Phe Cys Gln Gln Thr Tyr Asp Val Pro Leu Thr
                85                  90                  95

Phe Gly Ala Gly Thr Lys Leu Glu Leu Arg Ala Asp Ala Ala Pro Thr
            100                 105                 110
```

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Arg Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 43
<211> LENGTH: 9
<212> TYPE: PRT
<213> ORGANISM: Artificial
<220> FEATURE:
<223> OTHER INFORMATION: Synthetic

<400> SEQUENCE: 43

Ala Ser Glu Asn Ile Tyr Tyr Ser Leu
1               5

<210> SEQ ID NO 44
<211> LENGTH: 9
<212> TYPE: PRT
<213> ORGANISM: Artificial
<220> FEATURE:
<223> OTHER INFORMATION: Synthetic

<400> SEQUENCE: 44

Ala Asn Ser Leu Glu Asp Gly Val Pro
1               5

<210> SEQ ID NO 45
<211> LENGTH: 8
<212> TYPE: PRT
<213> ORGANISM: Artificial
<220> FEATURE:
<223> OTHER INFORMATION: Synthetic

<400> SEQUENCE: 45

Ser Glu Asn Ile Tyr Tyr Ser Leu
1               5

<210> SEQ ID NO 46
<211> LENGTH: 8
<212> TYPE: PRT
<213> ORGANISM: Artificial
<220> FEATURE:
<223> OTHER INFORMATION: Synthetic

<400> SEQUENCE: 46

Asn Ser Leu Glu Asp Gly Val Pro
1               5

<210> SEQ ID NO 47
<211> LENGTH: 7
<212> TYPE: PRT
<213> ORGANISM: Artificial

```
<220> FEATURE:
<223> OTHER INFORMATION: Synthetic

<400> SEQUENCE: 47

Ser Glu Asn Ile Tyr Tyr Ser
1               5

<210> SEQ ID NO 48
<211> LENGTH: 7
<212> TYPE: PRT
<213> ORGANISM: Artificial
<220> FEATURE:
<223> OTHER INFORMATION: Synthetic

<400> SEQUENCE: 48

Asn Ser Leu Glu Asp Gly Val
1               5

<210> SEQ ID NO 49
<211> LENGTH: 6
<212> TYPE: PRT
<213> ORGANISM: Artificial
<220> FEATURE:
<223> OTHER INFORMATION: Synthetic

<400> SEQUENCE: 49

Glu Asn Ile Tyr Tyr Ser
1               5

<210> SEQ ID NO 50
<211> LENGTH: 6
<212> TYPE: PRT
<213> ORGANISM: Artificial
<220> FEATURE:
<223> OTHER INFORMATION: Synthetic

<400> SEQUENCE: 50

Ser Leu Glu Asp Gly Val
1               5

<210> SEQ ID NO 51
<211> LENGTH: 7
<212> TYPE: PRT
<213> ORGANISM: Artificial
<220> FEATURE:
<223> OTHER INFORMATION: Synthetic

<400> SEQUENCE: 51

Ile Gly Ile Ile His Pro Gly
1               5

<210> SEQ ID NO 52
<211> LENGTH: 6
<212> TYPE: PRT
<213> ORGANISM: Artificial
<220> FEATURE:
<223> OTHER INFORMATION: Synthetic

<400> SEQUENCE: 52

Ile Gly Ile Ile His Pro
1               5

<210> SEQ ID NO 53
<211> LENGTH: 6
<212> TYPE: PRT
<213> ORGANISM: Artificial
<220> FEATURE:
```

```
<223> OTHER INFORMATION: Synthetic

<400> SEQUENCE: 53

Gly Ile Ile His Pro Gly
1               5

<210> SEQ ID NO 54
<211> LENGTH: 5
<212> TYPE: PRT
<213> ORGANISM: Artificial
<220> FEATURE:
<223> OTHER INFORMATION: Synthetic

<400> SEQUENCE: 54

Gly Ile Ile His Pro
1               5

<210> SEQ ID NO 55
<211> LENGTH: 10
<212> TYPE: PRT
<213> ORGANISM: Artificial
<220> FEATURE:
<223> OTHER INFORMATION: Synthetic

<400> SEQUENCE: 55

Pro Gly Ser Gly Gly Thr Val Tyr Asn His
1               5                   10

<210> SEQ ID NO 56
<211> LENGTH: 9
<212> TYPE: PRT
<213> ORGANISM: Artificial
<220> FEATURE:
<223> OTHER INFORMATION: Synthetic

<400> SEQUENCE: 56

Gly Ser Gly Gly Thr Val Tyr Asn His
1               5

<210> SEQ ID NO 57
<211> LENGTH: 8
<212> TYPE: PRT
<213> ORGANISM: Artificial
<220> FEATURE:
<223> OTHER INFORMATION: Synthetic

<400> SEQUENCE: 57

Ser Gly Gly Thr Val Tyr Asn His
1               5

<210> SEQ ID NO 58
<211> LENGTH: 7
<212> TYPE: PRT
<213> ORGANISM: Artificial
<220> FEATURE:
<223> OTHER INFORMATION: Synthetic

<400> SEQUENCE: 58

Gly Gly Thr Val Tyr Asn His
1               5

<210> SEQ ID NO 59
<211> LENGTH: 8
<212> TYPE: PRT
<213> ORGANISM: Artificial
<220> FEATURE:
<223> OTHER INFORMATION: Synthetic
```

<400> SEQUENCE: 59

Arg Ala Ser Glu Asn Ile Tyr Tyr
1               5

<210> SEQ ID NO 60
<211> LENGTH: 10
<212> TYPE: PRT
<213> ORGANISM: Artificial
<220> FEATURE:
<223> OTHER INFORMATION: Synthetic

<400> SEQUENCE: 60

Asn Ala Asn Ser Leu Glu Asp Gly Val Pro
1               5                   10

<210> SEQ ID NO 61
<211> LENGTH: 7
<212> TYPE: PRT
<213> ORGANISM: Artificial
<220> FEATURE:
<223> OTHER INFORMATION: Synthetic

<400> SEQUENCE: 61

Arg Ala Ser Glu Asn Ile Tyr
1               5

<210> SEQ ID NO 62
<211> LENGTH: 981
<212> TYPE: DNA
<213> ORGANISM: Artificial
<220> FEATURE:
<223> OTHER INFORMATION: Synthetic

<400> SEQUENCE: 62

```
gctagcacca agggcccatc ggtcttcccc ctggcgccct gctccaggag cacctccgag      60
agcacagcgg ccctgggctg cctggtcaag gactacttcc ccgaaccggt gacggtgtcg     120
tggaactcag gcgctctgac cagcggcgtg cacaccttcc cagctgtcct acagtcctca     180
ggactctact ccctcagcag cgtggtgacc gtgccctcca gcaacttcgg cacccagacc     240
tacacctgca acgtagatca caagcccagc aacaccaagg tggacaagac agttgagcgc     300
aaatgttgtg tcgagtgccc accgtgccca gcaccacctg tggcaggacc gtcagtcttc     360
ctcttccccc caaaacccaa ggacaccctc atgatctccc ggacccctga ggtcacgtgc     420
gtggtggtgg acgtgagcca cgaagacccc gaggtccagt tcaactggta cgtggacggc     480
gtggaggtgc ataatgccaa gacaaagcca cgggaggagc agttcaacag cacgttccgt     540
gtggtcagcg tcctcaccgt tgtgcaccag gactggctga acggcaagga gtacaagtgc     600
aaggtctcca acaaaggcct cccagccccc atcgagaaaa ccatctccaa aaccaaaggg     660
cagccccgag aaccacaggt gtacaccctg cccccatccc gggaggagat gaccaagaac     720
caggtcagcc tgacctgcct ggtcaaaggc ttctacccca gcgacatcgc cgtggagtgg     780
gagagcaatg ggcagccgga gaacaactac aagaccacac ctcccatgct ggactccgac     840
ggctccttct tcctctacag caagctcacc gtggacaaga gcaggtggca gcaggggaac     900
gtcttctcat gctccgtgat gcatgaggct ctgcacaacc actacacgca gaagagcctc     960
tccctgtctc cgggtaaatg a                                               981
```

<210> SEQ ID NO 63
<211> LENGTH: 6

-continued

```
<212> TYPE: PRT
<213> ORGANISM: Artificial
<220> FEATURE:
<223> OTHER INFORMATION: Synthetic

<400> SEQUENCE: 63

Arg Ala Ser Glu Asn Ile
1               5

<210> SEQ ID NO 64
<211> LENGTH: 5
<212> TYPE: PRT
<213> ORGANISM: Artificial
<220> FEATURE:
<223> OTHER INFORMATION: Synthetic

<400> SEQUENCE: 64

Arg Ala Ser Glu Asn
1               5

<210> SEQ ID NO 65
<211> LENGTH: 9
<212> TYPE: PRT
<213> ORGANISM: Artificial
<220> FEATURE:
<223> OTHER INFORMATION: Synthetic

<400> SEQUENCE: 65

Ala Asn Ser Leu Glu Asp Gly Val Pro
1               5

<210> SEQ ID NO 66
<211> LENGTH: 8
<212> TYPE: PRT
<213> ORGANISM: Artificial
<220> FEATURE:
<223> OTHER INFORMATION: Synthetic

<400> SEQUENCE: 66

Asn Ser Leu Glu Asp Gly Val Pro
1               5

<210> SEQ ID NO 67
<211> LENGTH: 394
<212> TYPE: PRT
<213> ORGANISM: Homo sapiens

<400> SEQUENCE: 67

Met Phe Cys Pro Leu Lys Leu Ile Leu Leu Pro Val Leu Leu Asp Tyr
1               5                   10                  15

Ser Leu Gly Leu Asn Asp Leu Asn Val Ser Pro Pro Glu Leu Thr Val
                20                  25                  30

His Val Gly Asp Ser Ala Leu Met Gly Cys Val Phe Gln Ser Thr Glu
            35                  40                  45

Asp Lys Cys Ile Phe Lys Ile Asp Trp Thr Leu Ser Pro Gly Glu His
        50                  55                  60

Ala Lys Asp Glu Tyr Val Leu Tyr Tyr Tyr Ser Asn Leu Ser Val Pro
65                  70                  75                  80

Ile Gly Arg Phe Gln Asn Arg Val His Leu Met Gly Asp Ile Leu Cys
                85                  90                  95

Asn Asp Gly Ser Leu Leu Leu Gln Asp Val Gln Glu Ala Asp Gln Gly
                100                 105                 110

Thr Tyr Ile Cys Glu Ile Arg Leu Lys Gly Glu Ser Gln Val Phe Lys
```

```
            115                 120                 125
Lys Ala Val Val Leu His Val Leu Pro Glu Pro Lys Glu Leu Met
130                     135                 140

Val His Val Gly Gly Leu Ile Gln Met Gly Cys Val Phe Gln Ser Thr
145                 150                 155                 160

Glu Val Lys His Val Thr Lys Val Glu Trp Ile Phe Ser Gly Arg Arg
                165                 170                 175

Ala Lys Glu Glu Ile Val Phe Arg Tyr Tyr His Lys Leu Arg Met Ser
                180                 185                 190

Val Glu Tyr Ser Gln Ser Trp Gly His Phe Gln Asn Arg Val Asn Leu
                195                 200                 205

Val Gly Asp Ile Phe Arg Asn Asp Gly Ser Ile Met Leu Gln Gly Val
210                     215                 220

Arg Glu Ser Asp Gly Gly Asn Tyr Thr Cys Ser Ile His Leu Gly Asn
225                     230                 235                 240

Leu Val Phe Lys Lys Thr Ile Val Leu His Val Ser Pro Glu Glu Pro
                245                 250                 255

Arg Thr Leu Val Thr Pro Ala Ala Leu Arg Pro Leu Val Leu Gly Gly
                260                 265                 270

Asn Gln Leu Val Ile Ile Val Gly Ile Val Cys Ala Thr Ile Leu Leu
                275                 280                 285

Leu Pro Val Leu Ile Leu Ile Val Lys Lys Thr Cys Gly Asn Lys Ser
290                     295                 300

Ser Val Asn Ser Thr Val Leu Val Lys Asn Thr Lys Thr Asn Pro
305                     310                 315                 320

Glu Ile Lys Glu Lys Pro Cys His Phe Glu Arg Cys Glu Gly Glu Lys
                325                 330                 335

His Ile Tyr Ser Pro Ile Ile Val Arg Glu Val Ile Glu Glu Glu
                340                 345                 350

Pro Ser Glu Lys Ser Glu Ala Thr Tyr Met Thr Met His Pro Val Trp
                355                 360                 365

Pro Ser Leu Arg Ser Asp Arg Asn Asn Ser Leu Glu Lys Lys Ser Gly
                370                 375                 380

Gly Gly Met Pro Lys Thr Gln Gln Ala Phe
385                     390

<210> SEQ ID NO 68
<211> LENGTH: 326
<212> TYPE: PRT
<213> ORGANISM: Artificial
<220> FEATURE:
<223> OTHER INFORMATION: Synthetic

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
```

```
                85                  90                  95
Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 69
<211> LENGTH: 324
<212> TYPE: DNA
<213> ORGANISM: Artificial
<220> FEATURE:
<223> OTHER INFORMATION: Synthetic

<400> SEQUENCE: 69
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg ttag                                          324

<210> SEQ ID NO 70
<211> LENGTH: 107
<212> TYPE: PRT
<213> ORGANISM: Artificial
<220> FEATURE:
<223> OTHER INFORMATION: Synthetic

<400> SEQUENCE: 70
```

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 71
<211> LENGTH: 321
<212> TYPE: DNA
<213> ORGANISM: Artificial
<220> FEATURE:
<223> OTHER INFORMATION: Synthetic

<400> SEQUENCE: 71

```
ggccaaccga aagcggcgcc ctcggtcact ctgttcccgc cctcctctga ggagcttcaa    60
gccaacaagg ccacactggt gtgtctcata agtgacttct acccgggagc cgtgacagtg   120
gcctggaagg cagatagcag ccccgtcaag gcgggagtgg agaccaccac accctccaaa   180
caaagcaaca acaagtacgc ggccagcagc tatctgagcc tgacgcctga gcagtggaag   240
tcccacagaa gctacagctg ccaggtcacg catgaaggga gcaccgtgga agacagtg    300
gccctacag aatgttcata g                                              321
```

<210> SEQ ID NO 72
<211> LENGTH: 106
<212> TYPE: PRT
<213> ORGANISM: Artificial
<220> FEATURE:
<223> OTHER INFORMATION: Synthetic

<400> SEQUENCE: 72

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 73
<211> LENGTH: 330
<212> TYPE: PRT
<213> ORGANISM: Homo sapiens

<400> SEQUENCE: 73

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 74
<211> LENGTH: 326
<212> TYPE: PRT
<213> ORGANISM: Homo sapiens

<400> SEQUENCE: 74

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Leu
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 75
<211> LENGTH: 377
<212> TYPE: PRT
<213> ORGANISM: Homo sapiens

<400> SEQUENCE: 75

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
```

```
                65                  70                  75                  80
Tyr Thr Cys Asn Val Asn His Lys Pro Ser Asn Thr Lys Val Asp Lys
                    85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Cys Pro Arg
        115                 120                 125

Cys Pro Glu Pro Lys Ser Cys Asp Thr Pro Pro Cys Pro Arg Cys
    130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 76
<211> LENGTH: 327
<212> TYPE: PRT
<213> ORGANISM: Homo sapiens

<400> SEQUENCE: 76

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Ser Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 77
<211> LENGTH: 227
<212> TYPE: PRT
<213> ORGANISM: Artificial
<220> FEATURE:
<223> OTHER INFORMATION: Synthetic

<400> SEQUENCE: 77

Asp Lys Thr His Thr Cys Pro Pro Cys Pro Ala Pro Glu Leu Leu Gly
  1               5                  10                  15

Gly Pro Ser Val Phe Leu Phe Pro Pro Lys Pro Lys Asp Thr Leu Met
                 20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly Lys
225

<210> SEQ ID NO 78
<211> LENGTH: 332
<212> TYPE: PRT
<213> ORGANISM: Artificial
<220> FEATURE:
<223> OTHER INFORMATION: Synthetic

<400> SEQUENCE: 78

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
            115                 120                 125

Val Tyr Thr Leu Pro Pro Ser Arg Asp Glu Leu Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
            210                 215                 220
```

```
Ser Pro Gly Lys Val Leu Thr Gln Ser Pro Ala Ser Leu Ala Ala Ser
225                 230                 235                 240

Val Gly Glu Thr Val Thr Ile Thr Cys Arg Ala Ser Glu Asn Ile Tyr
            245                 250                 255

Tyr Ser Leu Ala Trp Tyr Gln Gln Lys Gln Gly Lys Ser Pro Gln Leu
        260                 265                 270

Leu Ile Tyr Asn Ala Asn Ser Leu Glu Asp Gly Val Pro Ser Arg Phe
        275                 280                 285

Ser Gly Ser Gly Ser Gly Thr Gln Tyr Ser Leu Lys Ile Asn Ser Met
290                 295                 300

Gln Pro Glu Asp Thr Ala Thr Tyr Phe Cys Glu Gln Thr Tyr Asp Val
305                 310                 315                 320

Pro Leu Thr Phe Gly Ala Gly Thr Lys Leu Glu Leu
                325                 330

<210> SEQ ID NO 79
<211> LENGTH: 327
<212> TYPE: PRT
<213> ORGANISM: Artificial
<220> FEATURE:
<223> OTHER INFORMATION: Synthetic

<400> SEQUENCE: 79

Met Val Leu Thr Gln Ser Pro Ala Ser Leu Ala Ala Ser Val Gly Glu
1               5                   10                  15

Thr Val Thr Ile Thr Cys Arg Ala Ser Glu Asn Ile Tyr Tyr Ser Leu
            20                  25                  30

Ala Trp Tyr Gln Gln Lys Gln Gly Lys Ser Pro Gln Leu Leu Ile Tyr
        35                  40                  45

Asn Ala Asn Ser Leu Glu Asp Gly Val Pro Ser Arg Phe Ser Gly Ser
    50                  55                  60

Gly Ser Gly Thr Gln Tyr Ser Leu Lys Ile Asn Ser Met Gln Pro Glu
65                  70                  75                  80

Asp Thr Ala Thr Tyr Phe Cys Glu Gln Thr Tyr Asp Val Pro Leu Thr
                85                  90                  95

Phe Gly Ala Gly Thr Lys Leu Glu Leu Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255
```

```
Phe Tyr Pro Ser Asp Ile Ala Val Glu Trp Glu Ser Asn Gly Gln Pro
                260                 265                 270

Glu Asn Asn Tyr Lys Thr Thr Pro Pro Val Leu Asp Ser Asp Gly Ser
            275                 280                 285

Phe Phe Leu Tyr Ser Lys Leu Thr Val Asp Lys Ser Arg Trp Gln Gln
        290                 295                 300

Gly Asn Val Phe Ser Cys Ser Val Met His Glu Ala Leu His Asn His
305                 310                 315                 320

Tyr Thr Gln Lys Ser Leu Ser
                325

<210> SEQ ID NO 80
<211> LENGTH: 344
<212> TYPE: PRT
<213> ORGANISM: Artificial
<220> FEATURE:
<223> OTHER INFORMATION: Synthetic

<400> SEQUENCE: 80

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys Asp Val Gln Leu Val Glu Ser Gly Ala Glu Leu Val
225                 230                 235                 240

Arg Pro Gly Ala Ser Val Lys Leu Ser Cys Lys Ala Leu Ala Tyr Thr
                245                 250                 255

Phe Thr Asp Tyr Glu Met His Trp Val Lys Gln Thr Pro Val His Gly
            260                 265                 270

Leu Glu Trp Ile Gly Ile His Pro Gly Ser Gly Thr Val Tyr
        275                 280                 285
```

```
Asn Gln Lys Phe Lys Gly Lys Ala Thr Leu Thr Ala Asp Lys Ser Ser
    290                 295                 300
Ser Thr Ala Tyr Met Glu Leu Ser Ser Leu Thr Ser Glu Asp Ser Thr
305                 310                 315                 320
Val Tyr Tyr Cys Thr Arg Arg Tyr Tyr Gly Ser Ser Tyr Trp Tyr
                325                 330                 335
Phe Asp Val Trp Gly Ala Gly Asn
                340

<210> SEQ ID NO 81
<211> LENGTH: 344
<212> TYPE: PRT
<213> ORGANISM: Artificial
<220> FEATURE:
<223> OTHER INFORMATION: Synthetic

<400> SEQUENCE: 81

Met Asp Val Gln Leu Val Glu Ser Gly Ala Glu Leu Val Arg Pro Gly
1               5                   10                  15
Ala Ser Val Lys Leu Ser Cys Lys Ala Leu Ala Tyr Thr Phe Thr Asp
                20                  25                  30
Tyr Glu Met His Trp Val Lys Gln Thr Pro Val His Gly Leu Glu Trp
            35                  40                  45
Ile Gly Ile Ile His Pro Gly Ser Gly Gly Thr Val Tyr Asn Gln Lys
        50                  55                  60
Phe Lys Gly Lys Ala Thr Leu Thr Ala Asp Lys Ser Ser Ser Thr Ala
65                  70                  75                  80
Tyr Met Glu Leu Ser Ser Leu Thr Ser Glu Asp Ser Val Tyr Tyr
                85                  90                  95
Cys Thr Arg Arg Tyr Tyr Gly Ser Ser Tyr Trp Tyr Phe Asp Val
                100                 105                 110
Trp Gly Ala Gly Asn Asp Lys Thr His Thr Cys Pro Pro Cys Pro Ala
            115                 120                 125
Pro Glu Leu Leu Gly Gly Pro Ser Val Phe Leu Phe Pro Pro Lys Pro
130                 135                 140
Lys Asp Thr Leu Met Ile Ser Arg Thr Pro Glu Val Thr Cys Val Val
145                 150                 155                 160
Val Asp Val Ser His Glu Asp Pro Glu Val Lys Phe Asn Trp Tyr Val
                165                 170                 175
Asp Gly Val Glu Val His Asn Ala Lys Thr Lys Pro Arg Glu Glu Gln
            180                 185                 190
Tyr Asn Ser Thr Tyr Arg Val Val Ser Val Leu Thr Val Leu His Gln
        195                 200                 205
Asp Trp Leu Asn Gly Lys Glu Tyr Lys Cys Lys Val Ser Asn Lys Ala
210                 215                 220
Leu Pro Ala Pro Ile Glu Lys Thr Ile Ser Lys Ala Lys Gly Gln Pro
225                 230                 235                 240
Arg Glu Pro Gln Val Tyr Thr Leu Pro Pro Ser Arg Asp Glu Leu Thr
                245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
        275                 280                 285
Lys Thr Thr Pro Pro Val Leu Asp Ser Asp Gly Ser Phe Phe Leu Tyr
    290                 295                 300
```

```
Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 82
<211> LENGTH: 107
<212> TYPE: PRT
<213> ORGANISM: Artificial
<220> FEATURE:
<223> OTHER INFORMATION: Synthetic

<400> SEQUENCE: 82

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Arg Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105
```